United States Patent
Frohberg et al.

(10) Patent No.: US 9,150,873 B2
(45) Date of Patent: Oct. 6, 2015

(54) PLANTS WHICH SYNTHESIZE INCREASED AMOUNTS OF GLUCOSAMINOGLYCANS

(75) Inventors: Claus Frohberg, Kleinmachnow (DE); Bernd Essigmann, Berlin (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 527 days.

(21) Appl. No.: 12/733,613

(22) PCT Filed: Sep. 11, 2008

(86) PCT No.: PCT/EP2008/007837
§ 371 (c)(1),
(2), (4) Date: Mar. 11, 2010

(87) PCT Pub. No.: WO2009/033752
PCT Pub. Date: Mar. 19, 2009

(65) Prior Publication Data
US 2010/0196966 A1    Aug. 5, 2010

Related U.S. Application Data

(60) Provisional application No. 60/993,575, filed on Sep. 13, 2007.

(30) Foreign Application Priority Data

Sep. 12, 2007 (EP) .................................. 07116174

(51) Int. Cl.
| C12N 5/14 | (2006.01) |
| A01H 5/00 | (2006.01) |
| C12N 15/82 | (2006.01) |
| C12N 1/04 | (2006.01) |
| C12N 1/06 | (2006.01) |
| C12N 1/08 | (2006.01) |

(52) U.S. Cl.
CPC .............. *C12N 15/8246* (2013.01); *C12N 1/04* (2013.01); *C12N 1/06* (2013.01); *C12N 1/08* (2013.01)

(58) Field of Classification Search
None
See application file for complete search history.

(56) References Cited

U.S. PATENT DOCUMENTS

| 4,141,973 | A | 2/1979 | Balazs |
| 4,782,046 | A | 11/1988 | Brown et al. |
| 4,801,539 | A | 1/1989 | Akasaka et al. |
| 4,897,349 | A | 1/1990 | Swann et al. |
| 5,019,498 | A | 5/1991 | Chichibu |
| 5,565,347 | A | 10/1996 | Fillatti et al. |
| 6,369,298 | B1 | 4/2002 | Cai et al. |
| 6,444,878 | B1 | 9/2002 | Donaldson et al. |
| 6,455,304 | B1 | 9/2002 | Weigel et al. |
| 6,607,745 | B2 | 8/2003 | Leneau |
| 8,003,851 | B2 * | 8/2011 | Kitazawa et al. ............. 800/288 |
| 2002/0088023 | A1 | 7/2002 | Kossmann et al. |
| 2003/0104601 | A1 | 6/2003 | DeAngelis |
| 2003/0109693 | A1 | 6/2003 | Ninomiya et al. |
| 2003/0175902 | A1 | 9/2003 | Sloma et al. |
| 2003/0235893 | A1 | 12/2003 | Weigel et al. |
| 2004/0003432 | A1 * | 1/2004 | Obukowicz .................. 800/284 |
| 2005/0048604 | A1 | 3/2005 | Sugahara et al. |
| 2006/0052335 | A1 | 3/2006 | Narimatsu et al. |
| 2006/0115545 | A1 * | 6/2006 | Frohberg et al. ............. 424/750 |
| 2006/0168690 | A1 | 7/2006 | Shibatani et al. |
| 2008/0250533 | A1 | 10/2008 | Frohberg |
| 2009/0260108 | A1 | 10/2009 | Kitazawa et al. |

FOREIGN PATENT DOCUMENTS

| EP | 0 120 516 | 10/1984 |
| EP | 0 144 019 | 6/1985 |
| EP | 0 292 435 | 11/1988 |
| EP | 0 465 875 | 1/1992 |
| EP | 0 513 849 | 11/1992 |
| EP | 0 694 616 | 1/1996 |
| EP | 1 283 259 | 2/2003 |
| EP | 1 640 457 | 3/2006 |
| WO | WO 93/07279 | 4/1993 |
| WO | WO 95/06128 | 3/1995 |
| WO | WO 97/44472 | 11/1997 |
| WO | WO 98/35047 | 8/1998 |
| WO | WO 01/73087 | 10/2001 |
| WO | WO 03/012099 | 2/2003 |
| WO | WO 03/054163 | 7/2003 |
| WO | WO 2005/012529 | 2/2005 |
| WO | WO 2006/032538 | 3/2006 |

(Continued)

OTHER PUBLICATIONS

Milewski et al, 2006, Yeast, 23:1-14.*
Mio et al, 1998, J. Biol. Chem., 273:14392-14397.*
Gebauer, Bernhard, Inaugural-Dissertation, Virchow-Klinikum Med. Fakultat Charite der Humboldt Universitat zu Berlin (1998).
An et al., The EMBO Journal, vol. 4, No. 2, pp. 277-284 (1985).
Arencibia et al., Transgenic Research, vol. 7, pp. 213-222 (1998).
Bachem et al., The Plant Journal, vol. 9, No. 5, pp. 745-753 (1996).
Baumlein et al., Molecular Genetics and Genomics, vol. 225, pp. 459-467 (1991).
Becker et al., The Plant Journal, vol. 5, No. 2, pp. 299-307 (1994).
Becker, Nucleic Acids Research, vol. 18, No. 1, p. 203, Nov. 15, 1999.
Bevan, Nucleic Acids Research, vol. 12, No. 22, pp. 8711-8721 (1984).

(Continued)

*Primary Examiner* — Ashwin Mehta
*Assistant Examiner* — Jason Deveau Rosen
(74) *Attorney, Agent, or Firm* — Hunton & Williams LLP

(57) ABSTRACT

The present invention relates to plant cells and plants which synthesize an increased amount of glucosaminoglycans, and to methods for preparing such plants, and also to methods for preparing glucosaminoglycans with the aid of these plant cells or plants. Here, plant cells or genetically modified plants according to the invention have glucosaminoglycan synthase activity and additionally an increased glucosamine 6-phosphate acetyltransferase activity and an increased UDP-N-acetyl-glucosamine pyrophosphorylase activity compared to wild-type plant cells or wild-type plants. The present invention furthermore relates to compositions comprising plant cells having an increased glucosaminoglycan synthesis.

45 Claims, No Drawings

(56) References Cited

FOREIGN PATENT DOCUMENTS

| WO | WO 2007/023682 | | 3/2007 |
| WO | WO 2007023682 A1 | * | 3/2007 |
| WO | WO 2007/039314 | | 4/2007 |
| WO | WO 2007/039315 | | 4/2007 |
| WO | WO 2007/039316 | | 4/2007 |

OTHER PUBLICATIONS

Bower et al., Molecular Breeding, vol. 2, pp. 239-249 (1996).
Bower et al., The Plant Journal, vol. 2, No. 3, pp. 409-416 (1992).
Busse et al., The Journal of Biological Chemistry, vol. 278, No. 42, Issue of Oct. 17, pp. 41333-41337 (2003).
Callis et al., Genes and Development, vol. 1, pp. 1183-1200 (1987).
Casas et al., Proceedings of the National Academy of Sciences of the USA, vol. 90, pp. 11212-11216, Dec. 1993.
Castiglioni et al., Genetics Society of America, vol. 149, pp. 2039-2056, Aug. 1998.
Chan et al., Plant Molecular Biology, vol. 22, pp. 491-506 (1993).
Chien et al., Biotechnology Progress, vol. 23, No. 5, pp. 1017-1022 (2007).
Christensen et al., Transgenic Research, vol. 5, pp. 213-218 (1996).
Clegg et al., The New England Journal of Medicine, vol. 354, No. 8, pp. 795-808 (2006).
Conner et al., International Journal of Plant Science, vol. 153, No. 4, pp. 550-555 (1992).
Deangelis et al., Journal of Bacteriology, vol. 186, No. 24, pp. 8529-8532, Dec. 2004.
Deangelis et al., Science Magazine, vol. 278, No. 5344, pp. 1800-1803, Dec. 5, 1997.
Deangelis et al., The Journal of Biological Chemistry, vol. 275, No. 31, Issue of Aug. 4, pp. 24124-24129 (2000).
Deangelis, Cellular and Molecular Life Sciences, vol. 56, pp. 670-682 (1999).
Deng et al., Science in China (Series B), vol. 33, No. 1, pp. 27-34, Jan. 1990.
Derose et al., Plant Molecular Biology, vol. 32, pp. 1029-1035 (1996).
Fiedler et al., Plant Molecular Biology, vol. 22, pp. 669-679 (1993).
Fraser et al., Journal of Internal Medicine, vol. 242, pp. 27-33, (1997).
Frayley et al., CRC Critical Reviews in Plant Sciences, vol. 4, Issue 1, pp. 1-46 (1986).
Fromm et al., Biotechnology, vol. 8. pp. 833-839, Sep. 1990.
Gallagher et al., International Journal of Biochemistry, vol. 24, No. 4, pp. 553-560 (1992).
Gehring et al., Biochemistry, vol. 35, pp. 579-585 (1996).
Gielen et al., The EMBO Journal, vol. 3, No. 4, pp. 835-846 (1984).
Goa et al., Drugs, vol. 47, No. 3, pp. 536-566 (1994).
Gordan-Kamm et al., The Plant Cell, vol. 2, pp. 603-618, Jul. 1990.
Graves et al., Virology, vol. 257, pp. 15-23 (1999).
Herrera-Estrella et al., Nature, vol. 303, pp. 209-213, May 1983.
Hiel et al., The Plant Journal, vol. 6, No. 2, pp. 271-282 (1994).
Hoekema et al., Plant Molecular Biology, vol. 5, No. 2, pp. 63-71 (1985).
Hofgen et al., Plant Science, vol. 66, pp. 221-230 (1990).
Hu et al., The Journal of Biological Chemistry, vol. 279, No. 29, Issue of Jul. 16, pp. 29988-29993 (2004).
Itano et al., The Journal of Biological Chemistry, vol. 279, No. 18, Issue of Apr. 30, pp. 18679-18687 (2004).
Jarvis et al., Plant Molecular Biology, vol. 24, pp. 685-687 (19994).
Kitagawa et al., The Journal of Biological Chemistry, vol. 276, No. 42, Issue of Oct. 19, pp. 38721-38726 (2001).
Knudson et al., The FASEB Journal, vol. 7, pp. 1233-1241, Oct. 1993.
Konieczny et al., The Plant Journal, vol. 4, No. 2, pp. 403-410 (1993).
Koziel et al., Bio/Technology, vol. 11, pp. 194-200, Feb. 1993.
Krens et al., Nature, vol. 296, Mar. 4, 1982.
Lapcik, Jr. et al., Chemical Reviews, vol. 98, No. 8, pp. 2663-2684, Dec. 1998.
Laurent et al., The FASEB Journal, vol. 6, pp. 2397-2404, Apr. 1992.
Leisy et al., Plant Molecular Biology, vol. 14, pp. 41-50 (1989).
Lister et al., The Plant Journal, vol. 4, No. 4, pp. 745-750 (1993).
Luehrsen et al., Molecular Genetics and Genomics, vol. 225, pp. 81-93 (1991).
May et al., Bio/Technology, vol. 13, pp. 486-492, May 13, 1995.
Mayer et al., Plant Physiology, vol. 43, pp. 1097-1107 (1968).
Mehta et al., Nature Biotechnology, vol. 20, pp. 613-618, Jun. 2002.
Meksem et al., Molecular Genetics and Genomics, vol. 265, pp. 207-214 (2001).
Meyer et al., Molecular Genetics and Genomics, vol. 259, pp. 150-160 (1198).
Milewski et al., Yeast, vol. 23, pp. 1-14 (2006).
Mio et al., The Journal of Biological Chemistry, vol. 273, No. 23, Issue of Jun. 5, pp. 14392-14397 (1998).
Mishra et al., Molecular Biology Reporter, vol. 35, pp. 81-88 (2008).
Mitra et al., Biochemical and Biophysical Research Communications, vol. 204, No. 1, pp. 187-194, Oct. 14, 1994.
Mitra et al., Plant Molecular Biology, vol. 26, pp. 85-93 (1994).
Mizuguchi et al., Nature, vol. 423, pp. 443-448, May 22, 2003.
Mok et al., The Journal of Biological Chemistry, vol. 280, No. 47, pp. 39363-39372, Nov. 25, 2005.
Montgomery et al., The Plant Cell, vol. 5, pp. 1049-1062, Sep. 1993.
Moon et al. Journal Experimental Botany, vol. 55, No. 402, pp. 1519-1528, Jul. 2004.
Morocz et al., Theoretical and Applied Genetics, vol. 80, pp. 721-726 (1990).
Nam et al., The Plant Cell, vol. 1, pp. 699-705, Jul. 1989.
Nehra et al., The Plant Journal, vol. 5, No. 2, pp. 285-297 (1994).
Ouskova et al., Glycobiology, vol. 14, No. 10, pp. 931-938 (2004).
Pedersen et al., Cell, vol. 29, pp. 1015-1026, Jul. 1982.
Peneff et al., The Journal of Biological Chemistry, vol. 276, No. 19, Issue of May 11, pp. 16328-16334 (2001).
Pietrzak et al., Nucleic Acids Research, vol. 14, No. 14, pp. 5857-5868 (1986).
Prehm et al., Biochemical Pharmacology, vol. 68, pp. 1401-1410 (2004).
Quattrocchio et al., Plant Molecular Biology, vol. 15, pp. 81-93 (1990).
Rethmeier et al., The Plant Journal, vol. 12, No. 4, pp. 895-899 (1997).
Richards et al., Plant Cell Reports, vol. 20, pp. 48-54 (2001).
Ritala et al., Plant Molecular Biology, vol. 24, pp. 317-325 (1994).
Ritchie et al., Transgenic Research, vol. 2, pp. 252-265 (1993).
Rocha-Sosa et al., The EMBO Journal, vol. 8, No. 1, pp. 23-29 (1989).
Rose et al., Plant Physiology, vol. 122, pp. 535-542, Feb. 2000.
Sambrook et al., Molecular Cloning: A Laboratory Manual, vol. 1 (2001).
Smith et al., Journal of Bacteriology vol. 178, No. 8, pp. 2320-2327 (1996).
Somleva et al., Crop Science, vol. 42, pp. 2080-2087 (2002).
Spencer et al., Theoretical and Applied Genetics, vol. 79, pp. 625-631 (1990).
Stamenkovic et al., Methods in Enzymology, vol. 245, pp. 195-216 (1994).
Stavolone et al., Plant Molecular Biology, vol. 53, pp. 703-713 (2003).
Stockhuas et al., Proceedings of the National Academy of Sciences of the USA, vol. 84, pp. 7943-7947, Nov. 1987.
Stockhuas et al., The EMBO Journal, vol. 8, No. 9, pp. 2445-2451 (1989).
Thompson et al., Nucleic Acids Research, vol. 22, No. 22, pp. 4673-4680 1994).
Turley et al., Advanced Drug Delivery Reviews, vol. 7, pp. 257-264 (1991).
Van Etten et al., Annual Review of Microbiology, vol. 53, pp. 447-494 (1999).
Van Etten et al., Archives of Virology, vol. 147, pp. 1479-1516 (2002).
Vasil et al., Bio/Technology, vol. 11, pp. 1553-1558 (1983).
Vasil et al., Plant Physiology, vol. 91, pp. 1575-1579 (1989).

(56) References Cited

OTHER PUBLICATIONS

Volpi et al., Biochimie, vol. 85, pp. 619-625 (2003).
Wan et al., Plant Physiology, vol. 104, pp. 37-48 (1994).
Wang et al., The Journal of Biological Chemistry, vol. 275, No. 2, Issue of Jan. 14, pp. 1433-1438 (2000).
Werr et al., The EMBO Journal, vol. 4, No. 6, pp. 1373-1380 (1985).
Wilmink et al., Plant Cell Reports, vol. 11, pp. 76-80 (1992).
Xu et al., Science in China, vol. 46, No. 6, Dec. 2003.
Yoshihara et al., FEBS Letters, vol. 383, pp. 213-218 (1996).
Zheng et al., The Plant Journal, vol. 4, No. 2, pp. 357-366 (1993).
International Search Report for international Application No. PCT/EP2008/007837 mailed Dec. 12, 2008.
Lesage et al., "Cell Wall Assembly in *Saccharomyces cerevisiae*," (2006) Microbiol. Mol. Biol. Rev., vol. 70, No. 2, pp. 317-343.
DeAngelis, P., "Evolution of Glycosaminoglycans and Their Glycosyltransferases: Implications for the Extracellular Matrices of Animals and the Capsules of Pathogenic Bacteria," (2002) The Anatomical Record, vol. 268, pp. 317-326.
DeAngelis, P. et al., "Yeast-derived Recombinant DG42 Protein of *Xenopus* Can Synthesize Hyaluronan in Vitro," (1996) The Journal of Biological Chemistry, vol. 271, No. 39, pp. 23657-23660.

* cited by examiner

SEQUENCE LISTING

<160> NUMBER OF SEQ ID NOS: 34

<210> SEQ ID NO 1
<211> LENGTH: 1707
<212> TYPE: DNA
<213> ORGANISM: Paramecium bursaria Chlorella Virus 1
<220> FEATURE:
<221> NAME/KEY: CDS
<222> LOCATION: (1)..(1707)
<300> PUBLICATION INFORMATION:
<308> DATABASE ACCESSION NUMBER: GenBank/U4258beta
<309> DATABASE ENTRY DATE: 1995-12-24
<313> RELEVANT RESIDUES IN SEQ ID NO: (50903)..(52609)

<400> SEQUENCE: 1

| | | | | | | | | | | | | | | | | |
|---|---|---|---|---|---|---|---|---|---|---|---|---|---|---|---|---|
| atg | ggt | aaa | aat | ata | atc | ata | atg | gtt | tcg | tgg | tac | acc | ata | ata | act | 48 |
| Met | Gly | Lys | Asn | Ile | Ile | Ile | Met | Val | Ser | Trp | Tyr | Thr | Ile | Ile | Thr | |
| 1 | | | | 5 | | | | | 10 | | | | | 15 | | |
| tca | aat | cta | atc | gcg | gtt | gga | gga | gcc | tct | cta | atc | ttg | gct | ccg | gca | 96 |
| Ser | Asn | Leu | Ile | Ala | Val | Gly | Gly | Ala | Ser | Leu | Ile | Leu | Ala | Pro | Ala | |
| | | | 20 | | | | | 25 | | | | | 30 | | | |
| att | act | ggg | tat | gtt | cta | cat | tgg | aat | att | gct | ctc | tcg | aca | atc | tgg | 144 |
| Ile | Thr | Gly | Tyr | Val | Leu | His | Trp | Asn | Ile | Ala | Leu | Ser | Thr | Ile | Trp | |
| | | 35 | | | | | 40 | | | | | 45 | | | | |
| gga | gta | tca | gct | tat | ggt | att | ttc | gtt | ttt | ggg | ttt | ttc | ctt | gca | caa | 192 |
| Gly | Val | Ser | Ala | Tyr | Gly | Ile | Phe | Val | Phe | Gly | Phe | Phe | Leu | Ala | Gln | |
| | 50 | | | | | 55 | | | | | 60 | | | | | |
| gtt | tta | ttt | tca | gaa | ctg | aac | agg | aaa | cgt | ctt | cgc | aag | tgg | att | tct | 240 |
| Val | Leu | Phe | Ser | Glu | Leu | Asn | Arg | Lys | Arg | Leu | Arg | Lys | Trp | Ile | Ser | |
| 65 | | | | | 70 | | | | | 75 | | | | | 80 | |
| ctc | aga | cct | aag | ggt | tgg | aat | gat | gtt | cgt | ttg | gct | gtg | atc | att | gct | 288 |
| Leu | Arg | Pro | Lys | Gly | Trp | Asn | Asp | Val | Arg | Leu | Ala | Val | Ile | Ile | Ala | |
| | | | | 85 | | | | | 90 | | | | | 95 | | |
| gga | tat | cgc | gag | gat | cct | tat | atg | ttc | cag | aag | tgc | ctc | gag | tct | gta | 336 |
| Gly | Tyr | Arg | Glu | Asp | Pro | Tyr | Met | Phe | Gln | Lys | Cys | Leu | Glu | Ser | Val | |
| | | | 100 | | | | | 105 | | | | | 110 | | | |
| cgt | gac | tct | gat | tat | ggc | aac | gtt | gcc | cgt | ctg | att | tgt | gtg | att | gac | 384 |
| Arg | Asp | Ser | Asp | Tyr | Gly | Asn | Val | Ala | Arg | Leu | Ile | Cys | Val | Ile | Asp | |
| | | 115 | | | | | 120 | | | | | 125 | | | | |
| ggt | gat | gag | gac | gat | gat | atg | agg | atg | gct | gcc | gtt | tac | aag | gcg | atc | 432 |
| Gly | Asp | Glu | Asp | Asp | Asp | Met | Arg | Met | Ala | Ala | Val | Tyr | Lys | Ala | Ile | |
| | 130 | | | | | 135 | | | | | 140 | | | | | |
| tac | aat | gat | aat | atc | aag | aag | ccc | gag | ttt | gtt | ctg | tgt | gag | tca | gac | 480 |
| Tyr | Asn | Asp | Asn | Ile | Lys | Lys | Pro | Glu | Phe | Val | Leu | Cys | Glu | Ser | Asp | |
| 145 | | | | | 150 | | | | | 155 | | | | | 160 | |
| gac | aag | gaa | ggt | gaa | cgc | atc | gac | tct | gat | ttc | tct | cgc | gac | att | tgt | 528 |
| Asp | Lys | Glu | Gly | Glu | Arg | Ile | Asp | Ser | Asp | Phe | Ser | Arg | Asp | Ile | Cys | |
| | | | | 165 | | | | | 170 | | | | | 175 | | |
| gtc | ctc | cag | cct | cat | cgt | gga | aaa | cgg | gag | tgt | ctt | tat | act | ggg | ttt | 576 |
| Val | Leu | Gln | Pro | His | Arg | Gly | Lys | Arg | Glu | Cys | Leu | Tyr | Thr | Gly | Phe | |
| | | | 180 | | | | | 185 | | | | | 190 | | | |
| caa | ctt | gca | aag | atg | gac | ccc | agt | gtc | aat | gct | gtc | gtt | ctg | att | gac | 624 |
| Gln | Leu | Ala | Lys | Met | Asp | Pro | Ser | Val | Asn | Ala | Val | Val | Leu | Ile | Asp | |
| | | 195 | | | | | 200 | | | | | 205 | | | | |
| agc | gat | acc | gtt | ctc | gag | aag | gat | gct | att | ctg | gaa | gtt | gta | tac | cca | 672 |
| Ser | Asp | Thr | Val | Leu | Glu | Lys | Asp | Ala | Ile | Leu | Glu | Val | Val | Tyr | Pro | |
| | 210 | | | | | 215 | | | | | 220 | | | | | |
| ctt | gca | tgc | gat | ccc | gag | atc | caa | gcc | gtt | gca | ggt | gag | tgt | aag | att | 720 |
| Leu | Ala | Cys | Asp | Pro | Glu | Ile | Gln | Ala | Val | Ala | Gly | Glu | Cys | Lys | Ile | |
| 225 | | | | | 230 | | | | | 235 | | | | | 240 | |
| tgg | aac | aca | gac | act | ctt | ttg | agt | ctt | ctc | gtc | gct | tgg | cgg | tac | tat | 768 |
| Trp | Asn | Thr | Asp | Thr | Leu | Leu | Ser | Leu | Leu | Val | Ala | Trp | Arg | Tyr | Tyr | |

-continued

|                                                                                                                |      |
|----------------------------------------------------------------------------------------------------------------|------|
|                         245                         250                         255                            |      |
| tct gcg ttt tgt gtg gag agg agt gcc cag tct ttt ttc agg act gtt                                                | 816  |
| Ser Ala Phe Cys Val Glu Arg Ser Ala Gln Ser Phe Phe Arg Thr Val                                                |      |
|             260                         265                         270                                        |      |
| cag tgc gtt ggg ggg cca ctg ggt gcc tac aag att gat atc att aag                                                | 864  |
| Gln Cys Val Gly Gly Pro Leu Gly Ala Tyr Lys Ile Asp Ile Ile Lys                                                |      |
|             275                         280                         285                                        |      |
| gag att aag gac ccc tgg att tcc cag cgc ttt ctt ggt cag aag tgt                                                | 912  |
| Glu Ile Lys Asp Pro Trp Ile Ser Gln Arg Phe Leu Gly Gln Lys Cys                                                |      |
|             290                         295                         300                                        |      |
| act tac ggt gac gac cgc cgg cta acc aac gag atc ttg atg cgt ggt                                                | 960  |
| Thr Tyr Gly Asp Asp Arg Arg Leu Thr Asn Glu Ile Leu Met Arg Gly                                                |      |
| 305                         310                         315                         320                        |      |
| aaa aag gtt gtg ttc act cca ttt gct gtt ggt tgg tct gac agt ccg                                                | 1008 |
| Lys Lys Val Val Phe Thr Pro Phe Ala Val Gly Trp Ser Asp Ser Pro                                                |      |
|             325                         330                         335                                        |      |
| acc aat gtg ttt cgg tac atc gtt cag cag acc cgc tgg agt aag tcg                                                | 1056 |
| Thr Asn Val Phe Arg Tyr Ile Val Gln Gln Thr Arg Trp Ser Lys Ser                                                |      |
|             340                         345                         350                                        |      |
| tgg tgc cgc gaa att tgg tac acc ctc ttc gcc gcg tgg aag cac ggt                                                | 1104 |
| Trp Cys Arg Glu Ile Trp Tyr Thr Leu Phe Ala Ala Trp Lys His Gly                                                |      |
|             355                         360                         365                                        |      |
| ttg tct gga att tgg ctg gcc ttt gaa tgt ttg tat caa att aca tac                                                | 1152 |
| Leu Ser Gly Ile Trp Leu Ala Phe Glu Cys Leu Tyr Gln Ile Thr Tyr                                                |      |
|             370                         375                         380                                        |      |
| ttc ttc ctc gtg att tac ctc ttt tct cgc cta gcc gtt gag gcc gac                                                | 1200 |
| Phe Phe Leu Val Ile Tyr Leu Phe Ser Arg Leu Ala Val Glu Ala Asp                                                |      |
| 385                         390                         395                         400                        |      |
| cct cgc gcc cag aca gcc acg gtg att gtg agc acc acg gtt gca ttg                                                | 1248 |
| Pro Arg Ala Gln Thr Ala Thr Val Ile Val Ser Thr Thr Val Ala Leu                                                |      |
|             405                         410                         415                                        |      |
| att aag tgt ggg tat ttt tca ttc cga gcc aag gat att cgg gcg ttt                                                | 1296 |
| Ile Lys Cys Gly Tyr Phe Ser Phe Arg Ala Lys Asp Ile Arg Ala Phe                                                |      |
|             420                         425                         430                                        |      |
| tac ttt gtg ctt tat aca ttt gtt tac ttt ttc tgt atg att ccg gcc                                                | 1344 |
| Tyr Phe Val Leu Tyr Thr Phe Val Tyr Phe Phe Cys Met Ile Pro Ala                                                |      |
|             435                         440                         445                                        |      |
| agg att act gca atg atg acg ctt tgg gac att ggc tgg ggt act cgc                                                | 1392 |
| Arg Ile Thr Ala Met Met Thr Leu Trp Asp Ile Gly Trp Gly Thr Arg                                                |      |
| 450                         455                         460                                                    |      |
| ggt gga aac gag aag cct tcc gtt ggc acc cgg gtc gct ctg tgg gca                                                | 1440 |
| Gly Gly Asn Glu Lys Pro Ser Val Gly Thr Arg Val Ala Leu Trp Ala                                                |      |
| 465                         470                         475                         480                        |      |
| aag caa tat ctc att gca tat atg tgg tgg gcc gcg gtt gtt ggc gct                                                | 1488 |
| Lys Gln Tyr Leu Ile Ala Tyr Met Trp Trp Ala Ala Val Val Gly Ala                                                |      |
|             485                         490                         495                                        |      |
| gga gtt tac agc atc gtc cat aac tgg atg ttc gat tgg aat tct ctt                                                | 1536 |
| Gly Val Tyr Ser Ile Val His Asn Trp Met Phe Asp Trp Asn Ser Leu                                                |      |
|             500                         505                         510                                        |      |
| tct tat cgt ttt gct ttg gtt ggt att tgt tct tac att gtt ttt att                                                | 1584 |
| Ser Tyr Arg Phe Ala Leu Val Gly Ile Cys Ser Tyr Ile Val Phe Ile                                                |      |
|             515                         520                         525                                        |      |
| gtt att gtg ctg gtg gtt tat ttc acc ggc aaa att acg act tgg aat                                                | 1632 |
| Val Ile Val Leu Val Val Tyr Phe Thr Gly Lys Ile Thr Thr Trp Asn                                                |      |
|             530                         535                         540                                        |      |
| ttc acg aag ctt cag aag gag cta atc gag gat cgc gtt ctg tac gat                                                | 1680 |
| Phe Thr Lys Leu Gln Lys Glu Leu Ile Glu Asp Arg Val Leu Tyr Asp                                                |      |
| 545                         550                         555                         560                        |      |
| gca act acc aat gct cag tct gtg tga                                                                            | 1707 |

```
Ala Thr Thr Asn Ala Gln Ser Val
            565

<210> SEQ ID NO 2
<211> LENGTH: 568
<212> TYPE: PRT
<213> ORGANISM: Paramecium bursaria Chlorella Virus 1

<400> SEQUENCE: 2

Met Gly Lys Asn Ile Ile Met Val Ser Trp Tyr Thr Ile Ile Thr
1               5                   10                  15

Ser Asn Leu Ile Ala Val Gly Gly Ala Ser Leu Ile Leu Ala Pro Ala
                20                  25                  30

Ile Thr Gly Tyr Val Leu His Trp Asn Ile Ala Leu Ser Thr Ile Trp
            35                  40                  45

Gly Val Ser Ala Tyr Gly Ile Phe Val Phe Gly Phe Phe Leu Ala Gln
    50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ala
                85                  90                  95

Gly Tyr Arg Glu Asp Pro Tyr Met Phe Gln Lys Cys Leu Glu Ser Val
            100                 105                 110

Arg Asp Ser Asp Tyr Gly Asn Val Ala Arg Leu Ile Cys Val Ile Asp
        115                 120                 125

Gly Asp Glu Asp Asp Met Arg Met Ala Ala Val Tyr Lys Ala Ile
    130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Leu Ile Asp
        195                 200                 205

Ser Asp Thr Val Leu Glu Lys Asp Ala Ile Leu Glu Val Val Tyr Pro
    210                 215                 220

Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Arg Thr Val
            260                 265                 270

Gln Cys Val Gly Gly Pro Leu Gly Ala Tyr Lys Ile Asp Ile Ile Lys
        275                 280                 285

Glu Ile Lys Asp Pro Trp Ile Ser Gln Arg Phe Leu Gly Gln Lys Cys
    290                 295                 300

Thr Tyr Gly Asp Asp Arg Arg Leu Thr Asn Glu Ile Leu Met Arg Gly
305                 310                 315                 320

Lys Lys Val Val Phe Thr Pro Phe Ala Val Gly Trp Ser Asp Ser Pro
                325                 330                 335

Thr Asn Val Phe Arg Tyr Ile Val Gln Gln Thr Arg Trp Ser Lys Ser
            340                 345                 350

Trp Cys Arg Glu Ile Trp Tyr Thr Leu Phe Ala Ala Trp Lys His Gly
        355                 360                 365
```

```
Leu Ser Gly Ile Trp Leu Ala Phe Glu Cys Leu Tyr Gln Ile Thr Tyr
    370                 375                 380

Phe Phe Leu Val Ile Tyr Leu Phe Ser Arg Leu Ala Val Glu Ala Asp
385                 390                 395                 400

Pro Arg Ala Gln Thr Ala Thr Val Ile Val Ser Thr Thr Val Ala Leu
                405                 410                 415

Ile Lys Cys Gly Tyr Phe Ser Phe Arg Ala Lys Asp Ile Arg Ala Phe
                420                 425                 430

Tyr Phe Val Leu Tyr Thr Phe Val Tyr Phe Phe Cys Met Ile Pro Ala
                435                 440                 445

Arg Ile Thr Ala Met Met Thr Leu Trp Asp Ile Gly Trp Gly Thr Arg
            450                 455                 460

Gly Gly Asn Glu Lys Pro Ser Val Gly Thr Arg Val Ala Leu Trp Ala
465                 470                 475                 480

Lys Gln Tyr Leu Ile Ala Tyr Met Trp Trp Ala Ala Val Val Gly Ala
                485                 490                 495

Gly Val Tyr Ser Ile Val His Asn Trp Met Phe Asp Trp Asn Ser Leu
                500                 505                 510

Ser Tyr Arg Phe Ala Leu Val Gly Ile Cys Ser Tyr Ile Val Phe Ile
                515                 520                 525

Val Ile Val Leu Val Val Tyr Phe Thr Gly Lys Ile Thr Thr Trp Asn
            530                 535                 540

Phe Thr Lys Leu Gln Lys Glu Leu Ile Glu Asp Arg Val Leu Tyr Asp
545                 550                 555                 560

Ala Thr Thr Asn Ala Gln Ser Val
                565

<210> SEQ ID NO 3
<211> LENGTH: 1707
<212> TYPE: DNA
<213> ORGANISM: Artificial Seqeunce
<220> FEATURE:
<223> OTHER INFORMATION: Synthetic nucleotide sequence coding for a
      Paramecium bursaria Chlorella Virus 1 Hyaluronansynthase protein

<400> SEQUENCE: 3
atgggtaaga acattatcat tatggtgtcc tggtacacaa ttattacaag taatctcatc      60
gcagttggtg gtgcatctct tattctcgct ccagctatca ctggatatgt tcttcactgg     120
aacatcgccc tctcaactat ttggggagtt ccgcatatg gtattttgt tttcgggttc       180 tttttggctc aggttctgtt ctcagagctc aatcgtaaga gactcaggaa gtggattagc     240
cttagaccaa agggtggaa tgacgttcgt ctcgctgtca ttatcgctgg ctaccgtgaa      300
gatccttaca tgtttcaaaa gtgcttggaa tcagttaggg atagtgatta tggcaacgtc     360
gctagactga tctgtgtgat tgatggagat gaggacgacg atatgaggat ggcagctgtt    420
tataaggcta tctataatga taacattaag aagcctgaat tgttctttg cgagtctgat     480 gacaaggaag gagaacggat tgattcagat ttctcacgtg atatctgcgt tctccaacct    540
catcgtggga agcgtgaatg tctttataca ggtttccaac tcgccaaaat ggacccatca    600
gtgaacgctg tggttcttat cgatagtgat actgtgctgg agaaagatgc tatcttggag    660
gttgtttacc ctcttgcctg tgatcctgaa attcaagctg ggctggaga gtgcaagatc    720 tggaacacag atactcttct ttctctgctt gtcgcatgga gatattactc cgcattctgt    780
gtggagagga gcgctcaatc cttttttccgt accgttcaat gcgttggtgg tccttggga    840
```

-continued

```
gcttacaaaa ttgatatcat caaggagatt aaggacccat ggattagtca aaggtttctt    900
ggtcagaagt gcacttatgg cgatgatcgt agattgacta acgaaatcct tatgaggggc    960
aagaaagtcg tttttactcc atttgctgtc ggatggtctg attcacctac aaatgttttc   1020
cgttatattg tgcaacaaac acgttggagt aagagctggt gtagggagat ctggtacact   1080
ttgttcgctg cttggaagca cgggcttagc ggaatttggc ttgcttttga atgcctttac   1140
cagattacat actttttctt ggtgatctat ttgttttcac gtcttgccgt cgaggctgac   1200
cctagagcac agactgcaac tgtgattgtt tctactacag tcgcacttat taagtgtggc   1260
tatttcagtt ttagagcaaa agatattaga gccttctatt ttgttttgta cacatttgtt   1320
tatttctttt gcatgattcc agctcgtatt accgctatga tgaccttgtg ggacatcgga   1380
tggggaacta gaggtggtaa cgaaaagcct tctgtgggaa caagggtggc cctttgggca   1440
aaacaatatc tcatcgccta catgtggtgg gccgctgtcg ttggtgccgg agtgtactca   1500
atcgttcata actggatgtt tgactggaac tctttgagct atcgtttcgc tcttgtgggt   1560
atttgttctt acattgtttt catcgtgatt gtgctcgttg tgtatttcac tggtaaaatc   1620
acaacctgga atttcactaa acttcaaaag gaattgattg aagacagggt tctgtatgat   1680
gctactacca acgcccagtc agtttaa                                        1707
```

```

<210> SEQ ID NO 4
<211> LENGTH: 2895
<212> TYPE: DNA
<213> ORGANISM: Pasteurella multocida
<220> FEATURE:
<221> NAME/KEY: CDS
<222> LOCATION: (1)..(2895)
<300> PUBLICATION INFORMATION:
<308> DATABASE ACCESSION NUMBER: EMBL/AF195517
<309> DATABASE ENTRY DATE: 2000-09-07
<313> RELEVANT RESIDUES IN SEQ ID NO: (61)..(2955)

<400> SEQUENCE: 4 atg aat aca tta tca caa gca ata aaa gca tat aac agc aat gac tat      48
Met Asn Thr Leu Ser Gln Ala Ile Lys Ala Tyr Asn Ser Asn Asp Tyr
1               5                   10                  15 gaa tta gca ctc aaa tta ttt gag aag tct gct gaa acc tac ggg cga      96
Glu Leu Ala Leu Lys Leu Phe Glu Lys Ser Ala Glu Thr Tyr Gly Arg
            20                  25                  30 aaa atc gtt gaa ttc caa att atc aaa tgt aaa gaa aaa ctc tcg acc     144
Lys Ile Val Glu Phe Gln Ile Ile Lys Cys Lys Glu Lys Leu Ser Thr
        35                  40                  45 aat tct tat gta agt gaa gat aaa aaa aac agt gtt tgc gat agc tca     192
Asn Ser Tyr Val Ser Glu Asp Lys Lys Asn Ser Val Cys Asp Ser Ser
    50                  55                  60 tta gat atc gca aca cag ctc tta ctt tcc aac gta aaa aaa tta act     240
Leu Asp Ile Ala Thr Gln Leu Leu Leu Ser Asn Val Lys Lys Leu Thr
65                  70                  75                  80 cta tcc gaa tca gaa aaa aac agt tta aaa aat aaa tgg aaa tct atc     288
Leu Ser Glu Ser Glu Lys Asn Ser Leu Lys Asn Lys Trp Lys Ser Ile
                85                  90                  95 act ggg aaa aaa tcg gag aac gca gaa atc aga aag gtg gaa cta gta     336
Thr Gly Lys Lys Ser Glu Asn Ala Glu Ile Arg Lys Val Glu Leu Val
            100                 105                 110 ccc aaa gat ttt cct aaa gat ctt gtt ctt gct cca ttg cca gat cat     384
Pro Lys Asp Phe Pro Lys Asp Leu Val Leu Ala Pro Leu Pro Asp His
        115                 120                 125 gtt aat gat ttt aca tgg tac aaa aat cga aaa aaa agc tta ggt ata     432
Val Asn Asp Phe Thr Trp Tyr Lys Asn Arg Lys Lys Ser Leu Gly Ile
```

-continued

```
            130                 135                 140
aag cct gta aat aag aat atc ggt ctt tct att att att cct aca ttt        480
Lys Pro Val Asn Lys Asn Ile Gly Leu Ser Ile Ile Ile Pro Thr Phe
145                 150                 155                 160 aat cgt agc cgt att tta gat ata acg tta gcc tgt ttg gtc aat cag        528
Asn Arg Ser Arg Ile Leu Asp Ile Thr Leu Ala Cys Leu Val Asn Gln
                165                 170                 175 aaa aca aac tac cca ttt gaa gtc gtt gtt gca gat gat ggt agt aag        576
Lys Thr Asn Tyr Pro Phe Glu Val Val Val Ala Asp Asp Gly Ser Lys
            180                 185                 190 gaa aac tta ctt acc att gtg caa aaa tac gaa caa aaa ctt gac ata        624
Glu Asn Leu Leu Thr Ile Val Gln Lys Tyr Glu Gln Lys Leu Asp Ile
        195                 200                 205 aag tat gta aga caa aaa gat tat gga tat caa ttg tgt gca gtc aga        672
Lys Tyr Val Arg Gln Lys Asp Tyr Gly Tyr Gln Leu Cys Ala Val Arg
210                 215                 220 aac tta ggt tta cgt aca gca aag tat gat ttt gtc tcg att cta gac        720
Asn Leu Gly Leu Arg Thr Ala Lys Tyr Asp Phe Val Ser Ile Leu Asp
225                 230                 235                 240 tgc gat atg gca cca caa caa tta tgg gtt cat tct tat ctt aca gaa        768
Cys Asp Met Ala Pro Gln Gln Leu Trp Val His Ser Tyr Leu Thr Glu
                245                 250                 255 cta tta gaa gac aat gat att gtt tta att gga cct aga aaa tat gtg        816
Leu Leu Glu Asp Asn Asp Ile Val Leu Ile Gly Pro Arg Lys Tyr Val
            260                 265                 270 gat act cat aat att acc gca gaa caa ttc ctt aac gat cca tat tta        864
Asp Thr His Asn Ile Thr Ala Glu Gln Phe Leu Asn Asp Pro Tyr Leu
        275                 280                 285 ata gaa tca cta cct gaa acc gct aca aat aac aat cct tcg att aca        912
Ile Glu Ser Leu Pro Glu Thr Ala Thr Asn Asn Asn Pro Ser Ile Thr
290                 295                 300 tca aaa gga aat ata tcg ttg gat tgg aga tta gaa cat ttc aaa aaa        960
Ser Lys Gly Asn Ile Ser Leu Asp Trp Arg Leu Glu His Phe Lys Lys
305                 310                 315                 320 acc gat aat cta cgt cta tgt gat tct ccg ttt cgt tat ttt agt tgc       1008
Thr Asp Asn Leu Arg Leu Cys Asp Ser Pro Phe Arg Tyr Phe Ser Cys
                325                 330                 335 ggt aat gtt gca ttt tct aaa gaa tgg cta aat aaa gta ggt tgg ttc       1056
Gly Asn Val Ala Phe Ser Lys Glu Trp Leu Asn Lys Val Gly Trp Phe
            340                 345                 350 gat gaa gaa ttt aat cat tgg ggg ggc gaa gat gta gaa ttt ggt tac       1104
Asp Glu Glu Phe Asn His Trp Gly Gly Glu Asp Val Glu Phe Gly Tyr
        355                 360                 365 aga tta ttt gcc aaa ggc tgt ttt ttc aga gta att gac ggc gga atg       1152
Arg Leu Phe Ala Lys Gly Cys Phe Phe Arg Val Ile Asp Gly Gly Met
370                 375                 380 gca tac cat caa gaa cca cct ggt aaa gaa aat gaa aca gac cgc gaa       1200
Ala Tyr His Gln Glu Pro Pro Gly Lys Glu Asn Glu Thr Asp Arg Glu
385                 390                 395                 400 gct ggt aaa agt att acg ctt aaa att gtg aaa gaa aag gta cct tac       1248
Ala Gly Lys Ser Ile Thr Leu Lys Ile Val Lys Glu Lys Val Pro Tyr
                405                 410                 415 atc tat aga aag ctt tta cca ata gaa gat tca cat att cat aga ata       1296
Ile Tyr Arg Lys Leu Leu Pro Ile Glu Asp Ser His Ile His Arg Ile
            420                 425                 430 cct tta gtt tct att tat atc ccc gct tat aac tgt gca aat tat att       1344
Pro Leu Val Ser Ile Tyr Ile Pro Ala Tyr Asn Cys Ala Asn Tyr Ile
        435                 440                 445 caa aga tgt gta gat agt gct ctt aat caa act gtt gtc gat ctc gag       1392
Gln Arg Cys Val Asp Ser Ala Leu Asn Gln Thr Val Val Asp Leu Glu
```

```
Gln Arg Cys Val Asp Ser Ala Leu Asn Gln Thr Val Val Asp Leu Glu
    450             455                 460 gtt tgt att tgt aac gat ggt tca aca gat aat acc tta gaa gtg atc      1440
Val Cys Ile Cys Asn Asp Gly Ser Thr Asp Asn Thr Leu Glu Val Ile
465                 470                 475                 480 aat aag ctt tat ggt aat aat cct agg gta cgc atc atg tct aaa cca      1488
Asn Lys Leu Tyr Gly Asn Asn Pro Arg Val Arg Ile Met Ser Lys Pro
                    485                 490                 495 aat ggc gga ata gcc tca gca tca aat gca gcc gtt tct ttt gct aaa      1536
Asn Gly Gly Ile Ala Ser Ala Ser Asn Ala Ala Val Ser Phe Ala Lys
                500                 505                 510 ggt tat tac att ggg cag tta gat tca gat gat tat ctt gag cct gat      1584
Gly Tyr Tyr Ile Gly Gln Leu Asp Ser Asp Asp Tyr Leu Glu Pro Asp
            515                 520                 525 gca gtt gaa ctg tgt tta aaa gaa ttt tta aaa gat aaa acg cta gct      1632
Ala Val Glu Leu Cys Leu Lys Glu Phe Leu Lys Asp Lys Thr Leu Ala
        530                 535                 540 tgt gtt tat acc act aat aga aac gtc aat ccg gat ggt agc tta atc      1680
Cys Val Tyr Thr Thr Asn Arg Asn Val Asn Pro Asp Gly Ser Leu Ile
545                 550                 555                 560 gct aat ggt tac aat tgg cca gaa ttt tca cga gaa aaa ctc aca acg      1728
Ala Asn Gly Tyr Asn Trp Pro Glu Phe Ser Arg Glu Lys Leu Thr Thr
                565                 570                 575 gct atg att gct cac cat ttt aga atg ttt acg att aga gct tgg cat      1776
Ala Met Ile Ala His His Phe Arg Met Phe Thr Ile Arg Ala Trp His
                580                 585                 590 tta acg gat gga ttt aac gaa aat att gaa aac gcc gtg gat tat gac      1824
Leu Thr Asp Gly Phe Asn Glu Asn Ile Glu Asn Ala Val Asp Tyr Asp
            595                 600                 605 atg ttc ctt aaa ctc agt gaa gtt gga aaa ttt aaa cat ctt aat aaa      1872
Met Phe Leu Lys Leu Ser Glu Val Gly Lys Phe Lys His Leu Asn Lys
        610                 615                 620 atc tgc tat aac cgc gta tta cat ggt gat aac aca tcc att aag aaa      1920
Ile Cys Tyr Asn Arg Val Leu His Gly Asp Asn Thr Ser Ile Lys Lys
625                 630                 635                 640 ctc ggc att caa aag aaa aac cat ttt gtt gta gtc aat cag tca tta      1968
Leu Gly Ile Gln Lys Lys Asn His Phe Val Val Val Asn Gln Ser Leu
                645                 650                 655 aat aga caa ggc atc aat tat tat aat tat gac aaa ttt gat gat tta      2016
Asn Arg Gln Gly Ile Asn Tyr Tyr Asn Tyr Asp Lys Phe Asp Asp Leu
                660                 665                 670 gat gaa agt aga aag tat atc ttc aat aaa acc gct gaa tat caa gaa      2064
Asp Glu Ser Arg Lys Tyr Ile Phe Asn Lys Thr Ala Glu Tyr Gln Glu
            675                 680                 685 gaa atg gat att tta aaa gat ctt aaa ctc att caa aat aaa gat gcc      2112
Glu Met Asp Ile Leu Lys Asp Leu Lys Leu Ile Gln Asn Lys Asp Ala
        690                 695                 700 aaa atc gca gtc agt att ttc tat ccc aat aca tta aac ggc tta gtg      2160
Lys Ile Ala Val Ser Ile Phe Tyr Pro Asn Thr Leu Asn Gly Leu Val
705                 710                 715                 720 aaa aaa cta aac aat att att gaa tat aat aaa aat ata ttc gtt att      2208
Lys Lys Leu Asn Asn Ile Ile Glu Tyr Asn Lys Asn Ile Phe Val Ile
                725                 730                 735 att cta cat gtt gat aag aat cat ctt aca cca gac atc aaa aaa gaa      2256
Ile Leu His Val Asp Lys Asn His Leu Thr Pro Asp Ile Lys Lys Glu
                740                 745                 750 ata ttg gct ttc tat cat aag cac caa gtg aat att tta cta aat aat      2304
Ile Leu Ala Phe Tyr His Lys His Gln Val Asn Ile Leu Leu Asn Asn
            755                 760                 765
```

-continued

```
gac atc tca tat tac acg agt aat aga cta ata aaa act gag gca cat      2352
Asp Ile Ser Tyr Tyr Thr Ser Asn Arg Leu Ile Lys Thr Glu Ala His
    770                 775                 780 tta agt aat att aat aaa tta agt cag tta aat cta aat tgt gaa tac      2400
Leu Ser Asn Ile Asn Lys Leu Ser Gln Leu Asn Leu Asn Cys Glu Tyr
785                 790                 795                 800 atc att ttt gat aat cat gac agc cta ttc gtt aaa aat gac agc tat      2448
Ile Ile Phe Asp Asn His Asp Ser Leu Phe Val Lys Asn Asp Ser Tyr
                805                 810                 815 gct tat atg aaa aaa tat gat gtc ggc atg aat ttc tca gca tta aca      2496
Ala Tyr Met Lys Lys Tyr Asp Val Gly Met Asn Phe Ser Ala Leu Thr
            820                 825                 830 cat gat tgg atc gag aaa atc aat gcg cat cca cca ttt aaa aag ctg      2544
His Asp Trp Ile Glu Lys Ile Asn Ala His Pro Pro Phe Lys Lys Leu
        835                 840                 845 att aaa acc tat ttt aat gac aat gac tta aga agt atg aat gtg aaa      2592
Ile Lys Thr Tyr Phe Asn Asp Asn Asp Leu Arg Ser Met Asn Val Lys
    850                 855                 860 ggg gca tca caa ggt atg ttt atg aag tat gcg cta ccg cat gag ctt      2640
Gly Ala Ser Gln Gly Met Phe Met Lys Tyr Ala Leu Pro His Glu Leu
865                 870                 875                 880 ctg acg att att aaa gaa gtc atc aca tcc tgc caa tca att gat agt      2688
Leu Thr Ile Ile Lys Glu Val Ile Thr Ser Cys Gln Ser Ile Asp Ser
                885                 890                 895 gtg cca gaa tat aac act gag gat att tgg ttc caa ttt gca ctt tta      2736
Val Pro Glu Tyr Asn Thr Glu Asp Ile Trp Phe Gln Phe Ala Leu Leu
            900                 905                 910 atc tta gaa aag aaa acc ggc cat gta ttt aat aaa aca tcg acc ctg      2784
Ile Leu Glu Lys Lys Thr Gly His Val Phe Asn Lys Thr Ser Thr Leu
        915                 920                 925 act tat atg cct tgg gaa cga aaa tta caa tgg aca aat gaa caa att      2832
Thr Tyr Met Pro Trp Glu Arg Lys Leu Gln Trp Thr Asn Glu Gln Ile
    930                 935                 940 caa agt gca aaa aaa ggc gaa aat atc ccc gtt aac aag ttc att att      2880
Gln Ser Ala Lys Lys Gly Glu Asn Ile Pro Val Asn Lys Phe Ile Ile
945                 950                 955                 960 aat agt ata acg cta                                                  2895
Asn Ser Ile Thr Leu
                965

<210> SEQ ID NO 5
<211> LENGTH: 965
<212> TYPE: PRT
<213> ORGANISM: Pasteurella multocida

<400> SEQUENCE: 5

Met Asn Thr Leu Ser Gln Ala Ile Lys Ala Tyr Asn Ser Asn Asp Tyr
1               5                   10                  15

Glu Leu Ala Leu Lys Leu Phe Glu Lys Ser Ala Glu Thr Tyr Gly Arg
            20                  25                  30

Lys Ile Val Glu Phe Gln Ile Ile Lys Cys Lys Glu Lys Leu Ser Thr
        35                  40                  45

Asn Ser Tyr Val Ser Glu Asp Lys Lys Asn Ser Val Cys Asp Ser Ser
    50                  55                  60

Leu Asp Ile Ala Thr Gln Leu Leu Leu Ser Asn Val Lys Lys Leu Thr
65                  70                  75                  80

Leu Ser Glu Ser Glu Lys Asn Ser Leu Lys Asn Lys Trp Lys Ser Ile
                85                  90                  95

Thr Gly Lys Lys Ser Glu Asn Ala Glu Ile Arg Lys Val Glu Leu Val
```

```
                100                 105                 110
Pro Lys Asp Phe Pro Lys Asp Leu Val Leu Ala Pro Leu Pro Asp His
            115                 120                 125

Val Asn Asp Phe Thr Trp Tyr Lys Asn Arg Lys Lys Ser Leu Gly Ile
130                 135                 140

Lys Pro Val Asn Lys Asn Ile Gly Leu Ser Ile Ile Pro Thr Phe
145                 150                 155                 160

Asn Arg Ser Arg Ile Leu Asp Ile Thr Leu Ala Cys Leu Val Asn Gln
                165                 170                 175

Lys Thr Asn Tyr Pro Phe Glu Val Val Ala Asp Asp Gly Ser Lys
            180                 185                 190

Glu Asn Leu Leu Thr Ile Val Gln Lys Tyr Glu Gln Lys Leu Asp Ile
            195                 200                 205

Lys Tyr Val Arg Gln Lys Asp Tyr Gly Tyr Gln Leu Cys Ala Val Arg
210                 215                 220

Asn Leu Gly Leu Arg Thr Ala Lys Tyr Asp Phe Val Ser Ile Leu Asp
225                 230                 235                 240

Cys Asp Met Ala Pro Gln Gln Leu Trp Val His Ser Tyr Leu Thr Glu
                245                 250                 255

Leu Leu Glu Asp Asn Asp Ile Val Leu Ile Gly Pro Arg Lys Tyr Val
            260                 265                 270

Asp Thr His Asn Ile Thr Ala Glu Gln Phe Leu Asn Asp Pro Tyr Leu
            275                 280                 285

Ile Glu Ser Leu Pro Glu Thr Ala Thr Asn Asn Asn Pro Ser Ile Thr
            290                 295                 300

Ser Lys Gly Asn Ile Ser Leu Asp Trp Arg Leu Glu His Phe Lys Lys
305                 310                 315                 320

Thr Asp Asn Leu Arg Leu Cys Asp Ser Pro Phe Arg Tyr Phe Ser Cys
                325                 330                 335

Gly Asn Val Ala Phe Ser Lys Glu Trp Leu Asn Lys Val Gly Trp Phe
            340                 345                 350

Asp Glu Glu Phe Asn His Trp Gly Gly Glu Asp Val Glu Phe Gly Tyr
            355                 360                 365

Arg Leu Phe Ala Lys Gly Cys Phe Phe Arg Val Ile Asp Gly Gly Met
370                 375                 380

Ala Tyr His Gln Glu Pro Pro Gly Lys Glu Asn Glu Thr Asp Arg Glu
385                 390                 395                 400

Ala Gly Lys Ser Ile Thr Leu Lys Ile Val Lys Glu Lys Val Pro Tyr
                405                 410                 415

Ile Tyr Arg Lys Leu Leu Pro Ile Glu Asp Ser His Ile His Arg Ile
            420                 425                 430

Pro Leu Val Ser Ile Tyr Ile Pro Ala Tyr Asn Cys Ala Asn Tyr Ile
            435                 440                 445

Gln Arg Cys Val Asp Ser Ala Leu Asn Gln Thr Val Val Asp Leu Glu
450                 455                 460

Val Cys Ile Cys Asn Asp Gly Ser Thr Asp Asn Thr Leu Glu Val Ile
465                 470                 475                 480

Asn Lys Leu Tyr Gly Asn Asn Pro Arg Val Arg Ile Met Ser Lys Pro
                485                 490                 495

Asn Gly Gly Ile Ala Ser Ala Ser Asn Ala Ala Val Ser Phe Ala Lys
            500                 505                 510

Gly Tyr Tyr Ile Gly Gln Leu Asp Ser Asp Asp Tyr Leu Glu Pro Asp
            515                 520                 525
```

```
Ala Val Glu Leu Cys Leu Lys Glu Phe Leu Lys Asp Lys Thr Leu Ala
        530                 535                 540

Cys Val Tyr Thr Thr Asn Arg Asn Val Asn Pro Asp Gly Ser Leu Ile
545                 550                 555                 560

Ala Asn Gly Tyr Asn Trp Pro Glu Phe Ser Arg Glu Lys Leu Thr Thr
                565                 570                 575

Ala Met Ile Ala His His Phe Arg Met Phe Thr Ile Arg Ala Trp His
            580                 585                 590

Leu Thr Asp Gly Phe Asn Glu Asn Ile Glu Asn Ala Val Asp Tyr Asp
        595                 600                 605

Met Phe Leu Lys Leu Ser Glu Val Gly Lys Phe Lys His Leu Asn Lys
    610                 615                 620

Ile Cys Tyr Asn Arg Val Leu His Gly Asp Asn Thr Ser Ile Lys Lys
625                 630                 635                 640

Leu Gly Ile Gln Lys Lys Asn His Phe Val Val Asn Gln Ser Leu
                645                 650                 655

Asn Arg Gln Gly Ile Asn Tyr Tyr Asn Tyr Asp Lys Phe Asp Asp Leu
                660                 665                 670

Asp Glu Ser Arg Lys Tyr Ile Phe Asn Lys Thr Ala Glu Tyr Gln Glu
            675                 680                 685

Glu Met Asp Ile Leu Lys Asp Leu Lys Leu Ile Gln Asn Lys Asp Ala
    690                 695                 700

Lys Ile Ala Val Ser Ile Phe Tyr Pro Asn Thr Leu Asn Gly Leu Val
705                 710                 715                 720

Lys Lys Leu Asn Asn Ile Ile Glu Tyr Asn Lys Asn Ile Phe Val Ile
                725                 730                 735

Ile Leu His Val Asp Lys Asn His Leu Thr Pro Asp Ile Lys Lys Glu
                740                 745                 750

Ile Leu Ala Phe Tyr His Lys His Gln Val Asn Ile Leu Leu Asn Asn
            755                 760                 765

Asp Ile Ser Tyr Tyr Thr Ser Asn Arg Leu Ile Lys Thr Glu Ala His
        770                 775                 780

Leu Ser Asn Ile Asn Lys Leu Ser Gln Leu Asn Leu Asn Cys Glu Tyr
785                 790                 795                 800

Ile Ile Phe Asp Asn His Asp Ser Leu Phe Val Lys Asn Asp Ser Tyr
                805                 810                 815

Ala Tyr Met Lys Lys Tyr Asp Val Gly Met Asn Phe Ser Ala Leu Thr
                820                 825                 830

His Asp Trp Ile Glu Lys Ile Asn Ala His Pro Pro Phe Lys Lys Leu
            835                 840                 845

Ile Lys Thr Tyr Phe Asn Asp Asn Asp Leu Arg Ser Met Asn Val Lys
        850                 855                 860

Gly Ala Ser Gln Gly Met Phe Met Lys Tyr Ala Leu Pro His Glu Leu
865                 870                 875                 880

Leu Thr Ile Ile Lys Glu Val Ile Thr Ser Cys Gln Ser Ile Asp Ser
                885                 890                 895

Val Pro Glu Tyr Asn Thr Glu Asp Ile Trp Phe Gln Phe Ala Leu Leu
            900                 905                 910

Ile Leu Glu Lys Lys Thr Gly His Val Phe Asn Lys Thr Ser Thr Leu
        915                 920                 925

Thr Tyr Met Pro Trp Glu Arg Lys Leu Gln Trp Thr Asn Glu Gln Ile
    930                 935                 940
```

```
Gln Ser Ala Lys Lys Gly Glu Asn Ile Pro Val Asn Lys Phe Ile Ile
945                 950                 955                 960

Asn Ser Ile Thr Leu
            965

<210> SEQ ID NO 6
<211> LENGTH: 1953
<212> TYPE: DNA
<213> ORGANISM: Pasteurella multocida
<220> FEATURE:
<221> NAME/KEY: CDS
<222> LOCATION: (1)..(1953)
<300> PUBLICATION INFORMATION:
<308> DATABASE ACCESSION NUMBER: EMBL/AY292199
<309> DATABASE ENTRY DATE: 2004-11-25
<313> RELEVANT RESIDUES IN SEQ ID NO: (1)..(1953)

<400> SEQUENCE: 6 atg aag gga aaa aaa gag atg act caa att caa ata gct aaa aat cca      48
Met Lys Gly Lys Lys Glu Met Thr Gln Ile Gln Ile Ala Lys Asn Pro
1               5                   10                  15 ccc caa cat gaa aaa gaa aat gaa ctc aac acc ttt caa aat aaa att      96
Pro Gln His Glu Lys Glu Asn Glu Leu Asn Thr Phe Gln Asn Lys Ile
            20                  25                  30 gat agt cta aaa aca act tta aac aaa gac att att tct caa caa act     144
Asp Ser Leu Lys Thr Thr Leu Asn Lys Asp Ile Ile Ser Gln Gln Thr
        35                  40                  45 cta ttg gca aaa cag gac agt aaa cat ccg cta tcc gca tcc ctt gaa     192
Leu Leu Ala Lys Gln Asp Ser Lys His Pro Leu Ser Ala Ser Leu Glu
    50                  55                  60 aac gaa aat aaa ctt tta tta aaa caa ctc caa ttg gtt ctg caa gaa     240
Asn Glu Asn Lys Leu Leu Leu Lys Gln Leu Gln Leu Val Leu Gln Glu
65                  70                  75                  80 ttt aaa aaa ata tat acc tat aat caa gca tta gaa gca aag cta gaa     288
Phe Lys Lys Ile Tyr Thr Tyr Asn Gln Ala Leu Glu Ala Lys Leu Glu
                85                  90                  95 aaa gat aag caa aca aca tca ata aca gat tta tat aat gaa gtc gct     336
Lys Asp Lys Gln Thr Thr Ser Ile Thr Asp Leu Tyr Asn Glu Val Ala
            100                 105                 110 aaa agt gat tta ggg tta gtc aaa gaa acc aac agc gca aat cca tta     384
Lys Ser Asp Leu Gly Leu Val Lys Glu Thr Asn Ser Ala Asn Pro Leu
        115                 120                 125 gtc agt att atc atg aca tct cac aat aca gcg caa ttt atc gaa gct     432
Val Ser Ile Ile Met Thr Ser His Asn Thr Ala Gln Phe Ile Glu Ala
    130                 135                 140 tct att aat tca tta ttg tta caa aca tat aaa aac ata gaa att att     480
Ser Ile Asn Ser Leu Leu Leu Gln Thr Tyr Lys Asn Ile Glu Ile Ile
145                 150                 155                 160 att gta gat gat gat agc tcg gat aat aca ttt gaa att gcc tcg aga     528
Ile Val Asp Asp Asp Ser Ser Asp Asn Thr Phe Glu Ile Ala Ser Arg
                165                 170                 175 ata gcg aat aca aca agc aaa gtc aga gta ttt aga tta aat tca aac     576
Ile Ala Asn Thr Thr Ser Lys Val Arg Val Phe Arg Leu Asn Ser Asn
            180                 185                 190 cta gga act tac ttt gcg aaa aat aca ggc ata tta aaa tct aaa ggt     624
Leu Gly Thr Tyr Phe Ala Lys Asn Thr Gly Ile Leu Lys Ser Lys Gly
        195                 200                 205 gac att att ttc ttt caa gat agt gat gat gta tgt cat cat gaa aga     672
Asp Ile Ile Phe Phe Gln Asp Ser Asp Asp Val Cys His His Glu Arg
    210                 215                 220 ata gaa aga tgt gta aat ata tta tta gct aat aaa gaa act att gct     720
Ile Glu Arg Cys Val Asn Ile Leu Leu Ala Asn Lys Glu Thr Ile Ala
```

```
                                    -continued
   225                230                235                240
gtt cgt tgt gca tac tca aga cta gca cca gaa aca cag cat atc att      768
Val Arg Cys Ala Tyr Ser Arg Leu Ala Pro Glu Thr Gln His Ile Ile
                245                250                255 aaa gtc aat aat atg gat tat aga tta ggt ttt ata acc ttg ggt atg      816
Lys Val Asn Asn Met Asp Tyr Arg Leu Gly Phe Ile Thr Leu Gly Met
                260                265                270 cac aaa aaa gta ttt caa gaa att ggt ttc ttc aat tgt acg act aaa      864
His Lys Lys Val Phe Gln Glu Ile Gly Phe Phe Asn Cys Thr Thr Lys
            275                280                285 ggc tca gat gat gag ttt ttt cat aga att gcg aaa tat tat gga aaa      912
Gly Ser Asp Asp Glu Phe Phe His Arg Ile Ala Lys Tyr Tyr Gly Lys
        290                295                300 gaa aaa ata aaa aat tta ctc ttg ccg tta tac tac aac aca atg aga      960
Glu Lys Ile Lys Asn Leu Leu Leu Pro Leu Tyr Tyr Asn Thr Met Arg
305                310                315                320 gaa aac tct tta ttt act gat atg gtt gaa tgg ata gac aat cat aac     1008
Glu Asn Ser Leu Phe Thr Asp Met Val Glu Trp Ile Asp Asn His Asn
                325                330                335 ata ata cag aaa atg tct gat acc aga caa cat tat gca acc ctg ttt     1056
Ile Ile Gln Lys Met Ser Asp Thr Arg Gln His Tyr Ala Thr Leu Phe
                340                345                350 caa gcg atg cat aac gaa act gcc tca cat gat ttc aaa aat ctt ttt     1104
Gln Ala Met His Asn Glu Thr Ala Ser His Asp Phe Lys Asn Leu Phe
            355                360                365 caa ttc cct cgt att tac gac gcc tta cca gta cca caa gaa atg agt     1152
Gln Phe Pro Arg Ile Tyr Asp Ala Leu Pro Val Pro Gln Glu Met Ser
        370                375                380 aag ttg tcc aat cct aag att cct gtt tat atc aat att tgt tct att     1200
Lys Leu Ser Asn Pro Lys Ile Pro Val Tyr Ile Asn Ile Cys Ser Ile
385                390                395                400 ccc tca aga ata gcg caa tta caa cgt att atc ggc ata cta aaa aat     1248
Pro Ser Arg Ile Ala Gln Leu Gln Arg Ile Ile Gly Ile Leu Lys Asn
                405                410                415 caa tgt gat cat ttt cat att tat ctt gat ggc tat gta gaa atc cct     1296
Gln Cys Asp His Phe His Ile Tyr Leu Asp Gly Tyr Val Glu Ile Pro
                420                425                430 gac ttc ata aaa aat tta ggt aat aaa gca acc gtt gtt cat tgc aaa     1344
Asp Phe Ile Lys Asn Leu Gly Asn Lys Ala Thr Val Val His Cys Lys
            435                440                445 gat aaa gat aac tcc att aga gat aat ggc aaa ttc att tta ctg gaa     1392
Asp Lys Asp Asn Ser Ile Arg Asp Asn Gly Lys Phe Ile Leu Leu Glu
        450                455                460 gag ttg att gaa aaa aat caa gat gga tat tat ata acc tgt gat gat     1440
Glu Leu Ile Glu Lys Asn Gln Asp Gly Tyr Tyr Ile Thr Cys Asp Asp
465                470                475                480 gac att atc tat cca agc gat tac atc aat acg atg atc aag aag ctg     1488
Asp Ile Ile Tyr Pro Ser Asp Tyr Ile Asn Thr Met Ile Lys Lys Leu
                485                490                495 aat gaa tac gat gat aaa gcg gtt att ggt tta cac ggc att ctc ttt     1536
Asn Glu Tyr Asp Asp Lys Ala Val Ile Gly Leu His Gly Ile Leu Phe
                500                505                510 cca agt aga atg acc aaa tat ttt tcg gcg gat aga ctg gta tat agc     1584
Pro Ser Arg Met Thr Lys Tyr Phe Ser Ala Asp Arg Leu Val Tyr Ser
            515                520                525 ttc tat aaa cct ctg gaa aaa gac aaa gcg gtc aat gta tta ggt aca     1632
Phe Tyr Lys Pro Leu Glu Lys Asp Lys Ala Val Asn Val Leu Gly Thr
        530                535                540 gga act gtt agc ttt aga gtc agt ctc ttt aat caa ttt tct ctt tct     1680
```

```
Gly Thr Val Ser Phe Arg Val Ser Leu Phe Asn Gln Phe Ser Leu Ser
545                 550                 555                 560 gac ttt acc cat tca ggc atg gct gat atc tat ttc tct ctc ttg tgt      1728
Asp Phe Thr His Ser Gly Met Ala Asp Ile Tyr Phe Ser Leu Leu Cys
                565                 570                 575 aag aaa aat aat att ctt cag att tgt att tca aga cca gca aac tgg      1776
Lys Lys Asn Asn Ile Leu Gln Ile Cys Ile Ser Arg Pro Ala Asn Trp
                580                 585                 590 cta acg gaa gat aat aga gac agc gaa aca ctc tat cat caa tat cga      1824
Leu Thr Glu Asp Asn Arg Asp Ser Glu Thr Leu Tyr His Gln Tyr Arg
                595                 600                 605 gac aat gat gag caa caa act cag ctg atc atg gaa aac ggt cca tgg      1872
Asp Asn Asp Glu Gln Gln Thr Gln Leu Ile Met Glu Asn Gly Pro Trp
610                 615                 620 gga tat tca agt att tat cca tta gtc aaa aat cat cct aaa ttt act      1920
Gly Tyr Ser Ser Ile Tyr Pro Leu Val Lys Asn His Pro Lys Phe Thr
625                 630                 635                 640 gac ctt atc ccc tgt tta cct ttt tat ttt tta                          1953
Asp Leu Ile Pro Cys Leu Pro Phe Tyr Phe Leu
                645                 650

<210> SEQ ID NO 7
<211> LENGTH: 651
<212> TYPE: PRT
<213> ORGANISM: Pasteurella multocida

<400> SEQUENCE: 7

Met Lys Gly Lys Lys Glu Met Thr Gln Ile Gln Ile Ala Lys Asn Pro
1               5                   10                  15

Pro Gln His Glu Lys Glu Asn Glu Leu Asn Thr Phe Gln Asn Lys Ile
                20                  25                  30

Asp Ser Leu Lys Thr Thr Leu Asn Lys Asp Ile Ile Ser Gln Gln Thr
            35                  40                  45

Leu Leu Ala Lys Gln Asp Ser Lys His Pro Leu Ser Ala Ser Leu Glu
        50                  55                  60

Asn Glu Asn Lys Leu Leu Leu Lys Gln Leu Gln Leu Val Leu Gln Glu
65                  70                  75                  80

Phe Lys Lys Ile Tyr Thr Tyr Asn Gln Ala Leu Glu Ala Lys Leu Glu
                85                  90                  95

Lys Asp Lys Gln Thr Thr Ser Ile Thr Asp Leu Tyr Asn Glu Val Ala
            100                 105                 110

Lys Ser Asp Leu Gly Leu Val Lys Glu Thr Asn Ser Ala Asn Pro Leu
        115                 120                 125

Val Ser Ile Ile Met Thr Ser His Asn Thr Ala Gln Phe Ile Glu Ala
    130                 135                 140

Ser Ile Asn Ser Leu Leu Leu Gln Thr Tyr Lys Asn Ile Glu Ile Ile
145                 150                 155                 160

Ile Val Asp Asp Ser Ser Asp Asn Thr Phe Glu Ile Ala Ser Arg
                165                 170                 175

Ile Ala Asn Thr Thr Ser Lys Val Arg Val Phe Arg Leu Asn Ser Asn
            180                 185                 190

Leu Gly Thr Tyr Phe Ala Lys Asn Thr Gly Ile Leu Lys Ser Lys Gly
        195                 200                 205

Asp Ile Ile Phe Phe Gln Asp Ser Asp Asp Val Cys His His Glu Arg
    210                 215                 220

Ile Glu Arg Cys Val Asn Ile Leu Leu Ala Asn Lys Glu Thr Ile Ala
225                 230                 235                 240
```

```
Val Arg Cys Ala Tyr Ser Arg Leu Ala Pro Glu Thr Gln His Ile Ile
                245                 250                 255

Lys Val Asn Asn Met Asp Tyr Arg Leu Gly Phe Ile Thr Leu Gly Met
            260                 265                 270

His Lys Lys Val Phe Gln Glu Ile Gly Phe Phe Asn Cys Thr Thr Lys
        275                 280                 285

Gly Ser Asp Asp Glu Phe Phe His Arg Ile Ala Lys Tyr Tyr Gly Lys
    290                 295                 300

Glu Lys Ile Lys Asn Leu Leu Leu Pro Leu Tyr Tyr Asn Thr Met Arg
305                 310                 315                 320

Glu Asn Ser Leu Phe Thr Asp Met Val Glu Trp Ile Asp Asn His Asn
                325                 330                 335

Ile Ile Gln Lys Met Ser Asp Thr Arg Gln His Tyr Ala Thr Leu Phe
            340                 345                 350

Gln Ala Met His Asn Glu Thr Ala Ser His Asp Phe Lys Asn Leu Phe
        355                 360                 365

Gln Phe Pro Arg Ile Tyr Asp Ala Leu Pro Val Pro Gln Glu Met Ser
    370                 375                 380

Lys Leu Ser Asn Pro Lys Ile Pro Val Tyr Ile Asn Ile Cys Ser Ile
385                 390                 395                 400

Pro Ser Arg Ile Ala Gln Leu Gln Arg Ile Ile Gly Ile Leu Lys Asn
                405                 410                 415

Gln Cys Asp His Phe His Ile Tyr Leu Asp Gly Tyr Val Glu Ile Pro
            420                 425                 430

Asp Phe Ile Lys Asn Leu Gly Asn Lys Ala Thr Val Val His Cys Lys
        435                 440                 445

Asp Lys Asp Asn Ser Ile Arg Asp Asn Gly Lys Phe Ile Leu Leu Glu
    450                 455                 460

Glu Leu Ile Glu Lys Asn Gln Asp Gly Tyr Tyr Ile Thr Cys Asp Asp
465                 470                 475                 480

Asp Ile Ile Tyr Pro Ser Asp Tyr Ile Asn Thr Met Ile Lys Lys Leu
                485                 490                 495

Asn Glu Tyr Asp Asp Lys Ala Val Ile Gly Leu His Gly Ile Leu Phe
            500                 505                 510

Pro Ser Arg Met Thr Lys Tyr Phe Ser Ala Asp Arg Leu Val Tyr Ser
        515                 520                 525

Phe Tyr Lys Pro Leu Glu Lys Asp Lys Ala Val Asn Val Leu Gly Thr
    530                 535                 540

Gly Thr Val Ser Phe Arg Val Ser Leu Phe Asn Gln Phe Ser Leu Ser
545                 550                 555                 560

Asp Phe Thr His Ser Gly Met Ala Asp Ile Tyr Phe Ser Leu Leu Cys
                565                 570                 575

Lys Lys Asn Asn Ile Leu Gln Ile Cys Ile Ser Arg Pro Ala Asn Trp
            580                 585                 590

Leu Thr Glu Asp Asn Arg Asp Ser Glu Thr Leu Tyr His Gln Tyr Arg
        595                 600                 605

Asp Asn Asp Glu Gln Gln Thr Gln Leu Ile Met Glu Asn Gly Pro Trp
    610                 615                 620

Gly Tyr Ser Ser Ile Tyr Pro Leu Val Lys Asn His Pro Lys Phe Thr
625                 630                 635                 640

Asp Leu Ile Pro Cys Leu Pro Phe Tyr Phe Leu
                645                 650
```

<210> SEQ ID NO 8
<211> LENGTH: 480
<212> TYPE: DNA
<213> ORGANISM: Saccharomyces cerevisiae
<220> FEATURE:
<221> NAME/KEY: CDS
<222> LOCATION: (1)..(477)
<300> PUBLICATION INFORMATION:
<308> DATABASE ACCESSION NUMBER: GenBanh/AY558564
<309> DATABASE ENTRY DATE: 2007-04-24
<313> RELEVANT RESIDUES IN SEQ ID NO: (1)..(477)

<400> SEQUENCE: 8

```
atg agc tta ccc gat gga ttt tat ata agg cga atg gaa gag ggg gat     48
Met Ser Leu Pro Asp Gly Phe Tyr Ile Arg Arg Met Glu Glu Gly Asp
1               5                   10                  15 ttg gaa cag gtc act gag acg cta aag gtt ttg acc acc gtg ggc act     96
Leu Glu Gln Val Thr Glu Thr Leu Lys Val Leu Thr Thr Val Gly Thr
            20                  25                  30 att acc ccc gaa tcc ttc agc aaa ctc ata aaa tac tgg aat gaa gcc    144
Ile Thr Pro Glu Ser Phe Ser Lys Leu Ile Lys Tyr Trp Asn Glu Ala
        35                  40                  45 aca gta tgg aat gat aac gaa gat aaa aaa ata atg caa tat aac ccc    192
Thr Val Trp Asn Asp Asn Glu Asp Lys Lys Ile Met Gln Tyr Asn Pro
    50                  55                  60 atg gtg att gtg gac aag cgc acc gag acg gtt gcc gct acg ggg aat    240
Met Val Ile Val Asp Lys Arg Thr Glu Thr Val Ala Ala Thr Gly Asn
65                  70                  75                  80 atc atc atc gaa aga aag atc att cat gaa ctg ggg cta tgt ggc cac    288
Ile Ile Ile Glu Arg Lys Ile Ile His Glu Leu Gly Leu Cys Gly His
                85                  90                  95 atc gag gac att gca gta aac tcc aag tat cag ggc caa ggt ttg ggc    336
Ile Glu Asp Ile Ala Val Asn Ser Lys Tyr Gln Gly Gln Gly Leu Gly
            100                 105                 110 aag ctc ttg att gat caa ttg gta act atc ggc ttt gac tac ggt tgt    384
Lys Leu Leu Ile Asp Gln Leu Val Thr Ile Gly Phe Asp Tyr Gly Cys
        115                 120                 125 tat aag att att tta gat tgc gat gag aaa aat gtc aaa ttc tat gaa    432
Tyr Lys Ile Ile Leu Asp Cys Asp Glu Lys Asn Val Lys Phe Tyr Glu
    130                 135                 140 aaa tgt ggg ttt agc aac gca ggc gtg gaa atg caa att aga aaa tag    480
Lys Cys Gly Phe Ser Asn Ala Gly Val Glu Met Gln Ile Arg Lys
145                 150                 155
```

<210> SEQ ID NO 9
<211> LENGTH: 159
<212> TYPE: PRT
<213> ORGANISM: Saccharomyces cerevisiae

<400> SEQUENCE: 9

```
Met Ser Leu Pro Asp Gly Phe Tyr Ile Arg Arg Met Glu Glu Gly Asp
1               5                   10                  15

Leu Glu Gln Val Thr Glu Thr Leu Lys Val Leu Thr Thr Val Gly Thr
            20                  25                  30

Ile Thr Pro Glu Ser Phe Ser Lys Leu Ile Lys Tyr Trp Asn Glu Ala
        35                  40                  45

Thr Val Trp Asn Asp Asn Glu Asp Lys Lys Ile Met Gln Tyr Asn Pro
    50                  55                  60

Met Val Ile Val Asp Lys Arg Thr Glu Thr Val Ala Ala Thr Gly Asn
65                  70                  75                  80

Ile Ile Ile Glu Arg Lys Ile Ile His Glu Leu Gly Leu Cys Gly His
```

```
                    85                  90                  95
Ile Glu Asp Ile Ala Val Asn Ser Lys Tyr Gln Gly Gln Gly Leu Gly
                100                 105                 110

Lys Leu Leu Ile Asp Gln Leu Val Thr Ile Gly Phe Asp Tyr Gly Cys
            115                 120                 125

Tyr Lys Ile Ile Leu Asp Cys Asp Glu Lys Asn Val Lys Phe Tyr Glu
        130                 135                 140

Lys Cys Gly Phe Ser Asn Ala Gly Val Glu Met Gln Ile Arg Lys
145                 150                 155

<210> SEQ ID NO 10
<211> LENGTH: 1434
<212> TYPE: DNA
<213> ORGANISM: Saccharomyces cerevisiae
<220> FEATURE:
<221> NAME/KEY: CDS
<222> LOCATION: (1)..(1431)
<300> PUBLICATION INFORMATION:
<308> DATABASE ACCESSION NUMBER: GenBank/X79380
<309> DATABASE ENTRY DATE: 2005-04-18
<313> RELEVANT RESIDUES IN SEQ ID NO: (3261)..(4694)

<400> SEQUENCE: 10 atg act gac aca aaa cag cta ttc att gaa gcc gga caa agt caa ctt      48
Met Thr Asp Thr Lys Gln Leu Phe Ile Glu Ala Gly Gln Ser Gln Leu
1               5                   10                  15 ttc cac aat tgg gaa agc ttg tct cgc aaa gac caa gaa gaa ttg ctt      96
Phe His Asn Trp Glu Ser Leu Ser Arg Lys Asp Gln Glu Glu Leu Leu
                20                  25                  30 tca aac ctg gag caa ata tct tcc aag agg tcc cct gca aaa cta ctg     144
Ser Asn Leu Glu Gln Ile Ser Ser Lys Arg Ser Pro Ala Lys Leu Leu
            35                  40                  45 gaa gac tgt caa aat gct att aaa ttc tca cta gct aac tct tct aag     192
Glu Asp Cys Gln Asn Ala Ile Lys Phe Ser Leu Ala Asn Ser Ser Lys
        50                  55                  60 gat act ggc gtc gaa att tca cca ttg ccc cct act tcg tac gag tcg     240
Asp Thr Gly Val Glu Ile Ser Pro Leu Pro Pro Thr Ser Tyr Glu Ser
65                  70                  75                  80 ctt att ggc aac agt aag aaa gaa aat gaa tac tgg cgt tta ggc ctt     288
Leu Ile Gly Asn Ser Lys Lys Glu Asn Glu Tyr Trp Arg Leu Gly Leu
                85                  90                  95 gaa gct att ggc aag ggt gaa gtc gca gtg att tta atg gct ggc gga     336
Glu Ala Ile Gly Lys Gly Glu Val Ala Val Ile Leu Met Ala Gly Gly
                100                 105                 110 caa ggt acg cgg tta gga tcc tct caa cca aag ggc tgt tac gac att     384
Gln Gly Thr Arg Leu Gly Ser Ser Gln Pro Lys Gly Cys Tyr Asp Ile
            115                 120                 125 gga ttg cct tct aag aaa tct ctt ttt caa att caa gct gaa aag ttg     432
Gly Leu Pro Ser Lys Lys Ser Leu Phe Gln Ile Gln Ala Glu Lys Leu
        130                 135                 140 atc agg ttg caa gat atg gta aag gac aaa aag gta gaa att cct tgg     480
Ile Arg Leu Gln Asp Met Val Lys Asp Lys Lys Val Glu Ile Pro Trp
145                 150                 155                 160 tat att atg aca tca ggc ccc act aga gcg gct act gag gca tac ttt     528
Tyr Ile Met Thr Ser Gly Pro Thr Arg Ala Ala Thr Glu Ala Tyr Phe
                165                 170                 175 caa gaa cac aat tat ttt ggc ttg aat aaa gaa caa att acg ttc ttc     576
Gln Glu His Asn Tyr Phe Gly Leu Asn Lys Glu Gln Ile Thr Phe Phe
                180                 185                 190 aac cag gga acc ctg cct gcc ttt gat tta acc ggg aag cat ttc cta     624
Asn Gln Gly Thr Leu Pro Ala Phe Asp Leu Thr Gly Lys His Phe Leu
```

```
            195                 200                 205
atg aaa gac cca gta aac cta tct caa tca cca gat gga aat ggt gga      672
Met Lys Asp Pro Val Asn Leu Ser Gln Ser Pro Asp Gly Asn Gly Gly
    210                 215                 220 ctc tac cgt gcc atc aag gaa aac aag ttg aac gaa gac ttt gat agg      720
Leu Tyr Arg Ala Ile Lys Glu Asn Lys Leu Asn Glu Asp Phe Asp Arg
225                 230                 235                 240 aga gga atc aag cat gtt tac atg tac tgt gtc gat aat gtc cta tct      768
Arg Gly Ile Lys His Val Tyr Met Tyr Cys Val Asp Asn Val Leu Ser
                245                 250                 255 aaa atc gca gac cct gta ttt att ggt ttt gcc atc aag cat ggc ttc      816
Lys Ile Ala Asp Pro Val Phe Ile Gly Phe Ala Ile Lys His Gly Phe
            260                 265                 270 gaa ctg gcc acc aaa gcc gtt aga aag aga gat gcg cat gaa tca gtt      864
Glu Leu Ala Thr Lys Ala Val Arg Lys Arg Asp Ala His Glu Ser Val
        275                 280                 285 ggg tta att gct act aaa aac gag aaa cca tgt gtc ata gaa tat tct      912
Gly Leu Ile Ala Thr Lys Asn Glu Lys Pro Cys Val Ile Glu Tyr Ser
    290                 295                 300 gaa att tcc aat gaa ttg gct gaa gca aag gat aaa gat ggc tta tta      960
Glu Ile Ser Asn Glu Leu Ala Glu Ala Lys Asp Lys Asp Gly Leu Leu
305                 310                 315                 320 aaa cta cgc gca ggc aac att gta aat cat tat tac cta gtg gat tta     1008
Lys Leu Arg Ala Gly Asn Ile Val Asn His Tyr Tyr Leu Val Asp Leu
                325                 330                 335 cta aaa cgt gat ttg gat cag tgg tgt gag aat atg cca tat cac att     1056
Leu Lys Arg Asp Leu Asp Gln Trp Cys Glu Asn Met Pro Tyr His Ile
            340                 345                 350 gcg aag aag aaa att cca gct tat gat agt gtt acc ggc aag tac act     1104
Ala Lys Lys Lys Ile Pro Ala Tyr Asp Ser Val Thr Gly Lys Tyr Thr
        355                 360                 365 aag cct acc gaa cca aac ggt ata aaa tta gag caa ttc ata ttt gat     1152
Lys Pro Thr Glu Pro Asn Gly Ile Lys Leu Glu Gln Phe Ile Phe Asp
    370                 375                 380 gtc ttt gac act gta cca ctg aac aag ttt ggg tgc tta gaa gta gat     1200
Val Phe Asp Thr Val Pro Leu Asn Lys Phe Gly Cys Leu Glu Val Asp
385                 390                 395                 400 aga tgc aaa gaa ttt tca cct tta aaa aac ggt cct ggt tct aag aac     1248
Arg Cys Lys Glu Phe Ser Pro Leu Lys Asn Gly Pro Gly Ser Lys Asn
                405                 410                 415 gat aat cct gag acc agc aga cta gca tat ttg aaa cta gga acc tcg     1296
Asp Asn Pro Glu Thr Ser Arg Leu Ala Tyr Leu Lys Leu Gly Thr Ser
            420                 425                 430 tgg ttg gaa gat gca ggc gct att gta aaa gat ggg gta cta gtc gaa     1344
Trp Leu Glu Asp Ala Gly Ala Ile Val Lys Asp Gly Val Leu Val Glu
        435                 440                 445 gtt tcc agc aaa ttg agt tat gca ggt gaa aat cta tcc cag ttc aaa     1392
Val Ser Ser Lys Leu Ser Tyr Ala Gly Glu Asn Leu Ser Gln Phe Lys
    450                 455                 460 ggt aaa gtc ttt gac aga agt ggt ata gta tta gaa aaa taa             1434
Gly Lys Val Phe Asp Arg Ser Gly Ile Val Leu Glu Lys
465                 470                 475

<210> SEQ ID NO 11
<211> LENGTH: 477
<212> TYPE: PRT
<213> ORGANISM: Saccharomyces cerevisiae

<400> SEQUENCE: 11

Met Thr Asp Thr Lys Gln Leu Phe Ile Glu Ala Gly Gln Ser Gln Leu
```

```
1               5                   10                  15
Phe His Asn Trp Glu Ser Leu Ser Arg Lys Asp Gln Glu Glu Leu Leu
            20                  25                  30

Ser Asn Leu Glu Gln Ile Ser Ser Lys Arg Ser Pro Ala Lys Leu Leu
            35                  40                  45

Glu Asp Cys Gln Asn Ala Ile Lys Phe Ser Leu Ala Asn Ser Ser Lys
            50                  55                  60

Asp Thr Gly Val Glu Ile Ser Pro Leu Pro Thr Ser Tyr Glu Ser
65                      70                  75                  80

Leu Ile Gly Asn Ser Lys Lys Glu Asn Glu Tyr Trp Arg Leu Gly Leu
                85                  90                  95

Glu Ala Ile Gly Lys Gly Glu Val Ala Val Ile Leu Met Ala Gly Gly
                100                 105                 110

Gln Gly Thr Arg Leu Gly Ser Ser Gln Pro Lys Gly Cys Tyr Asp Ile
                115                 120                 125

Gly Leu Pro Ser Lys Lys Ser Leu Phe Gln Ile Gln Ala Glu Lys Leu
            130                 135                 140

Ile Arg Leu Gln Asp Met Val Lys Asp Lys Val Glu Ile Pro Trp
145                 150                 155                 160

Tyr Ile Met Thr Ser Gly Pro Thr Arg Ala Ala Thr Glu Ala Tyr Phe
                165                 170                 175

Gln Glu His Asn Tyr Phe Gly Leu Asn Lys Glu Gln Ile Thr Phe Phe
                180                 185                 190

Asn Gln Gly Thr Leu Pro Ala Phe Asp Leu Thr Gly Lys His Phe Leu
                195                 200                 205

Met Lys Asp Pro Val Asn Leu Ser Gln Ser Pro Asp Gly Asn Gly Gly
            210                 215                 220

Leu Tyr Arg Ala Ile Lys Glu Asn Lys Leu Asn Glu Asp Phe Asp Arg
225                 230                 235                 240

Arg Gly Ile Lys His Val Tyr Met Tyr Cys Val Asp Asn Val Leu Ser
                245                 250                 255

Lys Ile Ala Asp Pro Val Phe Ile Gly Phe Ala Ile Lys His Gly Phe
            260                 265                 270

Glu Leu Ala Thr Lys Ala Val Arg Lys Arg Asp Ala His Glu Ser Val
            275                 280                 285

Gly Leu Ile Ala Thr Lys Asn Glu Lys Pro Cys Val Ile Glu Tyr Ser
            290                 295                 300

Glu Ile Ser Asn Glu Leu Ala Glu Ala Lys Asp Lys Asp Gly Leu Leu
305                 310                 315                 320

Lys Leu Arg Ala Gly Asn Ile Val Asn His Tyr Tyr Leu Val Asp Leu
                325                 330                 335

Leu Lys Arg Asp Leu Asp Gln Trp Cys Glu Asn Met Pro Tyr His Ile
            340                 345                 350

Ala Lys Lys Lys Ile Pro Ala Tyr Asp Ser Val Thr Gly Lys Tyr Thr
            355                 360                 365

Lys Pro Thr Glu Pro Asn Gly Ile Lys Leu Glu Gln Phe Ile Phe Asp
            370                 375                 380

Val Phe Asp Thr Val Pro Leu Asn Lys Phe Gly Cys Leu Glu Val Asp
385                 390                 395                 400

Arg Cys Lys Glu Phe Ser Pro Leu Lys Asn Gly Pro Gly Ser Lys Asn
                405                 410                 415

Asp Asn Pro Glu Thr Ser Arg Leu Ala Tyr Leu Lys Leu Gly Thr Ser
            420                 425                 430
```

Trp Leu Glu Asp Ala Gly Ala Ile Val Lys Asp Gly Val Leu Val Glu
        435                 440                 445

Val Ser Ser Lys Leu Ser Tyr Ala Gly Glu Asn Leu Ser Gln Phe Lys
    450                 455                 460

Gly Lys Val Phe Asp Arg Ser Gly Ile Val Leu Glu Lys
465                 470                 475

<210> SEQ ID NO 12
<211> LENGTH: 919
<212> TYPE: DNA
<213> ORGANISM: Artificial Sequence
<220> FEATURE:
<223> OTHER INFORMATION: Recombinant nucleic acid sequence comprising
      sequnces for an YLCV promoter, a cloning site, an ocs-termination
      signal and a nos-termination signal.
<220> FEATURE:
<221> NAME/KEY: promoter
<222> LOCATION: (8)..(352)
<223> OTHER INFORMATION: Sequence of the YLCV promoter
<220> FEATURE:
<221> NAME/KEY: polyA_signal
<222> LOCATION: (366)..(663)
<223> OTHER INFORMATION: polyA-signal of the ocs gene from Agrobacterium
      tumefaciens
<220> FEATURE:
<221> NAME/KEY: polyA_signal
<222> LOCATION: (664)..(872)
<223> OTHER INFORMATION: polyA-signal of the nos gene from Agrobacterium
      tumefaciens

<400> SEQUENCE: 12
gaattcctgg cagacaaagt ggcagacata ctgtcccaca aatgaagatg gaatctgtaa      60
aagaaaacgc gtgaaataat gcgtctgaca aaggttaggt cggctgcctt taatcaatac     120
caaagtggtc cctaccacga tggaaaaact gtgcagtcgg tttggctttt tctgacgaac     180
aaataagatt cgtggccgac aggtgggggt ccaccatgtg aaggcatctt cagactccaa     240
taatggagca atgacgtaag ggcttacgaa ataagtaagg gtagtttggg aaatgtccac     300
tcacccgtca gtctataaat acttagcccc tccctcattg ttaagggagc aagagctcgc     360
ccgggatctc gaatcacgcg ttctaggatc cgaagcagat cgttcaaaca tttggcaata     420
aagtttctta agattgaatc ctgttgccgg tcttgcgatg attatcatat aatttctgtt     480
gaattacgtt aagcatgtaa taattaacat gtaatgcatg acgttattta tgagatgggt     540
ttttatgatt agagtcccgc aattatacat taatacgcg atagaaaaca aaatatagcg     600
cgcaaactag gataaattat cgcgcgcggt gtcatctatg ttactagatc gggaagatct     660
cgagacgtcg ggacaatcag taaattgaac ggagaatatt attcataaaa atacgatagt     720
aacgggtgat atattcatta gaatgaaccg aaaccggcgg taaggatctg agctacacat     780
gctcaggttt tttacaacgt gcacaacaga attgaaagca aatatcatgc gatcataggc     840
gtctcgcata tctcattaaa gcagggcatg cctgtttaaa cattaattaa acctaggtga     900
cgtctaaaag ggcgaattc                                                  919

<210> SEQ ID NO 13
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 13
tcgacaggcc tggatcctta attaaactag tctcgaggag ctcggtac                    48

<210> SEQ ID NO 14
<211> LENGTH: 40
<212> TYPE: DNA
<213> ORGANISM: Artificial Sequence
<220> FEATURE:
<223> OTHER INFORMATION: Synthetic oligonusleotide

<400> SEQUENCE: 14
cgagctcctc gagactagtt taattaagga tccaggcctg            40

<210> SEQ ID NO 15
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 15
cttaattaat agttgacgaa cggaagctg                        29

<210> SEQ ID NO 16
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 16
agcatgcttg cagaccgtca ttagg                            25

<210> SEQ ID NO 17
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 17
aaagtgcttc ataagtagct caaaca                           26

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
aacaccagat cgaactgcaa                                  20

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
ccgccttttt agccagttat c                                21

<210> SEQ ID NO 20
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 20
ccactctgtc tgcaaaggaa　　　　　　　　　　　　　　　　　　　　　　　　　20

<210> SEQ ID NO 21
<211> LENGTH: 1338
<212> TYPE: DNA
<213> ORGANISM: Escherichia coli
<220> FEATURE:
<221> NAME/KEY: CDS
<222> LOCATION: (1)..(1338)
<300> PUBLICATION INFORMATION:
<308> DATABASE ACCESSION NUMBER: GenBank/AY616604
<309> DATABASE ENTRY DATE: 2006-08-18
<313> RELEVANT RESIDUES IN SEQ ID NO: (1)..(1338)

<400> SEQUENCE: 21

| | | | | | | | | | | | | | | | | |
|---|---|---|---|---|---|---|---|---|---|---|---|---|---|---|---|---|
| atg | agt | aat | cgt | aaa | tat | ttc | ggt | acc | gat | ggg | att | cgt | ggt | cgt | gta | 48 |
| Met | Ser | Asn | Arg | Lys | Tyr | Phe | Gly | Thr | Asp | Gly | Ile | Arg | Gly | Arg | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggg | gat | gcg | ccg | atc | aca | cct | gat | ttt | gtg | ctt | aag | ctg | ggt | tgg | gcc | 96 |
| Gly | Asp | Ala | Pro | Ile | Thr | Pro | Asp | Phe | Val | Leu | Lys | Leu | Gly | Trp | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| gcg | ggt | aaa | gtg | ctg | gcg | cgc | cac | ggc | tcc | cgt | aag | att | att | att | ggt | 144 |
| Ala | Gly | Lys | Val | Leu | Ala | Arg | His | Gly | Ser | Arg | Lys | Ile | Ile | Ile | Gly | |
| | 35 | | | | | 40 | | | | | 45 | | | | | |

| | | | | | | | | | | | | | | | | |
|---|---|---|---|---|---|---|---|---|---|---|---|---|---|---|---|---|
| aaa | gac | acg | cgt | att | tct | ggc | tat | atg | ctg | gag | tca | gca | ctg | gaa | gcg | 192 |
| Lys | Asp | Thr | Arg | Ile | Ser | Gly | Tyr | Met | Leu | Glu | Ser | Ala | Leu | Glu | Ala | |
| 50 | | | | | 55 | | | | | 60 | | | | | | |

| | | | | | | | | | | | | | | | | |
|---|---|---|---|---|---|---|---|---|---|---|---|---|---|---|---|---|
| ggt | ctg | gcg | gca | gcg | ggc | ctt | tcc | gca | ctc | ttc | act | ggc | ccg | atg | cca | 240 |
| Gly | Leu | Ala | Ala | Ala | Gly | Leu | Ser | Ala | Leu | Phe | Thr | Gly | Pro | Met | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aca | ccg | gcc | gtg | gct | tat | ctg | acg | cgt | acc | ttc | cgc | gca | gag | gcc | gga | 288 |
| Thr | Pro | Ala | Val | Ala | Tyr | Leu | Thr | Arg | Thr | Phe | Arg | Ala | Glu | Ala | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| att | gtg | ata | tct | gca | tcg | cat | aac | ccg | ttc | tac | gat | aat | ggc | att | aaa | 336 |
| Ile | Val | Ile | Ser | Ala | Ser | His | Asn | Pro | Phe | Tyr | Asp | Asn | Gly | Ile | Lys | |
| | | | 100 | | | | | 105 | | | | | 110 | | | |

| | | | | | | | | | | | | | | | | |
|---|---|---|---|---|---|---|---|---|---|---|---|---|---|---|---|---|
| ttc | ttc | tct | atc | gac | ggc | acc | aaa | ctg | ccg | gat | gcg | gta | gaa | gag | gcc | 384 |
| Phe | Phe | Ser | Ile | Asp | Gly | Thr | Lys | Leu | Pro | Asp | Ala | Val | Glu | Glu | Ala | |
| | | | 115 | | | | | 120 | | | | | 125 | | | |

| | | | | | | | | | | | | | | | | |
|---|---|---|---|---|---|---|---|---|---|---|---|---|---|---|---|---|
| atc | gaa | gcg | gaa | atg | gaa | aag | gag | atc | agc | tgc | gtt | gat | tcg | gca | gaa | 432 |
| Ile | Glu | Ala | Glu | Met | Glu | Lys | Glu | Ile | Ser | Cys | Val | Asp | Ser | Ala | Glu | |
| | | 130 | | | | | 135 | | | | | 140 | | | | |

| | | | | | | | | | | | | | | | | |
|---|---|---|---|---|---|---|---|---|---|---|---|---|---|---|---|---|
| ctg | ggt | aaa | gcc | agc | cgt | atc | gtt | gat | gcc | gcg | ggt | cgc | tat | atc | gag | 480 |
| Leu | Gly | Lys | Ala | Ser | Arg | Ile | Val | Asp | Ala | Ala | Gly | Arg | Tyr | Ile | Glu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ttt | tgc | aaa | gcc | acg | ttc | ccg | aac | gaa | ctt | agc | ctc | agt | gaa | ctg | aag | 528 |
| Phe | Cys | Lys | Ala | Thr | Phe | Pro | Asn | Glu | Leu | Ser | Leu | Ser | Glu | Leu | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| att | gtg | gtg | gat | tgt | gca | aac | ggt | gcg | act | tat | cac | atc | gcg | ccg | aac | 576 |
| Ile | Val | Val | Asp | Cys | Ala | Asn | Gly | Ala | Thr | Tyr | His | Ile | Ala | Pro | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| gtg | ctg | cgc | gaa | ctg | ggg | gcg | aac | gtt | atc | gct | atc | ggt | tgt | gag | cca | 624 |
| Val | Leu | Arg | Glu | Leu | Gly | Ala | Asn | Val | Ile | Ala | Ile | Gly | Cys | Glu | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| aac | ggt | gta | aac | atc | aat | gcc | gaa | gtg | ggg | gct | acc | gac | gtt | cgc | gcg | 672 |
| Asn | Gly | Val | Asn | Ile | Asn | Ala | Glu | Val | Gly | Ala | Thr | Asp | Val | Arg | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| ctc | cag | gct | cgt | gtg | ctg | gct | gaa | aaa | gcg | gat | ctc | ggt | att | gcc | ttc | 720 |
| Leu | Gln | Ala | Arg | Val | Leu | Ala | Glu | Lys | Ala | Asp | Leu | Gly | Ile | Ala | Phe | |

```
                  225                 230                 235                 240
gac ggc gat ggc gat cgc gtg att atg gtt gac cat gaa ggc aat aaa      768
Asp Gly Asp Gly Asp Arg Val Ile Met Val Asp His Glu Gly Asn Lys
                  245                 250                 255 gtc gat ggc gat cag atc atg tat atc atc gcg cgt gaa ggt ctt cgt      816
Val Asp Gly Asp Gln Ile Met Tyr Ile Ile Ala Arg Glu Gly Leu Arg
                  260                 265                 270 cag ggc cag ctg cgt ggt ggc gct gtg ggt aca ttg atg agc aac atg      864
Gln Gly Gln Leu Arg Gly Gly Ala Val Gly Thr Leu Met Ser Asn Met
              275                 280                 285 ggg ctt gaa ctg gcg ctg aaa cag tta gga att cca ttt gcg cgc gcg      912
Gly Leu Glu Leu Ala Leu Lys Gln Leu Gly Ile Pro Phe Ala Arg Ala
290                 295                 300 aaa gtg ggt gac cgc tac gta ctg gaa aaa atg cag gag aaa ggc tgg      960
Lys Val Gly Asp Arg Tyr Val Leu Glu Lys Met Gln Glu Lys Gly Trp
305                 310                 315                 320 cgt atc ggt gca gag aat tcc ggt cat gtg atc ctg ctg gat aaa act     1008
Arg Ile Gly Ala Glu Asn Ser Gly His Val Ile Leu Leu Asp Lys Thr
                  325                 330                 335 act acc ggt gac ggc atc gtt gct ggc ttg cag gtg ctg gcg gcg atg     1056
Thr Thr Gly Asp Gly Ile Val Ala Gly Leu Gln Val Leu Ala Ala Met
                  340                 345                 350 gca cgt aac cat atg agc ctg cac gac ctt tgc agc ggc atg aaa atg     1104
Ala Arg Asn His Met Ser Leu His Asp Leu Cys Ser Gly Met Lys Met
                  355                 360                 365 ttc ccg cag att ctg gtt aac gta cgt tac acc gca ggt agc ggc gat     1152
Phe Pro Gln Ile Leu Val Asn Val Arg Tyr Thr Ala Gly Ser Gly Asp
              370                 375                 380 cca ctt gag cat gag tca gtt aaa gcc gtg acc gca gag gtt gaa gct     1200
Pro Leu Glu His Glu Ser Val Lys Ala Val Thr Ala Glu Val Glu Ala
385                 390                 395                 400 gcg ctg ggc aac cgt gga cgc gtg ttg ctg cgt aaa tcc ggc acc gaa     1248
Ala Leu Gly Asn Arg Gly Arg Val Leu Leu Arg Lys Ser Gly Thr Glu
                  405                 410                 415 ccg tta att cgc gtg atg gtg gaa ggc gaa gac gaa gcg cag gtg act     1296
Pro Leu Ile Arg Val Met Val Glu Gly Glu Asp Glu Ala Gln Val Thr
                  420                 425                 430 gaa ttt gca cac cgc atc gcc gat gca gta aaa gcc gtt taa              1338
Glu Phe Ala His Arg Ile Ala Asp Ala Val Lys Ala Val
                  435                 440                 445

<210> SEQ ID NO 22
<211> LENGTH: 445
<212> TYPE: PRT
<213> ORGANISM: Escherichia coli

<400> SEQUENCE: 22

Met Ser Asn Arg Lys Tyr Phe Gly Thr Asp Gly Ile Arg Gly Arg Val
1               5                   10                  15

Gly Asp Ala Pro Ile Thr Pro Asp Phe Val Leu Lys Leu Gly Trp Ala
                20                  25                  30

Ala Gly Lys Val Leu Ala Arg His Gly Ser Arg Lys Ile Ile Ile Gly
            35                  40                  45

Lys Asp Thr Arg Ile Ser Gly Tyr Met Leu Glu Ser Ala Leu Glu Ala
        50                  55                  60

Gly Leu Ala Ala Ala Gly Leu Ser Ala Leu Phe Thr Gly Pro Met Pro
65                  70                  75                  80

Thr Pro Ala Val Ala Tyr Leu Thr Arg Thr Phe Arg Ala Glu Ala Gly
                85                  90                  95
```

Ile Val Ile Ser Ala Ser His Asn Pro Phe Tyr Asp Asn Gly Ile Lys
            100                 105                 110

Phe Phe Ser Ile Asp Gly Thr Lys Leu Pro Asp Ala Val Glu Glu Ala
            115                 120                 125

Ile Glu Ala Glu Met Glu Lys Glu Ile Ser Cys Val Asp Ser Ala Glu
130                 135                 140

Leu Gly Lys Ala Ser Arg Ile Val Asp Ala Ala Gly Arg Tyr Ile Glu
145                 150                 155                 160

Phe Cys Lys Ala Thr Phe Pro Asn Glu Leu Ser Leu Ser Glu Leu Lys
            165                 170                 175

Ile Val Val Asp Cys Ala Asn Gly Ala Thr Tyr His Ile Ala Pro Asn
            180                 185                 190

Val Leu Arg Glu Leu Gly Ala Asn Val Ile Ala Ile Gly Cys Glu Pro
            195                 200                 205

Asn Gly Val Asn Ile Asn Ala Glu Val Gly Ala Thr Asp Val Arg Ala
            210                 215                 220

Leu Gln Ala Arg Val Leu Ala Glu Lys Ala Asp Leu Gly Ile Ala Phe
225                 230                 235                 240

Asp Gly Asp Gly Asp Arg Val Ile Met Val Asp His Glu Gly Asn Lys
            245                 250                 255

Val Asp Gly Asp Gln Ile Met Tyr Ile Ile Ala Arg Glu Gly Leu Arg
            260                 265                 270

Gln Gly Gln Leu Arg Gly Gly Ala Val Gly Thr Leu Met Ser Asn Met
            275                 280                 285

Gly Leu Glu Leu Ala Leu Lys Gln Leu Gly Ile Pro Phe Ala Arg Ala
            290                 295                 300

Lys Val Gly Asp Arg Tyr Val Leu Glu Lys Met Gln Glu Lys Gly Trp
305                 310                 315                 320

Arg Ile Gly Ala Glu Asn Ser Gly His Val Ile Leu Leu Asp Lys Thr
            325                 330                 335

Thr Thr Gly Asp Gly Ile Val Ala Gly Leu Gln Val Leu Ala Ala Met
            340                 345                 350

Ala Arg Asn His Met Ser Leu His Asp Leu Cys Ser Gly Met Lys Met
            355                 360                 365

Phe Pro Gln Ile Leu Val Asn Val Arg Tyr Thr Ala Gly Ser Gly Asp
            370                 375                 380

Pro Leu Glu His Glu Ser Val Lys Ala Val Thr Ala Glu Val Glu Ala
385                 390                 395                 400

Ala Leu Gly Asn Arg Gly Arg Val Leu Leu Arg Lys Ser Gly Thr Glu
            405                 410                 415

Pro Leu Ile Arg Val Met Val Glu Gly Glu Asp Glu Ala Gln Val Thr
            420                 425                 430

Glu Phe Ala His Arg Ile Ala Asp Ala Val Lys Ala Val
            435                 440                 445

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
attacccggc cagaatcact                                           20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gtcaggacgc gtatgttgaa                                              20

<210> SEQ ID NO 25
<211> LENGTH: 1371
<212> TYPE: DNA
<213> ORGANISM: Escherichia coli
<220> FEATURE:
<221> NAME/KEY: CDS
<222> LOCATION: (1)..(1368)
<300> PUBLICATION INFORMATION:
<308> DATABASE ACCESSION NUMBER: GenBank/AP009048.1
<309> DATABASE ENTRY DATE: 2007-05-19
<313> RELEVANT RESIDUES IN SEQ ID NO: (3721481)..(3722851)

<400> SEQUENCE: 25

```
atg ttg aat aat gct atg agc gta gtg atc ctt gcc gca ggc aaa ggc       48
Met Leu Asn Asn Ala Met Ser Val Val Ile Leu Ala Ala Gly Lys Gly
 1               5                  10                  15 acg cgc atg tat tcc gat ctt ccg aaa gtg ctg cat acc ctt gcc ggg       96
Thr Arg Met Tyr Ser Asp Leu Pro Lys Val Leu His Thr Leu Ala Gly
             20                  25                  30 aaa gcg atg gtt cag cat gtc att gat gct gcg aat gaa tta ggc gca      144
Lys Ala Met Val Gln His Val Ile Asp Ala Ala Asn Glu Leu Gly Ala
         35                  40                  45 gcg cac gtt cac ctg gtg tac ggt cac ggc ggc gat ctg cta aaa cag      192
Ala His Val His Leu Val Tyr Gly His Gly Gly Asp Leu Leu Lys Gln
     50                  55                  60 gcg ctg aaa gac gac aac ctt aac tgg gtg ctt cag gca gag cag ctg      240
Ala Leu Lys Asp Asp Asn Leu Asn Trp Val Leu Gln Ala Glu Gln Leu
 65                  70                  75                  80 ggt acg ggt cat gca atg cag cag gcc gca cct ttc ttt gcc gat gat      288
Gly Thr Gly His Ala Met Gln Gln Ala Ala Pro Phe Phe Ala Asp Asp
                 85                  90                  95 gaa gac att tta atg ctc tac ggc gac gtg ccg ctg atc tct gtc gaa      336
Glu Asp Ile Leu Met Leu Tyr Gly Asp Val Pro Leu Ile Ser Val Glu
            100                 105                 110 aca ctc cag cgt ctg cgt gat gct aaa ccg cag ggt ggc att ggt ctg      384
Thr Leu Gln Arg Leu Arg Asp Ala Lys Pro Gln Gly Gly Ile Gly Leu
        115                 120                 125 ctg acg gtg aaa ctg gat gat ccg acc ggt tat gga cgt atc acc cgt      432
Leu Thr Val Lys Leu Asp Asp Pro Thr Gly Tyr Gly Arg Ile Thr Arg
    130                 135                 140 gaa aac ggc aaa gtt acc ggc att gtt gag cac aaa gat gcc acc ggc      480
Glu Asn Gly Lys Val Thr Gly Ile Val Glu His Lys Asp Ala Thr Gly
145                 150                 155                 160 gag cag cgt cag att cag gag atc aac acc ggc att ctg att gcc aac      528
Glu Gln Arg Gln Ile Gln Glu Ile Asn Thr Gly Ile Leu Ile Ala Asn
                165                 170                 175 ggc gca gat atg aaa cgc tgg ctg gcg aag ctg acc aac aat aat gct      576
Gly Ala Asp Met Lys Arg Trp Leu Ala Lys Leu Thr Asn Asn Asn Ala
            180                 185                 190 cag ggc gaa tac tac atc acc gac att att gcg ctg gcg tat cag gaa      624
Gln Gly Glu Tyr Tyr Ile Thr Asp Ile Ile Ala Leu Ala Tyr Gln Glu
        195                 200                 205
```

```
ggg cgt gaa atc gtc gcc gtt cat ccg caa cgt tta agc gaa gta gaa      672
Gly Arg Glu Ile Val Ala Val His Pro Gln Arg Leu Ser Glu Val Glu
    210                 215                 220 ggc gtg aat aac cgc ctg caa ctc tcc cgt ctg gag cgt gtt tat cag      720
Gly Val Asn Asn Arg Leu Gln Leu Ser Arg Leu Glu Arg Val Tyr Gln
225                 230                 235                 240 tcc gaa cag gct gaa aaa ctg ctg tta gca ggc gtt atg ctg cgc gat      768
Ser Glu Gln Ala Glu Lys Leu Leu Leu Ala Gly Val Met Leu Arg Asp
                245                 250                 255 cca gcg cgt ttt gat ctg cgt ggt acg cta act cac ggg cgc gat gtt      816
Pro Ala Arg Phe Asp Leu Arg Gly Thr Leu Thr His Gly Arg Asp Val
            260                 265                 270 gaa att gat act aac gtt atc atc gag ggc aac gtg act ctc ggt cat      864
Glu Ile Asp Thr Asn Val Ile Ile Glu Gly Asn Val Thr Leu Gly His
        275                 280                 285 cgc gtg aaa att ggc acc ggt tgc gtg att aaa aac agc gtg att ggc      912
Arg Val Lys Ile Gly Thr Gly Cys Val Ile Lys Asn Ser Val Ile Gly
    290                 295                 300 gat gat tgc gaa atc agt ccg tat acc gtt gtg gaa gat gcg aat ctg      960
Asp Asp Cys Glu Ile Ser Pro Tyr Thr Val Val Glu Asp Ala Asn Leu
305                 310                 315                 320 gca gcg gcc tgt acc att ggc ccg ttt gcc cgt ttg cgt cct ggt gct     1008
Ala Ala Ala Cys Thr Ile Gly Pro Phe Ala Arg Leu Arg Pro Gly Ala
                325                 330                 335 gag ttg ctg gaa ggt gct cac gtc ggt aac ttc gtt gag atg aaa aaa     1056
Glu Leu Leu Glu Gly Ala His Val Gly Asn Phe Val Glu Met Lys Lys
            340                 345                 350 gcg cgt ctg ggt aaa ggc tcg aaa gct ggt cat ctg act tac ctg ggc     1104
Ala Arg Leu Gly Lys Gly Ser Lys Ala Gly His Leu Thr Tyr Leu Gly
        355                 360                 365 gat gcg gaa att ggc gat aac gtt aac atc ggc gcg gga acc att acc     1152
Asp Ala Glu Ile Gly Asp Asn Val Asn Ile Gly Ala Gly Thr Ile Thr
    370                 375                 380 tgc aac tac gat ggt gcg aat aaa ttt aag acc att atc ggc gac gat     1200
Cys Asn Tyr Asp Gly Ala Asn Lys Phe Lys Thr Ile Ile Gly Asp Asp
385                 390                 395                 400 gtg ttt gtt ggt tcc gac act cag ctg gtg gcc ccg gta aca gta ggc     1248
Val Phe Val Gly Ser Asp Thr Gln Leu Val Ala Pro Val Thr Val Gly
                405                 410                 415 aaa ggc gcg acc att gct gcg ggt aca act gtg acg cgt aat gtc ggc     1296
Lys Gly Ala Thr Ile Ala Ala Gly Thr Thr Val Thr Arg Asn Val Gly
            420                 425                 430 gaa aat gca tta gct atc agc cgt gtg ccg cag act cag aaa gaa ggc     1344
Glu Asn Ala Leu Ala Ile Ser Arg Val Pro Gln Thr Gln Lys Glu Gly
        435                 440                 445 tgg cgt cgt ccg gta aag aaa aag tga                                 1371
Trp Arg Arg Pro Val Lys Lys Lys
    450                 455

<210> SEQ ID NO 26
<211> LENGTH: 456
<212> TYPE: PRT
<213> ORGANISM: Escherichia coli

<400> SEQUENCE: 26

Met Leu Asn Asn Ala Met Ser Val Val Ile Leu Ala Ala Gly Lys Gly
1               5                   10                  15

Thr Arg Met Tyr Ser Asp Leu Pro Lys Val Leu His Thr Leu Ala Gly
            20                  25                  30

Lys Ala Met Val Gln His Val Ile Asp Ala Ala Asn Glu Leu Gly Ala
```

```
                35                  40                  45
Ala His Val His Leu Val Tyr Gly His Gly Gly Asp Leu Leu Lys Gln
             50                  55                  60
Ala Leu Lys Asp Asp Asn Leu Asn Trp Val Leu Gln Ala Glu Gln Leu
 65                  70                  75                  80
Gly Thr Gly His Ala Met Gln Gln Ala Ala Pro Phe Phe Ala Asp Asp
                 85                  90                  95
Glu Asp Ile Leu Met Leu Tyr Gly Asp Val Pro Leu Ile Ser Val Glu
                100                 105                 110
Thr Leu Gln Arg Leu Arg Asp Ala Lys Pro Gln Gly Gly Ile Gly Leu
            115                 120                 125
Leu Thr Val Lys Leu Asp Asp Pro Thr Gly Tyr Gly Arg Ile Thr Arg
    130                 135                 140
Glu Asn Gly Lys Val Thr Gly Ile Val Glu His Lys Asp Ala Thr Gly
145                 150                 155                 160
Glu Gln Arg Gln Ile Gln Glu Ile Asn Thr Gly Ile Leu Ile Ala Asn
                165                 170                 175
Gly Ala Asp Met Lys Arg Trp Leu Ala Lys Leu Thr Asn Asn Asn Ala
            180                 185                 190
Gln Gly Glu Tyr Tyr Ile Thr Asp Ile Ile Ala Leu Ala Tyr Gln Glu
        195                 200                 205
Gly Arg Glu Ile Val Ala Val His Pro Gln Arg Leu Ser Glu Val Glu
    210                 215                 220
Gly Val Asn Asn Arg Leu Gln Leu Ser Arg Leu Glu Arg Val Tyr Gln
225                 230                 235                 240
Ser Glu Gln Ala Glu Lys Leu Leu Leu Ala Gly Val Met Leu Arg Asp
                245                 250                 255
Pro Ala Arg Phe Asp Leu Arg Gly Thr Leu Thr His Gly Arg Asp Val
            260                 265                 270
Glu Ile Asp Thr Asn Val Ile Ile Glu Gly Asn Val Thr Leu Gly His
        275                 280                 285
Arg Val Lys Ile Gly Thr Gly Cys Val Ile Lys Asn Ser Val Ile Gly
    290                 295                 300
Asp Asp Cys Glu Ile Ser Pro Tyr Thr Val Val Glu Asp Ala Asn Leu
305                 310                 315                 320
Ala Ala Ala Cys Thr Ile Gly Pro Phe Ala Arg Leu Arg Pro Gly Ala
                325                 330                 335
Glu Leu Leu Glu Gly Ala His Val Gly Asn Phe Val Glu Met Lys Lys
            340                 345                 350
Ala Arg Leu Gly Lys Gly Ser Lys Ala Gly His Leu Thr Tyr Leu Gly
        355                 360                 365
Asp Ala Glu Ile Gly Asp Asn Val Asn Ile Gly Ala Gly Thr Ile Thr
    370                 375                 380
Cys Asn Tyr Asp Gly Ala Asn Lys Phe Lys Thr Ile Ile Gly Asp Asp
385                 390                 395                 400
Val Phe Val Gly Ser Asp Thr Gln Leu Val Ala Pro Val Thr Val Gly
                405                 410                 415
Lys Gly Ala Thr Ile Ala Ala Gly Thr Thr Val Thr Arg Asn Val Gly
            420                 425                 430
Glu Asn Ala Leu Ala Ile Ser Arg Val Pro Gln Thr Gln Lys Glu Gly
        435                 440                 445
Trp Arg Arg Pro Val Lys Lys Lys
    450                 455
```

<210> SEQ ID NO 27
<211> LENGTH: 20
<212> TYPE: DNA
<213> ORGANISM: Artificial Seqeunce
<220> FEATURE:
<223> OTHER INFORMATION: Synthetic oligonucleotide

<400> SEQUENCE: 27
ggcaaaggtc agcagtaagc                                              20

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 28
tcaagcagat gccttaacgt g                                            21

<210> SEQ ID NO 29
<211> LENGTH: 1674
<212> TYPE: DNA
<213> ORGANISM: Saccharomyces cerevisiae
<220> FEATURE:
<221> NAME/KEY: CDS
<222> LOCATION: (1)..(1671)

<400> SEQUENCE: 29

```
atg aag gtt gat tac gag caa ttg tgc aaa ctc tac gat gac acg tgc        48
Met Lys Val Asp Tyr Glu Gln Leu Cys Lys Leu Tyr Asp Asp Thr Cys
1               5                   10                  15 cgc aca aag aat gtg cag ttc agt tac ggt acg gcc gga ttc aga acg        96
Arg Thr Lys Asn Val Gln Phe Ser Tyr Gly Thr Ala Gly Phe Arg Thr
            20                  25                  30 ctg gcc aag aat ttg gat acg gtg atg ttc agt act ggt ata ctg gcg       144
Leu Ala Lys Asn Leu Asp Thr Val Met Phe Ser Thr Gly Ile Leu Ala
        35                  40                  45 gtt ctc agg tcg ctg aag ctt cag ggt cag tat gtg ggg gtg atg atc       192
Val Leu Arg Ser Leu Lys Leu Gln Gly Gln Tyr Val Gly Val Met Ile
    50                  55                  60 acg gcg tcg cac aac cca tac cag gac aac ggg gtc aag atc gtg gaa       240
Thr Ala Ser His Asn Pro Tyr Gln Asp Asn Gly Val Lys Ile Val Glu
65                  70                  75                  80 cca gac gga tcg atg ctt ttg gcc aca tgg gag cca tat gcc atg cag       288
Pro Asp Gly Ser Met Leu Leu Ala Thr Trp Glu Pro Tyr Ala Met Gln
                85                  90                  95 ttg gcc aat gcg gcc tct ttt gcc act aat ttt gaa gaa ttt cgt gtt       336
Leu Ala Asn Ala Ala Ser Phe Ala Thr Asn Phe Glu Glu Phe Arg Val
            100                 105                 110 gag ttg gcc aag ctg att gaa cac gaa aag att gat ttg aat aca acc       384
Glu Leu Ala Lys Leu Ile Glu His Glu Lys Ile Asp Leu Asn Thr Thr
        115                 120                 125 gtc gtg cct cac atc gtg gtt ggg aga gac tct agg gaa agt agt cca       432
Val Val Pro His Ile Val Val Gly Arg Asp Ser Arg Glu Ser Ser Pro
    130                 135                 140 tac ttg ctg cgc tgc ttg act tcc tcc atg gcc agc gtc ttc cac gcg       480
Tyr Leu Leu Arg Cys Leu Thr Ser Ser Met Ala Ser Val Phe His Ala
145                 150                 155                 160 caa gtt ttg gac cta ggc tgt gtc act acg cct caa ttg cat tac att       528
Gln Val Leu Asp Leu Gly Cys Val Thr Thr Pro Gln Leu His Tyr Ile
                165                 170                 175
```

-continued

```
act gat ttg tcc aac agg cgg aaa ctg gaa gga gac aca gcg cca gtt    576
Thr Asp Leu Ser Asn Arg Arg Lys Leu Glu Gly Asp Thr Ala Pro Val
            180                 185                 190 gcc aca gaa cag gac tac tat tcg ttc ttt ata gga gcc ttc aac gag    624
Ala Thr Glu Gln Asp Tyr Tyr Ser Phe Phe Ile Gly Ala Phe Asn Glu
        195                 200                 205 ctc ttc gcc acg tat cag ctg gag aag agg ctg tct gtc cca aaa ttg    672
Leu Phe Ala Thr Tyr Gln Leu Glu Lys Arg Leu Ser Val Pro Lys Leu
    210                 215                 220 ttc ata gac aca gcc aat ggt atc ggt ggt cca cag ttg aaa aaa cta    720
Phe Ile Asp Thr Ala Asn Gly Ile Gly Gly Pro Gln Leu Lys Lys Leu
225                 230                 235                 240 ctg gcc tcc gaa gat tgg gac gtg cca gcg gag caa gtt gag gta atc    768
Leu Ala Ser Glu Asp Trp Asp Val Pro Ala Glu Gln Val Glu Val Ile
            245                 250                 255 aac gac agg tcc gat gtt cca gaa ctg ttg aat ttt gaa tgc ggt gcg    816
Asn Asp Arg Ser Asp Val Pro Glu Leu Leu Asn Phe Glu Cys Gly Ala
        260                 265                 270 gat tat gtg aag act aac cag aga tta ccc aag ggt ctt tct cca tcc    864
Asp Tyr Val Lys Thr Asn Gln Arg Leu Pro Lys Gly Leu Ser Pro Ser
    275                 280                 285 tcg ttt gat tcg cta tat tgc tcc ttt gat ggt gac gca gac agg gtt    912
Ser Phe Asp Ser Leu Tyr Cys Ser Phe Asp Gly Asp Ala Asp Arg Val
290                 295                 300 gtg ttc tac tat gtc gac tca gga tca aaa ttt cat ttg ttg gat ggt    960
Val Phe Tyr Tyr Val Asp Ser Gly Ser Lys Phe His Leu Leu Asp Gly
305                 310                 315                 320 gac aaa att tcc act ttg ttt gca aag ttc ttg tct aaa caa cta gaa   1008
Asp Lys Ile Ser Thr Leu Phe Ala Lys Phe Leu Ser Lys Gln Leu Glu
            325                 330                 335 ttg gca cac cta gaa cat tct ttg aag att ggt gtt gtg caa act gcc   1056
Leu Ala His Leu Glu His Ser Leu Lys Ile Gly Val Val Gln Thr Ala
        340                 345                 350 tat gca aac ggc agt tcc acc gct tac ata aaa aat acg ttg cac tgt   1104
Tyr Ala Asn Gly Ser Ser Thr Ala Tyr Ile Lys Asn Thr Leu His Cys
    355                 360                 365 ccc gtg tct tgc act aag aca ggt gtt aaa cac ttg cat cat gaa gct   1152
Pro Val Ser Cys Thr Lys Thr Gly Val Lys His Leu His His Glu Ala
370                 375                 380 gcc act cag tac gat att ggc att tat ttc gaa gca aat gga cat ggt   1200
Ala Thr Gln Tyr Asp Ile Gly Ile Tyr Phe Glu Ala Asn Gly His Gly
385                 390                 395                 400 acg att ata ttc agc gaa aaa ttt cat cga act atc aaa tct gaa tta   1248
Thr Ile Ile Phe Ser Glu Lys Phe His Arg Thr Ile Lys Ser Glu Leu
            405                 410                 415 tcc aag tcc aag tta aat ggt gat acg tta gct ttg aga act ttg aag   1296
Ser Lys Ser Lys Leu Asn Gly Asp Thr Leu Ala Leu Arg Thr Leu Lys
        420                 425                 430 tgt ttc tct gaa ttg att aat cag acc gtg gga gat gct att tca gac   1344
Cys Phe Ser Glu Leu Ile Asn Gln Thr Val Gly Asp Ala Ile Ser Asp
    435                 440                 445 atg ctt gct gtc ctt gct act ttg gcg att ttg aaa atg tcg cca atg   1392
Met Leu Ala Val Leu Ala Thr Leu Ala Ile Leu Lys Met Ser Pro Met
450                 455                 460 gat tgg gat gaa gag tat act gat ttg ccc aac aag ctg gtt aag tgc   1440
Asp Trp Asp Glu Glu Tyr Thr Asp Leu Pro Asn Lys Leu Val Lys Cys
465                 470                 475                 480 atc gtt cct gat agg tca att ttc caa acc acg gac cag gaa aga aaa   1488
Ile Val Pro Asp Arg Ser Ile Phe Gln Thr Thr Asp Gln Glu Arg Lys
```

```
                        485                 490                 495
ttg ctc aat cca gtg ggg ttg caa gac aag ata gat ctt gtg gta gcc      1536
Leu Leu Asn Pro Val Gly Leu Gln Asp Lys Ile Asp Leu Val Val Ala
            500                 505                 510 aag tat ccc atg gga aga agc ttt gtc aga gcc agt ggt acg gag gat      1584
Lys Tyr Pro Met Gly Arg Ser Phe Val Arg Ala Ser Gly Thr Glu Asp
            515                 520                 525 gcg gtg agg gtt tat gcg gaa tgt aag gac tcc tct aag tta ggt caa      1632
Ala Val Arg Val Tyr Ala Glu Cys Lys Asp Ser Ser Lys Leu Gly Gln
            530                 535                 540 ttt tgt gac gaa gtg gtg gag cac gtt aag gca tct gct tga              1674
Phe Cys Asp Glu Val Val Glu His Val Lys Ala Ser Ala
545                 550                 555
```

<210> SEQ ID NO 30
<211> LENGTH: 557
<212> TYPE: PRT
<213> ORGANISM: Saccharomyces cerevisiae

<400> SEQUENCE: 30

```
Met Lys Val Asp Tyr Glu Gln Leu Cys Lys Leu Tyr Asp Asp Thr Cys
1               5                   10                  15

Arg Thr Lys Asn Val Gln Phe Ser Tyr Gly Thr Ala Gly Phe Arg Thr
            20                  25                  30

Leu Ala Lys Asn Leu Asp Thr Val Met Phe Ser Thr Gly Ile Leu Ala
        35                  40                  45

Val Leu Arg Ser Leu Lys Leu Gln Gly Gln Tyr Val Gly Val Met Ile
    50                  55                  60

Thr Ala Ser His Asn Pro Tyr Gln Asp Asn Gly Val Lys Ile Val Glu
65                  70                  75                  80

Pro Asp Gly Ser Met Leu Leu Ala Thr Trp Glu Pro Tyr Ala Met Gln
                85                  90                  95

Leu Ala Asn Ala Ala Ser Phe Ala Thr Asn Phe Glu Glu Phe Arg Val
            100                 105                 110

Glu Leu Ala Lys Leu Ile Glu His Glu Lys Ile Asp Leu Asn Thr Thr
        115                 120                 125

Val Val Pro His Ile Val Val Gly Arg Asp Ser Arg Glu Ser Ser Pro
    130                 135                 140

Tyr Leu Leu Arg Cys Leu Thr Ser Ser Met Ala Ser Val Phe His Ala
145                 150                 155                 160

Gln Val Leu Asp Leu Gly Cys Val Thr Thr Pro Gln Leu His Tyr Ile
                165                 170                 175

Thr Asp Leu Ser Asn Arg Arg Lys Leu Glu Gly Asp Thr Ala Pro Val
            180                 185                 190

Ala Thr Glu Gln Asp Tyr Tyr Ser Phe Phe Ile Gly Ala Phe Asn Glu
        195                 200                 205

Leu Phe Ala Thr Tyr Gln Leu Glu Lys Arg Leu Ser Val Pro Lys Leu
    210                 215                 220

Phe Ile Asp Thr Ala Asn Gly Ile Gly Gly Pro Gln Leu Lys Lys Leu
225                 230                 235                 240

Leu Ala Ser Glu Asp Trp Asp Val Pro Ala Glu Gln Val Glu Val Ile
                245                 250                 255

Asn Asp Arg Ser Asp Val Pro Glu Leu Leu Asn Phe Glu Cys Gly Ala
            260                 265                 270

Asp Tyr Val Lys Thr Asn Gln Arg Leu Pro Lys Gly Leu Ser Pro Ser
        275                 280                 285
```

```
Ser Phe Asp Ser Leu Tyr Cys Ser Phe Asp Gly Asp Ala Asp Arg Val
    290                 295                 300
Val Phe Tyr Tyr Val Asp Ser Gly Ser Lys Phe His Leu Leu Asp Gly
305                 310                 315                 320
Asp Lys Ile Ser Thr Leu Phe Ala Lys Phe Leu Ser Lys Gln Leu Glu
                325                 330                 335
Leu Ala His Leu Glu His Ser Leu Lys Ile Gly Val Val Gln Thr Ala
            340                 345                 350
Tyr Ala Asn Gly Ser Ser Thr Ala Tyr Ile Lys Asn Thr Leu His Cys
        355                 360                 365
Pro Val Ser Cys Thr Lys Thr Gly Val Lys His Leu His His Glu Ala
370                 375                 380
Ala Thr Gln Tyr Asp Ile Gly Ile Tyr Phe Glu Ala Asn Gly His Gly
385                 390                 395                 400
Thr Ile Ile Phe Ser Glu Lys Phe His Arg Thr Ile Lys Ser Glu Leu
                405                 410                 415
Ser Lys Ser Lys Leu Asn Gly Asp Thr Leu Ala Leu Arg Thr Leu Lys
            420                 425                 430
Cys Phe Ser Glu Leu Ile Asn Gln Thr Val Gly Asp Ala Ile Ser Asp
        435                 440                 445
Met Leu Ala Val Leu Ala Thr Leu Ala Ile Leu Lys Met Ser Pro Met
450                 455                 460
Asp Trp Asp Glu Glu Tyr Thr Asp Leu Pro Asn Lys Leu Val Lys Cys
465                 470                 475                 480
Ile Val Pro Asp Arg Ser Ile Phe Gln Thr Thr Asp Gln Glu Arg Lys
                485                 490                 495
Leu Leu Asn Pro Val Gly Leu Gln Asp Lys Ile Asp Leu Val Val Ala
            500                 505                 510
Lys Tyr Pro Met Gly Arg Ser Phe Val Arg Ala Ser Gly Thr Glu Asp
        515                 520                 525
Ala Val Arg Val Tyr Ala Glu Cys Lys Asp Ser Ser Lys Leu Gly Gln
530                 535                 540
Phe Cys Asp Glu Val Val Glu His Val Lys Ala Ser Ala
545                 550                 555

<210> SEQ ID NO 31
<211> LENGTH: 14
<212> TYPE: PRT
<213> ORGANISM: Artificial Sequence
<220> FEATURE:
<223> OTHER INFORMATION: Amino acid residues 111-124 of SEQ ID NO: 11
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid

<400> SEQUENCE: 31

Gly Gly Gln Xaa Thr Arg Leu Gly Xaa Xaa Xaa Pro Lys Gly
1               5                   10

<210> SEQ ID NO 32
<211> LENGTH: 10
<212> TYPE: PRT
<213> ORGANISM: Artificial Sequence
<220> FEATURE:
```

```
<223> OTHER INFORMATION: Amino acid residues 219-228 of SEQ ID NO: 11
<220> FEATURE:
<221> NAME/KEY: misc_feature
<222> LOCATION: (2)..(2)
<223> OTHER INFORMATION: Xaa can be Asp or Asn
<220> FEATURE:
<221> NAME/KEY: misc_feature
<222> LOCATION: (5)..(5)
<223> OTHER INFORMATION: Xaa can be Gly or Ala
<220> FEATURE:
<221> NAME/KEY: misc_feature
<222> LOCATION: (7)..(9)
<223> OTHER INFORMATION: Xaa can be any naturally occurring amino acid

<400> SEQUENCE: 32

Pro Xaa Gly Asn Xaa Gly Xaa Xaa Xaa Ala
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Amino acid residues 377-386 of SEQ ID NO: 11
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 33

Lys Xaa Glu Xaa Phe Xaa Phe Asp Xaa Phe
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Prokaryote conserved domain from UDP-GlcNAc
      pyrophosphorylase
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can Arg or Ser
<220> FEATURE:
<221> NAME/KEY: misc_feature
<222> LOCATION: (6)..(9)
<223> OTHER INFORMATION: Xaa can be any naturally occurring amino acid

<400> SEQUENCE: 34

Gly Xaa Gly Thr Xaa Xaa Xaa Xaa Xaa Pro Lys
1               5                   10
```

PLANTS WHICH SYNTHESIZE INCREASED AMOUNTS OF GLUCOSAMINOGLYCANS

CROSS-REFERENCE TO RELATED APPLICATIONS

This application is the U.S. National Stage application of International Application No. PCT/EP2008/007837, filed Sep. 11, 2008, which claims priority to EP 07116174.9, filed Sep. 12, 2007 and U.S. Provisional Patent Application No. 60/993,575, filed Sep. 13, 2007, the disclosures of each of which are hereby incorporated by reference.

BACKGROUND OF THE INVENTION (i) Field of the Invention

The present invention relates to plant cells and plants which synthesize an increased amount of glucosaminoglycans, and to methods for preparing such plants, and also to methods for preparing glucosaminoglycans with the aid of these plant cells or plants. Here, plant cells or genetically modified plants according to the invention have glucosaminoglycan synthase activity and additionally an increased glucosamine 6-phosphate acetyltransferase activity and an increased UDP-N-acetyl-glucosamine pyrophosphorylase activity compared to wild-type plant cells or wild-type plants. The present invention furthermore relates to compositions comprising plant cells having an increased glucosaminoglycan synthesis.

(ii) Description of the Related Art

Proteoglycans, a class of glycoproteins, are inter alia an essential component of cartilage and have, attached to a core protein, glucosaminoglycans composed of repetitive disaccharide units. The repetitive disaccharide units for their part are, via a characteristic carbohydrate binding sequence, attached covalently to the core protein. Depending on the composition of the disaccharide units, a distinction is made inter alia between the glucosaminoglycans heparan/heparin sulfate, keratan sulfate and chondroitin/dermatan sulfate whose disaccharide units each contain a molecule which is glucosamine or a glucosamine derivative.

Hyaluronan, a further glucosaminoglycan, also has a derivative of glucosamine acetyl-glucosamine) as one of the components of its disaccharide unit, but, in nature, is not attached to proteins. Except for hyaluronan, the glucosaminoglycans mentioned are naturally sulfated polymers. In these substances, sulfate groups are introduced at various atoms or substituents of the disaccharide units so that the substances mentioned are not uniform polymers but groups of polymers summarized under the respective generic term. The individual molecules of the polymer groups in question may differ both in the degree of sulfatation and in the position of the monomers having sulfate groups.

Hyaluronan is a naturally occurring unbranched, linear mucopolysaccharide (glucosaminoglycan) which is constructed of alternating molecules of glucuronic acid (GlcA) and N-acetyl-glucosamine (GlcNAc). The basic building block of hyaluronan consists of the disaccharide glucuronic acid-beta-1,3-N-acetyl-glucosamine. In hyaluronan, these repeating units are attached to one another via beta-1,4 linkages. In pharmacy, use is frequently made of the term hyaluronic acid. Since hyaluronan is in most cases present as a polyanion and not as the free acid, hereinbelow, the term hyaluronan is preferably used, but each term is to be understood as embracing both molecular forms.

Hyaluronan has unusual physical chemical properties, such as, for example, properties of polyelectrolytes, viscoelastic properties, a high capacity to bind water, properties of gel formation, which, in addition to further properties of hyaluronan, are described in a review article by Lapcik et al. (1998, Chemical Reviews 98(8), 2663-2684).

Hyaluronan is a component of extracellular connective tissue and bodily fluids of vertebrates. In humans, hyaluronic acid is synthesized by the cell membrane of all body cells, especially mesenchymal cells, and ubiquitously present in the body with a particularly high concentration in the connective tissues, the extracellular matrix, the umbilical cord, the joint fluid, the cartilaginous tissue, the skin and the vitreous body of the eye (Bernhard Gebauer, 1998, Inaugural-Dissertation, Virchow-Klinikum Medizinische Fakultät Charité der Humboldt Universität zu Berlin; Fraser et al., 1997, Journal of Internal Medicine 242, 27-33).

Recently, hyaluronan was also found in animal non-vertebrate organisms (molluscs) (Volpi and Maccari, 2003, Biochimie 85, 619-625).

Furthermore, some human pathogenic gram-positive bacteria (Streptococcus group A and C) and gram-negative bacteria (Pasteurella) synthesize hyaluronan as exopolysaccharides which protect these bacteria against attack by the immune system of their host, since hyaluronan is a non-immunogenic substance.

Viruses which infect single-cell green algae of the genus Chlorella, some of which are present as endosymbionts in Paramecium species, bestow upon the single-cell green algae the ability to synthesize hyaluronan after infection by the virus (Graves et al., 1999, Virology 257, 15-23). However, the ability to synthesize hyaluronan is not a feature which characterizes the algae in question. The ability of the algae to synthesize hyaluronan is mediated by an infection with a virus whose genome has a sequence coding for hyaluronan synthase (DeAngelis, 1997, Science 278, 1800-1803).

The catalysis of the hyaluronan synthesis is effected by a single membrane-integrated or membrane-associated enzyme, hyaluronan synthase.

The mechanism of the transfer of synthesized hyaluronan molecules across the cytoplasma membrane into the medium surrounding the cell has not yet been fully elucidated. Earlier hypotheses assumed that transport across the cell membrane was effected by hyaluronan synthase itself. However, more recent results indicate that the transport of hyaluronan molecules across the cytoplasma membrane takes place by energy-dependent transport via transport proteins responsible for this action. Thus, Streptococcus strains were generated by mutation in which the synthesis of an active transport protein was inhibited. These strains synthesized less hyaluronan than corresponding wild-type bacteria strains (Ouskova et al., 2004, Glycobiology 14(10), 931-938). In human fibroblasts, it was possible to demonstrate, with the aid of agents specifically inhibiting known transport proteins, that it is possible to reduce both the amount of hyaluronan produced and the activity of hyaluronan synthases (Prehm and Schumacher, 2004, Biochemical Pharmacology 68, 1401-1410). In which amount, if at all, transport proteins capable of transporting hyaluronan are present in plants is not known.

The unusual properties of hyaluronan offer a wealth of possibilities for application in various fields, such as, for example, pharmacy, the cosmetics industry, in the production of food and feed, in technical applications (for example as lubricants), etc. The most important applications where hyaluronan is currently being used are in the medicinal and cosmetics field (see, for example, Lapcik et al., 1998, Chemical Reviews 98(8), 2663-2684, Goa and Benfield, 1994, Drugs 47(3), 536-566).

In the medical field, hyaluronan-containing products are currently used for the intraarticular treatment of arthrosis and in ophthalmics used for eye surgery. Hyaluronan is also used for treating joint disorders in racehorses. In addition, hyaluronan is a component of some rhinologics which, for example in the form of eye drops and nasalia, serve to moisten dry mucous membranes. Hyaluronan-containing solutions for injection are used as analgesics and antirheumatics. Patches comprising hyaluronan or derivatized hyaluronan are employed in wound healing. As dermatics, hyaluronan-containing gel implants are used for correcting skin deformations in plastic surgery.

For pharmacological applications, preference is given to using hyaluronan having a high molecular weight.

In cosmetic medicine, hyaluronan preparations are among the most suitable skin filler materials. By injecting hyaluronan, for a limited period of time, it is possible to smooth wrinkles or to increase the volume of lips.

In cosmetic products, in particular in skin creams and lotions, hyaluronan is frequently used as moisturizer by virtue of its high water-binding capacity.

Furthermore, hyaluronan-containing preparations are sold as so-called nutraceuticals (food supplements) which can also be used in animals (for example dogs, horses) for the prophylaxis and alleviation of arthrosis.

Hyaluronan used for commercial purposes is currently isolated from animal tissues (cockscombs) or prepared fermentatively using bacterial cultures.

U.S. Pat. No. 4,141,973 describes a process for isolating hyaluronan from cockscombs or alternatively from umbilical cords. In addition to hyaluronan, animal tissues (for example cockscombs, umbilical cords) also contain further mucopolysaccharides related to hyaluronan, such as chondrotin sulfate, dermatan sulfate, keratan sulfate, heparan sulfate and heparin. Furthermore, animal organisms contain proteins (hyaladherins) which bind specifically to hyaluronan and which are required for the most different functions in the organism, such as, for example, the degradation of hyaluronan in the liver, the function of hyaluronan as lead structure for cell migration, the regulation of endocytosis, the anchoring of hyaluronan on the cell surface or the formation of hyaluronan networks (Turley, 1991, Adv Drug Delivery Rev 7, 257 ff.; Laurent and Fraser, 1992, FASEB J. 6, 183 ff.; Stamenkovic and Aruffo, 1993, Methods Enzymol. 245, 195 if; Knudson and Knudson, 1993, FASEB 7, 1233 ff.).

The *Streptococcus* strains used for the bacterial production of hyaluronan are exclusively bacteria pathogenic to humans. During cultivation, too, these bacteria produce (pyrogenic) exotoxins and hemolysins (streptolysin, in particular alpha- and beta-hemolysin) Kilian, M.: *Streptococcus* and *Enterococcus*. In: *Medical Microbiology*. Greenwood, D.; Slack, R C A; Peutherer, J. F. (Eds.). Chapter 16. Churchill Livingstone, Edinburgh, UK: pp. 174-188, 2002, ISBN 0443070776) which are released into the culture medium. This renders purification and isolation of the hyaluronan prepared with the aid of *Streptococcus* strains more difficult. In particular for pharmaceutical application, the presence of exotoxins and hemolysins in the preparation is a problem.

U.S. Pat. No. 4,801,539 describes the preparation of hyaluronan by fermentation of a mutagenized bacterial strain (*Streptococcus zooedemicus*). The mutagenized bacteria strain used no longer synthesizes beta-hemolysin. The yield achieved was 3.6 g of hyaluronan per liter of culture.

EP 0694616 describes a method for cultivating *Streptococcus zooedemicus* or *Streptococcus equi*, where, under the culture conditions employed, no streptolysin, but increased amounts of hyaluronan are synthesized. The yield achieved was 3.5 g of hyaluronan per liter of culture.

During cultivation, *Streptococcus* strains release the enzyme hyaluronidase into the culture medium, as a consequence of which, in this production system, too, the molecular weight is reduced during purification. The use of hyaluronidase-negative *Streptococcus* strains or of methods for the production of hyaluronan where the production of hyaluronidase during cultivation is inhibited are described in U.S. Pat. No. 4,782,046. The yield achieved was up to 2.5 g of hyaluronan per liter of culture, and the maximum mean molecular weight achieved was $3.8 \times 10^6$ Da, at a molecular weight distribution of from $2.4 \times 10^6$ to $4.0 \times 10^6$.

US 20030175902 and WO 03 054163 describe the preparation of hyaluronan with the aid of heterologous expression of a hyaluronan synthase from *Streptococcus equisimilis* in *Bacillus subtilis*. To achieve the production of sufficient amounts of hyaluronan, in addition to heterologous expression of a hyaluronan synthase, simultaneous expression of a UDP-glucose dehydrogenase in the *Bacillus* cells is also required. US 20030175902 and WO 03 054163 do not state the absolute amount of hyaluronan obtained in the production with the aid of *Bacillus subtilis*. The maximum mean molecular weight achieved was about $4.2 \times 10^6$. However, this mean molecular weight was only achieved for the recombinant *Bacillus* strain where a gene coding for the hyaluronan synthase gene from *Streptococcus equisimilis* and the gene coding for the UDP-glucose dehydrogenase from *Bacillus subtilis* were integrated into the *Bacillus subtilis* genome under the control of the amyQ promoter, where at the same time the *Bacillus subtilis*-endogenous cxpY gene (which codes for a cytochrome P450 oxidase) was inactivated. Chien and Lee (2007, Biotechnol. Prog. Online publication, ASAP Article 10.1021/bp070036w, S8756-7938(07)00036-7) describe various recombinant *Baciullus subtilis* strains. One strain, which had been transformed with a nucleic acid sequence coding for a hyaluronan synthase and a nucleic acid sequence coding for a UDP-glucose dehydrogenase, synthesized at most 1.14 g/l of hyaluronan. A strain which, in addition to the nucleic acid sequences just mentioned, had been transformed with a nucleic acid sequence coding for *Vitreoscilla* hemoglobin synthesized 1.8 g/l hyaluronan.

WO 06 032538 describes transgenic plants transformed with nucleic acid molecules coding for hyaluronan synthases. The synthesis of hyaluronan in the plants in question was demonstrated unambiguously.

WO 05 012529 describes the production of transgenic tobacco plants which were transformed using nucleic acid molecules coding for hyaluronan synthases from *Chlorella*-infecting viruses. In WO 05 012529, use was made, on the one hand, of nucleic acid sequences coding for hyaluronan synthase of the *Chlorella* virus strain CVH1 and, on the other hand, of the *Chlorella* virus strain CVKA1 for transforming tobacco plants. The synthesis of hyaluronan could only be demonstrated for a plant transformed with a nucleic acid coding for a hyaluronan synthase isolated from the *Chlorella* virus strain CVKA1. For tobacco plants transformed with a nucleic acid sequence coding for a hyaluronan synthase isolated from the *Chlorella* virus strain CVH1, it was not possible to detect hyaluronan synthesis in the corresponding transgenic plants. The amount of hyaluronan synthesized by the only hyaluronan-producing transgenic tobacco plant in WO 05 012529 is stated as being about 4.2 μg of hyaluronan per ml of measured volume which, taking into account the description for carrying out the experiment in question, corresponds approximately to an amount of at most 12 μg of hyaluronan produced per gram of fresh weight of plant material.

WO 2007 039314 describes transgenic plants having the activity of a hyaluronan synthase and additionally an increased glutamine:fructose 6-phosphate amidotransferase (GFAT) activity. These plants synthesize an increased amount of hyaluronan compared to plants having only the activity of a hyaluronan synthase. The maximum amount of hyaluronan synthesized by these tobacco plants is about 0.03% per gram of fresh weight of plant material used for the measurement (see FIG. 5 in WO 2007 039316).

WO 2007 039316 describes transgenic plants having the activity of a hyaluronan synthase and additionally an increased glutamine:fructose 6-phosphate amidotransferase (GFAT) activity and an increased UDP-Glucose dehydrogenase (UDP-Glc-DH) activity compared to wild-type plants. These plants synthesize an increased amount of hyaluronan compared to plants having the activity of a hyaluronan synthase and at the same time the activity of a protein having the activity of a GFAT. The maximum amount of hyaluronan synthesized by these tobacco plants is 0.2% per gram of fresh weight of plant material used for the measurement (see FIG. 6 in WO 2007 039316).

Furthermore, WO 2007 039316 contains a list of proteins which can be expressed in plants cells to increase further the amount of synthesized hyaluronan in plant cells. The proteins proposed in WO 2007 039316 are a random list of enzymes which, in various organisms, are involved in the synthesis of UDP-GlcNAc. The proteins listed in WO 2007 039316 have various enzymatic functions. WO 2007 039316 gives no indication whether and which of the enzymes listed may indeed increase the hyaluronan content when expressed in transgenic plants.

The synthesis of the disaccharide chain of the chondroitin/dermatan ([beta-1,4)]-[glucuronic acid-beta-1,4-N-acetyl-galactosamine]) is catalyzed by a chondroitin synthase starting from UDP-glucuronic acid (UDP-GlcA) and UDP-N-acetyl-galactosamine (UDP-GalNAc), an epimer of UDP-N-acetyl-glucosamine (UDP-GlcNAc) (Kitagawa et al., 2001, J Biol Chem 276(42), 38721-38726). By an epimerase, the glucuronic acid molecules of the chondroitin can be converted into iduronic acid. If more than 10% of the glucuronic acid molecules are present as iduronic acid, the polymer is referred to as dermatan. The introduction of the sulfate groups at various positions of the disaccharide chain of the chondroitin or the dermatan is then catalyzed by other enzymes, resulting in the formation of chondroitin/dermatan sulfate. Here, the degree of sulfatation may differ from molecule to molecule.

For some time, chondroitin sulfate has been discussed as a potential active compound for the treatment of osteoarthritis (Clegg et al., 2006, The New England Journal of Medicine 354(8), 795-808).

The synthesis of the disaccharide chain of the heparin/heparan (heparosans) ([alpha-1,4]-[glucuronic acid-beta-1,4-glucosamine], or [alpha-1,4]-[iduronic acid-alpha-1,4-glucosamine]$_n$) is catalyzed by a heparin/heparosan synthase starting from UDP-GlcA and UDP-GlcNAc (DeAngelis and White, 2004, J. Bacteriology 186(24), 8529-8532). The glucuronic acid molecules of the heparosan can be converted by an epimerase into iduronic acid. The introduction of the sulfate groups at various positions of the disaccharide chain of the heparosan is then catalyzed by other enzymes, resulting in the formation of heparin or heparan sulfate. Heparin sulfate has a considerably higher substitution by sulfate groups than heparan sulfate. Heparin sulfate has about 90% iduronic acid molecules, whereas in heparan sulfate the glucuronic acid molecules predominate (Gallagher et al., 1992, Int. J. Biochem 24, 553-560). As in the case of chondroitin/dermatan sulfate, in the case of heparin/heparan sulfate, too, the degree of sulfatation may differ from molecule to molecule.

Heparin sulfate is used inter alia as an anticoagulant, for example for preventing and treating thromboses.

Currently, chondroitin/dermatan sulfat and heparin/heparan sulfate are prepared by isolation from animal tissue. Chondroitin sulfate is isolated mainly from bovine cartillage or shark cartillage, heparin/heparan sulfate is isolated from porcine intestine or bovine lungs. Since the disaccharide chains of chondroitin/dermatan sulfate and heparin/heparan sulfate have no uniform sulfatation pattern, it is difficult to obtain a uniform specific product. Accordingly, the product is always a mixture of molecules having various degrees of sulfatation.

As already described, glucosaminoglycans, such as, for example, chondroitin sulfate or heparin/heparan sulfate are currently isolated from animal tissues. In addition to the desired substances, these tissues also contain other glucosaminoglycans. The separation of the individual glucosaminoglycans, if possible at all, is difficult and expensive. Furthermore, the potential contamination of animal tissues by pathogenic microorganisms and/or by other substance such as, for example, BSE or the bird flu pathogen, which may lead to diseases in man, poses a problem when using glucosaminoglycans isolated from animal tissue. In patients, the use of medicinal preparations contaminated by animal proteins can result in unwanted immunological reactions of the body (for hyaluronan preparations see, for example, U.S. Pat. No. 4,141,973), in particular if the patient is allergic to animal proteins.

In addition, substances prepared from animal raw materials are unacceptable for some ways of life such as, for example, vegans or for koscher food preparation.

A further problem in the isolation of glucosaminoglycans from animal tissues consists in effect that frequently the molecular weight of glucosaminoglycans is reduced during purification since animal tissues also contain glucosaminoglycan-degrading enzymes.

The amounts (yields) of glucosaminoglycans which can be obtained in satisfactory quality and purity from animal tissues are low (for example hyaluronan from cockscomb: 0.079% w/w, EP 0144019, U.S. Pat. No. 4,782,046), which means that large amounts of animal tissues have to be processed.

The production of glucosaminoglycans by fermentation of bacteria strains is associated with high costs, since the bacteria have to be fermented in sealed sterile containers under expensive controlled culture conditions (see, for example, for hyaluronan, U.S. Pat. No. 4,897,349). Furthermore, the amount of glucosaminoglycans which can be produced by fermentation of bacteria strains is limited by the production facilities present in each case. Here, it also has to be taken into account that fermenters, as a consequence of physical laws, cannot be built for excessively large culture volumes. Particular mention may be made here of homogeneous mixing of the substances fed in from the outside (for example essential nutrient sources for bacteria, reagents for regulating the pH, oxygen) with the culture medium required for efficient production, which, in large fermenters, can be ensured only with great technical expenditure, if at all.

Plants do not naturally produce glucosaminoglycans such as, for example, hyaluronan, heparan/heparin sulfate, keratan sulfate or chondroitin/dermatan sulfate. Naturally occurring plants themselves do not have any nucleic acids in their genome which code for proteins catalyzing the synthesis of glucosaminoglycans, and, although a large number of plant carbohydrates have been described and characterized, it has hitherto not been possible to detect any of the glucosaminoglycans mentioned in non-infected natural plant cells (Graves et al., 1999, Virology 257, 15-23).

WO 98 35047 (U.S. Pat. No. 6,444,878) describes a metabolic path for the synthesis of GlcNAc in plant cells where glucosamine is converted via a plurality of successive enzymatically catalyzed reaction steps with formation of the metabolites GlcNAc, N-acetyl-glucosamine 6-phosphate and N-acetyl-glucosamine 1-phosphate into UDP-GlcNAc. In higher concentrations, glucosamine 6-phosphate is toxic for plant cells (WO 98 35047).

An alternative metabolic path described for plants comprises the reaction of fructose 6-phosphate and glutamine giving glucosamine 6-phosphate which is subsequently converted by a number of successive enzymatically catalyzed reaction steps with formation of the metabolites glucosamine 1-phosphate and N-acetyl-glucosamine 1-phosphate into UDP-GlcNAc (Mayer et al., 1968, Plant Physiol. 43, 1097-1107).

To date, it is still not clear which protein activities have to be modified in the metabolic path for the synthesis of UDP-GlcNAc in the plant for the plants to synthesize increased amounts of glucosaminoglycans.

SUMMARY OF THE INVENTION

Accordingly, it is the object of the present invention to provide alternative means and processes for preparing efficient amounts of glucosaminoglycans in plants.

DETAILED DESCRIPTION OF THE INVENTION

This object is achieved by the embodiments referred to in the claims.

Surprisingly, it has been found that genetically modified plant cells or genetically modified plants comprising a nucleic acid molecule coding for a glucosaminoglycan synthase and additionally comprising a foreign nucleic acid molecule coding for a protein having the activity of a glucosamine 6-phosphate acetyltransferase and a foreign nucleic acid molecule coding for a protein comprising the activity of a monofunctional UDP-N-acetyl-glucosamine pyrophosphorylase produce significantly higher amounts of glucosaminoglycan than plant cells or plants having (only) the activity of a glucosaminoglycan synthase.

Thus, the present invention relates to genetically modified plant cells or genetically modified plants comprising a foreign nucleic acid molecule coding for a glucosaminoglycan synthase, characterized in that said genetically modified plant cells or said genetically modified plants additionally comprise a foreign nucleic acid molecule coding for a protein having the activity of a glucosamine 6-phosphate acetyltransferase and a foreign nucleic acid molecule coding for a protein having the activity of a monofunctional UDP-N-acetyl-glucosamine pyrophosphorylase.

The production of glucosaminoglycans by fermentation of bacteria strains is associated with high costs, since the bacteria have to be fermented in sealed sterile containers under expensive controlled culture conditions (see, for example, U.S. Pat. No. 4,897,349). Furthermore, the amount of glucosaminoglycans which can be produced by fermentation of bacteria strains is limited by the production facilities present in each case. The high price of, for example, hyaluronan which is currently commercially available means that this glucosaminoglycan, in spite of its special properties (for example viscoelastic properties, a high capacity to bind water), is not available for industrial applications.

Thus, compared to known means for producing glucosaminoglycans, plant cells according to the invention and plants according to the invention offer the advantage that they synthesize increased amounts of glucosaminoglycans (for example hyaluronan) compared to plant cells or plants comprising only the activity of a glucosaminoglycan synthase.

Here, the genetic modification of genetically modified plant cells according to the invention or genetically modified plants according to the invention can be any genetic modification resulting in an integration of a foreign nucleic acid molecule encoding for a glucosamine synthase and an integration of a foreign nucleic acid molecule coding for a protein having the activity of a glucosamine 6-phosphate acetyltransferase and an integration of a foreign nucleic acid molecule coding for a protein having the activity of a monofunctional UDP-N-acetyl-glucosamine pyrophosphorylase into a plant cell or a plant.

In the context of the present invention, the term "glucosaminoglycan synthase" is to be understood as meaning a protein which synthesizes glucosaminoglycan from the substrates UDP-glucuronic acid (UDP-GlcA) and UDP-N-acetyl-aldohexsosamine (UDP-AldohexNAc). The catalysis of the glucosaminoglycans takes place according to the general reaction scheme below:

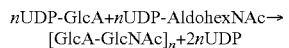

$n$UDP-GlcA+$n$UDP-AldohexNAc→
[GlcA-GlcNAc]$_n$+2$n$UDP

Preferably, the UDP-N-acetyl-aldohexsosamine prepared in the above reaction sequence is UDP-N-acetyl-glucosamine or UDP-N-acetyl-galactosamine.

In a preferred embodiment, the present invention relates to plant cells according to the invention or plants according to the invention where the foreign nucleic acid molecule coding for a glucosaminoglycan synthase is coding for a hyaluronan synthase or a chondroitin synthase or a heparin/heparosan synthase.

In the context of the present invention, the term "hyaluronan synthase" (EC 2.4.1.212) is to be understood as meaning a protein which synthesizes hyaluronan from the substrates UDP-glucuronic acid (UDP-GlcA) and UDPN-acetyl-glucosamine (UDP-GlcNAc). The synthesis of hyaluronan is catalyzed according to the reaction scheme below:

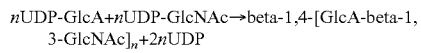

$n$UDP-GlcA+$n$UDP-GlcNAc→beta-1,4-[GlcA-beta-1,3-GlcNAc]$_n$+2$n$UDP

The hyaluronan synthases which have hitherto been studied can be classified into two groups: hyaluronan synthases of Class I and hyaluronan synthases of Class II (DeAngelis, 1999, CMLS, Cellular and Molecular Life Sciences 56, 670-682).

The hyaluronan synthases from vertebrates are distinguished further by the isoenzymes identified. The various isoenzymes are referred to by Arab numerals in the order of their identification (for example hsHAS1, hsHAS2, hsHAS3).

Nucleic acid molecules and corresponding protein sequences coding for hyaluronan synthases have been described, inter alia, for the following organisms: rabbit (*Oryctolagus cuniculus*) ocHas2 (EMBL AB055978.1, US 20030235893), ocHas3 (EMBL AB055979.1, US 20030235893); baboon (*Papio anubis*) paHas1 (EMBL AY463695.1); frog (*Xenopus laevis*) xlHas1 (EMBL M22249.1, US 20030235893), xlHas2 (DG42) (EMBL AF168465.1), xlHas3 (EMBL AY302252.1); human (*Homo sapiens*) hsHAS1 (EMBL D84424.1, US 20030235893), hsHAS2 (EMBL U54804.1, US 20030235893), hsHAS3 (EMBL AF232772.1, US 20030235893); mouse (*Mus musculus*), mmHas1 (EMBL D82964.1, US 20030235893), mmHAS2 (EMBL U52524.2, US 20030235893), mmHas3 (EMBL U86408.2, US 20030235893); cattle (*Bos taurus*) btHas2 (EMBL AJ004951.1, US 20030235893); chicken (*Gallus gallus*) ggHas2 (EMBL AF106940.1, US 20030235893); rat (*Rattus norvegicus*) rnHas 1 (EMBL AB097568.1, Itano et al., 2004, J. Biol. Chem. 279(18) 18679-18678), rnHas2 (EMBL AF008201.1); rnHas 3 (NCBI NM__172319.1, Itano et al., 2004, J. Biol. Chem. 279(18) 18679-18678), horse (*Equus caballus*) ecHAS2 (EMBL AY056582.1, GI:23428486), pig (*Sus scrofa*) sscHAS2 (NCBI NM__214053.1, GI:47522921), sscHas 3 (EMBLAB159675), zebra fish (*Danio rerio*) brHas1 (EMBL AY437-407), brHas2 (EMBL AF190742.1) brHas3 (EMBL AF190743.1); *Pasteurella multocida* pmHas (EMBL AF036004.2); *Streptococcus pyogenes* spHas (EMBL, L20853.1, L21187.1, U.S. Pat. No. 6,455,304, US 20030235893); *Streptococcus equis* seHas (EMBL AF347022.1, AY173078.1), *Streptococcus uberis* suHasA (EMBL AJ242946.2, US 20030235893), *Streptococcus equisimilis* seqHas (EMBL AF023876.1, US 20030235893); *Sulfolobus solfataricus* ssHAS (US 20030235893), *Sulfolobus tokodaii* stHas (AP000988.1), *Paramecium bursaria Chlorella* virus 1, cvHAS (EMBL U42580.3, PB42580, US 20030235893).

In a preferred embodiment, the present invention relates to genetically modified plant cells according to the invention or genetically modified plants according to the invention where the foreign nucleic acid molecule coding for a glucosaminoglycan synthase is characterized in that it codes for a hyaluronan synthase. The foreign nucleic acid molecule in question coding for a hyaluronan synthase is with preference a foreign nucleic acid molecule coding for a viral hyaluronan synthase. Preferably, the foreign nucleic acid molecule coding for a hyaluronan synthase codes for a hyaluronan synthase of a virus which infects algae.

With respect to an algae-infecting virus, the foreign nucleic acid molecule which codes for a hyaluronan synthase preferably codes for a hyaluronan synthase of a, *Chlorella*-infecting virus, particularly preferably a hyaluronan synthase of a *Paramecium bursaria Chlorella* virus 1 and especially preferably a hyaluronan synthase of a *Paramecium bursaria Chlorella* virus of an H1 strain.

Preferably, the foreign nucleic acid molecule coding for a hyaluronan synthase is characterized in that it codes for a hyaluronan synthase whose amino acid sequence is at least 70%, with preference at least 80%, preferably at least 90%, particularly preferably at least 95% and especially preferably at least 98% identical to the amino acid sequence shown under SEQ ID NO 2. In a particularly preferred embodiment, the foreign nucleic acid molecule coding for a hyaluronan synthase is characterized in that it codes for a hyaluronan synthase which has the amino acid sequence shown under SEQ ID No 2.

In a further embodiment, the foreign nucleic acid molecule coding for a hyaluronan synthase is at least 70%, with preference at least 80%, preferably at least 90%, particularly preferably at least 95% and especially preferably at least 98% identical to the nucleic acid sequence shown under SEQ ID NO 1 or SEQ ID NO 3. In a particularly preferred embodiment, the foreign nucleic acid molecule coding for a hyaluronan synthase is characterized in that it has the nucleic acid sequence shown under SEQ ID No 3 or that the sequence of the foreign nucleic acid molecule differs from the nucleic acid sequence shown under SEQ ID No 1 or 3 owing to the degeneration of the genetic code.

On Aug. 25, 2004, the plasmid IC 341-222, comprising a synthetic nucleic acid molecule coding for a *Paramecium bursaria Chlorella* virus hyaluronan synthase was deposited at the Deutsche Sammlung von Mikroorganismen and Zellkulturen GmbH, Mascheroder Weg 1b, 38124 Brunswick, Germany, under the number DSM16664, in accordance with the Budapest treaty. The amino acid sequence shown under SEQ ID NO 2 can be derived from the coding region of the nucleic acid sequence integrated into the plasmid IC 341-222 and codes for a *Paramecium bursaria Chlorella* virus hyaluronan synthase.

Accordingly, the present invention also relates to genetically modified plant cells according to the invention or genetically modified plants according to the invention where the nucleic acid molecule which codes for the hyaluronan synthase is characterized in that it codes for a protein whose amino acid sequence can be derived from the coding region of the nucleic acid sequence inserted into plasmid DSM16664 or that it codes for a protein whose amino acid sequence is at least 70%, with preference at least 80%, preferably at least 90%, particularly preferably at least 95% and especially preferably at least 98% identical to the amino acid sequence which can be derived from the coding region of the nucleic acid sequence inserted into plasmid DSM 16664.

The present invention also relates to genetically modified plant cells according to the invention or genetically modified plants according to the invention where the foreign nucleic acid molecule coding for hyaluronan synthase is characterized in that it is the hyaluronan-synthase-encoding nucleic acid sequence integrated into plasmid DSM16664 or that it is at least 70%, with preference at least 80%, preferably at least 90%, particularly preferably at least 95% and especially preferably at least 98% identical to the nucleic acid sequence integrated into plasmid DSM16664.

In the context of the present invention, the term "chondroitin synthase" (EC 2.4.1.175, EC 1.4.1.226) is to be understood as meaning a protein or a protein complex, consisting of two proteins which synthesizes chondroitin from the substrates UDP-glucuronic acid (UDP-GlcA) and UDP-N-acetyl-glalactosamine (UDP-GalNAc). The synthesis of chondroitin is catalyzed according to the reaction scheme below:

$n$UDP-GlcA+$n$UDP-GalNAc→beta-1,4-[GlcA-beta-1,3-GalNAc]$_n$+2$n$UDP

In some organisms, the elongation of the chondroitin molecule attached to a proteoglycan is catalyzed by a chondroitin synthase enzyme complex which consists of two different proteins. One of the two proteins, N-acetylgalactosaminyl-transferase II (EC 2.4.1.175), adds N-acetyl-galactosamine monomers via a beta-1,4-attachment, the second protein, N-acetylgalactosaminyl-proteoglycan 3-beta-glucuronosyl-transferase (EC 2.4.1.226), adds glucuronate monomers via a beta-1,3-attachment to the chondroitin molecule. However, the person skilled in the art is also familiar with bifunctional proteins where a single protein adds both N-acetyl-galactosamine monomers and glucuronate monomers to the chondroitin molecule.

In a further preferred embodiment, the present invention relates to genetically modified plant cells according to the invention or genetically modified plants according to the invention where the foreign nucleic acid molecule coding for glucosaminoglycan synthase is characterized in that it codes for a chondroitin synthase.

A preferred embodiment of the present invention relates to plant cells according to the invention or plants according to the invention where the foreign nucleic acid molecule coding for a chondroitin synthase codes for a bifunctional chondroitin synthase which attaches both N-acetyl-galactosamine monomers and glucuronate monomers to the chondroitin molecule.

In the context of the present invention, the term "bifunctional chondroitin synthase" is to be understood as meaning a protein where the activity of an N-acetylgalactosaminyltransferase II (EC 2.4.1.175) and the activity of an acetylgalactosaminyl-proteoglycan 3-beta-glucuronosyltransferase (EC 2.4.1.226) are present in one molecule.

Nucleic acid molecules and amino acid sequences derived therefrom coding for monofunctional chondroitin synthases have been described, for example, from bacteria (for example *Escherichia coli*, US2003109693, EP 1283259).

Nucleic acid molecules and amino acid sequences derived therefrom, coding for bifunctional chondroitin synthases have been described, for example, from mammals (for example *Homo sapiens*, WO 03 012099, US 2005048604, US 2006052335, NCBI acc. No: BC046247.1, BC023531.2; Kitagawa et al., 2001, J. Biol. Chem. 276(42), 38721-38726) or *Pasteurella multicoda* (US 2003104601, EMBL acc. No: AF195517, DeAngelis and Padgett-McCue, 2000, J. Biol. Chem. 275(31), 24124-24129).

The foreign nucleic acid molecule coding for a chondroitin synthase is with preference a foreign nucleic acid molecule coding for a bacterial chondroitin synthase, preferably coding for a chondroitin synthase from *Pasteurella*, particularly preferably coding for a chondroitin synthase from *Pasteurella multocida*.

Preferably, the foreign nucleic acid molecule coding for a chondroitin synthase is characterized in that it codes for a chondroitin synthase whose amino acid sequence is at least 70%, with preference at least 80%, preferably at least 90%, particularly preferably at least 95% and especially preferably at least 98% identical to the amino acid sequence shown under SEQ ID NO 5. In a particularly preferred embodiment, the foreign nucleic acid molecule coding for a chondroitin synthase is characterized in that it codes for a chondroitin synthase which has the amino acid sequence shown under SEQ ID No 5.

In a further embodiment, the foreign nucleic acid molecule coding for a chondroitin synthase is at least 70%, with preference at least 80%, preferably at least 90%, particularly preferably at least 95% and especially preferably at least 98% identical to the nucleic acid sequence shown under SEQ ID NO 4. In a particularly preferred embodiment, the nucleic acid molecule coding for the chondroitin synthase is characterized in that it has the nucleic acid sequence shown under SEQ ID No 4 or that the sequence of the foreign nucleic acid molecule differs from the nucleic acid sequence shown under SEQ ID No 4 owing to the degeneration of the genetic code.

In the context of the present invention, the term "heparin/heparosan synthase" or "heparosan synthase" (EC 2.4.1.224, EC 2.4.1.225) is to be understood as meaning a protein or an enzyme complex consisting of two proteins which synthesizes heparin/heparan from the substrates UDP-glucuronic acid (UDP-GlcA) and UDP-N-acetyl-glucosamine (UDP-GlcNAc). The synthesis of heparin/heparan is catalyzed according to the reaction scheme below:

Nucleic acid molecules and amino acid sequences derived therefrom, coding for a heparin/heparosan synthase have been described, for example, from bacteria (*Pasteurella multocida* EMBL acc. Nos: AF425591, AF439804, AY292199, AY292200, US 20030099967, *Escherichia coli* EMBL acc. No: X77617.1) or humans (NCBI acc. Nos: BC001174.1, NM_207122.1).

In some organisms, the elongation of the heparin/heparosan molecule attached to a proteoglycan is catalyzed by a heparin/heparosan synthase enzyme complex which consists of two different proteins. One of the two proteins, glucuronosyl-N-aceytlglucosaminyl-proteoglycan 4-alpha-N-glucosaminyltransferase (EC 2.4.1.224), adds N-acetyl-glucosamine monomers via a beta-1,4-attachment, the second protein, N-acetylglucosaminyl-proteoglycan 4-beta-glucoronosyltransferase (EC 2.4.1.225), adds glucuronate monomers via a beta-1,3-attachment to the heparin/heparan molecule. However, the person skilled in the art is also familiar with bifunctional proteins where a single protein adds both N-acetyl-glucosamine monomers and glucuronate monomers to the heparin/heparosan molecule. Such bifunctional heparin/heparosan synthasen have been described, for example, from humans (Busse and Kusche-Gullberg, 2003, J. Biol. Chem. 278(42), 41333-41337) or from *Pasteurella* (DeAngelis and White, 2004, J. Bacteriology 186(24), 8529-8532). Bifunctional proteins having the activity of a heparin/heparosan synthase have both the activity of an enzyme classified under EC number 2.4.1.224 and the activity of an enzyme classified under EC number 2.4.1.225.

In a further preferred embodiment, the present invention relates to genetically modified plant cells according to the invention or genetically modified plants according to the invention where the foreign nucleic acid molecule coding for a glucosaminoglycan synthase is characterized in that it codes for a heparin/heparosan synthase.

A preferred embodiment of the present invention relates to plant cells according to the invention or plants according to the invention where the foreign nucleic acid molecule coding for a heparin/heparosan synthase codes for a bifunctional heparin/heparan synthase which attaches both N-acetyl-glucosamine monomers and glucuronate monomers to the heparin/heparan molecule.

The foreign nucleic acid molecule coding for a heparin/heparosan synthase is with preference a foreign nucleic acid molecule coding for a bacterial heparin/heparosan synthase, preferably coding for a heparin/heparosan synthase from *Pasteurella*, particularly preferably coding for a heparin/heparosan synthase from *Pasteurella multocida*.

Preferably, the foreign nucleic acid molecule coding for heparin/heparosan synthase is characterized in that it codes for a heparin/heparosan synthase whose amino acid sequence is at least 70%, with preference at least 80%, preferably at least 90%, particularly preferably at least 95% and especially preferably at least 98% identical to the amino acid sequence shown under SEQ ID NO 7. In a particularly preferred embodiment, the foreign nucleic acid molecule coding for the heparin/heparosan synthase is characterized in that it codes for a heparin/heparosan synthase which has the amino acid sequence shown under SEQ ID No 7.

In a further embodiment, the foreign nucleic acid molecule coding for a heparin/heparosan synthase is at least 70%, with preference at least 80%, preferably at least 90%, particularly preferably at least 95% and especially preferably at least 98% identical to the nucleic acid sequence shown under SEQ ID NO 6. In a particularly preferred embodiment, the nucleic acid molecule coding for a heparin/heparosan synthase is characterized in that it has the nucleic acid sequence shown under SEQ ID No 6 or that the sequence of the foreign nucleic acid molecule differs from the nucleic acid sequence shown under SEQ ID No 6 owing to the degeneration of the genetic code.

In the context of the present invention, the term "glucosamine phosphate N-acetyltransferase (acetyl-CoA:D-glucosamine phosphate N-acetyltransferase or GlcN-P acetyltransferase)" (EC 2.3.1.4) is to be understood as meaning a protein which synthesizes N-acetyl-D-glucosamine phosphate (GlcNAc-P) from the substrates D-glucosamine phosphate (GlcN-P) and acetyl-CoA (AcCoA). The synthesis of N-acetyl-glucosamine 6-phosphate is catalyzed according to the reaction scheme below:

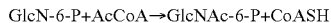

In the reaction equation shown, the substrate GlcN-P may be either glucosamine 1-phosphate (GlcN-1-P) or glucosamine 6-phosphate (GlcN-6-P).

In the metabolic pathways in question for the synthesis of UDP-N-acetyl-glucosamine, an essential difference between the bacterial and eukaryotic organisms studied is that different intermediates of the metabolic pathway in question are used as substrate for the acetylation reaction. In bacterial organisms, the acetylation of GlcN-1-P is carried out by a protein having the activity of a GlcN-1-P acetyltransferase (EC 2.3.1.157) (Gehring et al., 1996, Biochemistry 35, 579-585), whereas in eukaryotic animals or fungi the acetylation of GlcN-6-P is catalyzed by a protein having the activity of a glucosamine 6-phosphate acetyltransferase (EC 2.3.1.4) (Milewski et al., 2006, Yeast 23, 1-14, published online in Wiley InterScience, DOI: 10.1002./yea.1337). Accordingly, in the different organisms, both different substrates and different proteins are used for the synthesis of UDP-GlcNAc.

Surprisingly, it has been found that, in contrast to the disclosure in the prior art (WO 2007 023682), it is not possible to increase the amount of glucosaminoglycans synthesized in plant cells by introducing any nucleic acid molecule coding for a protein having the activity of a GlcN-P acetyltransferase into plant cells. Rather, it has been found that the introduction of a foreign nucleic acid molecule coding for a protein having the activity of a GlcN-P acetyltransferase which acetylates GlcN-1-P (for example glmu from *Escherichia coli*) does not lead to an increase in the amount of glucosaminoglycans synthesized by plant cells or plants. Accordingly, it is essential for plant cells according to the invention or plants according to the invention that the foreign nucleic acid molecule codes for a protein having the activity of a GlcN-P acetyltransferase which uses GlcN-6-P as substrate for the acetylation reaction and is thus a protein having the activity of a GlcN-6-P acetyltransferase (EC 2.3.1.4). In contrast, foreign nucleic add molecules coding for proteins having the activity of a GlcN-1-P acetyltransferase (EC 2.3.1.157), which use GlcN-1-P for the acetylation reaction are not suitable for producing plant cells according to the invention or plants according to the invention.

Furthermore, it has been found that plant cells or plants having a foreign nucleic acid molecule coding for a glucosamine 6-phosphate mutase (GlcN-6-P mutase), which catalyzes the isomerization of GlcN-6-P to GlcN-1-P, do not synthesize significantly higher amounts of glucosaminoglycan.

In the context of the present invention, the term "glucosamine 6-phosphate acetyltransferase (acetyl-CoA:D-glucosamine 6-phosphate N-acetyltransferase or GlcN-6-P acetyltransferase)" (EC 2.3.1.4) is meant to be understood as a protein which synthesizes N-acetyl-D-glucosamine 6-phosphate (GlcNAc-6-P) from the substrates D-glucosamine 6-phosphate (GlcN-6-P) and acetyl-CoA (AcCoA). The synthesis of N-acetyl-glucosamine 6-phosphate is catalyzed according to the reaction scheme below:

GlcN-6-P+AcCoA→GlcNAc-6-P+CoASH

The functional form of a protein having the activity of a GlcN-6-P acetyltransferase is a homodimer. The tertiary structure of the monomer has a central core region. This core region consists of a beta-sheet structure having five antiparallel strands (beta strands 1-5) which are surrounded by four alpha-helices and a sixth beta strand (beta-6 strand). During the formation of the homodimer, there is an interaction of a beta-6 strand of a subunit with the corresponding beta-6 strand of the respective other subunit.

The amino acid sequence shown under SEQ ID No 9 (EMBL acc. No: AB017626.1) codes for a protein having the activity of a GlcN-6-P acetyltransferase from *Saccharomyces cerevisiae*. In the amino acid sequence shown under SEQ ID No 9, the amino acids 7-11 form the beta-1 strand, the amino acids 13-26 form the alpha-1 strand, the amino acids 37-47 form the alpha-2 strand, the amino acids 62-69 form the beta-2 strand, the amino acids 74-86 form the beta-3 strand, the amino acids 92-103 form the beta-4 strand, the amino acids 111-125 form the alpha-3 strand, the amino acids 130-136 form the beta-5 strand, the amino acids 139-146 form the alpha-3 strand and the amino acids 154-159 form the beta-6 strand. The amino acids Glu (position 98), Asp (position 99) and Ile (position 100) present in the beta-4 strand in the sequence shown under SEQ ID No 9 interact with the substrate AcCoA, they polarize its carbonyl bond and they stabilize the negative charge of the oxygen atom of the AcCoA in the tetraedric reaction intermediate consisting of AcCoA and GlcN-6-P and GlcN-6-P acetyltransferase. The amino acid Tyr (position 143) in the sequence shown under SEQ ID No 9 stabilizes the thiolate anion of the CoA molecule to be cleaved off. These interactions during the catalysis of the reaction are supported by the amino acid Leu (position 133) in the sequence shown under SEQ ID No 9. During the catalysis of the reaction, GlcN-6-P is bound in a pocket formed between the monomers of the homodimer, with amino acid residues of the beta-6 strand participating in its formation. During the catalysis of the reaction, the amino acid Asp (position 134) in the sequence shown under SEQ ID No 9 increases the nucleophilicity of the amino group of GlcN-6-P (Milewski et al., 2006, published online in Wiley InterScience, www.interscience.wiley.com, DOI:10.1002/yea.1337). Further amino acids of a protein having the activity of a GlcN-6-P acetyltransferase which are involved in the catalysis of the reaction in question are described in Peneff et al. (2004, J. Biological Chemistry 276(19), 16328-16334, FIG. 1).

The amino acids which are involved here in an exemplary manner for the amino acid sequence of *Saccharomyces cerevisiae* in the catalysis of the reaction can also be identified in amino acid sequences coding for proteins having the activity of a GlcN-6-P acetyltransferase from other organisms. These are, for example, the amino acids Glu88, Asp80, Ile90, Asp124 and Tyr133 in the amino acid sequence coding for a protein having the activity of a GlcN-6-P acetyltransferase from *Candida albicans* (EMBL acc. No: AB017627.1).

Nucleic acid molecules and corresponding protein sequences coding for proteins having the activity of a GlcN-6-P acetyltransferase have been described, inter alia, for the following organisms: *Saccharomyces cerevisiae* (EMBL acc. No: AB017626.1), *Schizosaccharomyces pombe* (EMBL acc. No: AB017629.1), *Candida albicans* (EMBL acc. No: AB017627.1), *Aspergillus oryzae* (EMBL CDS acc. No: BAE62756.1), *Caenorhabditis elegans* (NCBI acc. No:

NM_073253.4, EMBL CDS acc. No: BAA63497.1, CAA044531.1), *Drosophila melanogaster* (EMBL CDS acc. No: AAL13916.1), *Xenopus traopicalis* (EMBL acc. No: CR760021.2), *Mus musculus* (EMBL CDS acc. No: BAE39886.1), *Homo sapiens* (EMBL CDS acc. No: BAC03482.1), *Pongo pygmaeus* (EMBL CDS acc. No: CR858996.1), *Acanthamoeba polyphaga* mimivirus (EMBL CDS acc. No: AAV50586.1). Although, as already described, the amino acid residues involved in the catalysis of the reaction are conserved in proteins originating from various organisms having the activity of a GlcN-6-P acetyltransferase, in some cases their sequences have very low identity to one another. Thus, the amino acid sequence coding for a protein having the activity of a GlcN-6-P acetyltransferase from *Saccharomyces cerevisiae* (EMBL acc. No: AB017626.1) is only 44% identical to the corresponding sequence from *Candida albicans* (EMBL acc. No: AB017627.1) and even has only 25% identity to that from *Schizosaccharomyces pombe* (EMBL acc. No: AB017629.1) (Milewski et al., 2006, published online in Wiley InterScience, www.interscience.wiley.com, DOI:10.1002/yea.1337). In spite of the low identity of the amino acid sequences in question to one another, all abovementioned sequences coding for a protein having the activity of a GlcN-6-P-acetyltransferase are suitable for producing plant cells according to the invention or plants according to the invention.

According to the invention, the foreign nucleic acid molecule coding for a protein having the enyzmatic activity of a GlcN-6-P acetyltransferase may originate from any organism; preferably, said nucleic acid molecule originates from fungi, animals or plants, particularly preferably from fungi and especially preferably from *Saccharomyces cerevisiae*.

Preferably, the foreign nucleic acid molecule coding for GlcN-6-P acetyltransferase is characterized in that it codes for a GlcN-6-P acetyltransferase whose amino acid sequence is at least 70%, with preference at least 80%, preferably at least 90%, particularly preferably at least 95% and especially preferably at least 98% identical to the amino acid sequence shown under SEQ ID NO 9. In a particularly preferred embodiment, the foreign nucleic acid molecule coding for a protein having the activity of a GlcN-6-P acetyltransferase is characterized in that it codes for a protein having the activity of a GlcN-6-P acetyltransferase which has the amino acid sequence shown under SEQ ID No 9.

In a further embodiment, the foreign nucleic acid molecule coding for a protein having the activity of a GlcN-6-P acetyltransferase is at least 70%, with preference at least 80%, preferably at least 90%, particularly preferably at least 95% and especially preferably at least 98% identical to the nucleic acid sequence shown under SEQ ID NO 8. In a particularly preferred embodiment, the nucleic acid molecule coding for a GlcN-6-P acetyltransferase is characterized in that it has the nucleic acid sequence shown under SEQ ID No 8 or that the sequence of the foreign nucleic acid molecule differs from the nucleic acid sequence shown under SEQ ID No 8 owing to the degeneration of the genetic code.

In the context of the present invention, the term "UDP-GlcNAc pyrophosphorylase (2-acetamido-2-deoxy-d-glucose 1-phosphate uridyltransferase) (EC 2.7.7.23)" is to be understood as meaning a protein which synthesizes UDP-N-acetyl-glucosamine (UDP-GlcNAc) from the substrates uridine triphosphate (UTP) and N-acetyl-D-glucosamine 1-phosphat (GlcNAc-1-P). The synthesis of UDP-GlcNAc is catalyzed according to the reaction scheme below:

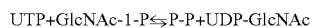

Procaryotic proteins having the activity of a UDP-GlcNAc pyrophosphorylase are generally bifunctional proteins which, in addition to the reaction shown above (EC 2.7.7.23), have the function of a glucosamine 1-phosphate acetyltransferase (GlcN-1-P acetyltransferase, EC 2.3.1.157), i.e. they catalyze an N-acetylation of glucosamine 1-phosphate (GlcN-1-P) to N-acetyl-glucosamine 1-phosphate (GlcNAc-1-P) (GlcN-1-P+AcCoA→GlcNAc-1-P+CoASH) (Gehring et al., 1996, Biochemistry 35, 579-585). In contrast, eukaryotic proteins having the activity of a UDP-GlcNAc pyrophosphorylase are monofunctional proteins which only catalyze the reaction described above (UTP+GlcNAc-1-P⇌P-P+UDP-GlcNAc) (Mio et al., 1998, J. Biol. Chem. 273 (23), 14392-14397).

In the context of the present invention, the term "monofunctional proteins having the activity of a UDP-GlcNAc pyrophosphorylase" is to be understood as meaning a protein which catalyzes the reaction shown above for a protein having the activity of a UDP-GlcNAc pyrophosphorylase (UTP+GlcNAc-1-P⇌P-P+UDP-GlcNAc). A monofunctional protein having the activity of a UDP-GlcNAc pyrophosphorylase has no (additional) activity which catalyzes an acetylation of GlcN-1-P to GlcNAc-1-P. Accordingly, monofunctional proteins having the activity of a GlcNAc pyrophosphorylase are therefore proteins classified under the EC number 2.7.7.23, whereas bifunctional proteins having the activity of a UDP-GlcNAc pyrophosphorylase have both the activity of an enzyme classified under the EC number 2.7.7.23 and the activity of an enzyme classified under the EC number 2.3.1.157.

Surprisingly, it has been found that, in contrast to the disclosure in the prior art (for example WO 2007 023682), that plant cells according to the invention or plants according to the invention having a foreign nucleic acid molecule coding for a bifunctional protein having the activity of a UDP-GlcNAc pyrophosphorylase and the activity of a GlcN-1-P acetyltransferase (for example glmU aus *E. coli*, EC 2.7.7.23 and EC 2.3.1.157) do not synthesize increased amounts of glucosaminoglycans. Accordingly, it is essential for plant cells according to the invention or plants according to the invention that the foreign nucleic acid molecule coding for a UDP-GlcNAc pyrophosphorylase codes for a monofunctional protein having the activity of a UDP-GlcNAc pyrophosphorylase (EC 2.7.7.23). Accordingly, the foreign nucleic acid molecule coding for a UDP-GlcNAc pyrophosphorylase should not code for a protein which, in addition to the just mentioned activity of a UDP-GlcNAc pyrophosphorylase has the additional activity of a GlcN-1-P acetyltransferase (EC 2.3.1.157). Thus, it is preferably a foreign nucleic acid molecule of eukaryotic origin. Furthermore, it has surprisingly been found that, in contrast to the disclosure in the prior art (for example WO 2007 023682), the expression of a phosphoacetylglucosamine mutase (GlcNAc-P mutase, EC 5.4.2.3) in addition to the expression of a protein having the activity of a GlcN-6-P acetyltransferase and the expression of a protein having the activity of a UDP-GlcNAc pyrophosphorylase does not lead to a further increase in the amount of glucosaminoglycans in plant cells or plants.

Amino acid sequences coding for monofunctional proteins having the activity of a UDP-GlcNAc pyrophosphorylase comprise amino acid residues which are highly conserved between the proteins. Amino acid sequences coding for eukaryotic proteins having the activity of a UDP-GlcNAc pyrophosphorylase have in each case three domains which are conserved between the proteins. The consensus sequence of the first domain is GlyGlyGlnXxxThrArgLeuGlyXxxXxxXxxProLysGly (SEQ ID NO: 31) (amino acids 111-124 in the sequence shown under SEQ ID No 11), that of the second domain is Pro(Asp or Asn)GlyAsn(Gly or Ala)GlyXxxXxxXxxAla (SEQ ID NO: 32) (amino acids 219-228 in the sequence shown under SEQ ID No 11) and that of the third domain is LysXxxGluXxxPheXxxPheAspXxxPhe (SEQ ID NO: 33) (amino acids 377-386 in the sequence shown under SEQ ID No 11), where Xxx is any amino acid. Prokaryotic proteins having the activity of a UDP-GlcNAc pyrophosphorylase (for example glmU aus *Escherichia coli*, EMBL ace. No: EAY46949.1) have a conserved domain (GlyXxxGlyThr(Arg or Ser)XxxXxxXxxXxxProLys) (SEQ ID NO: 34) which is similar to the first domain of corresponding proteins from eukaryotes. For the domains two and three of the eukaryotic proteins, no corresponding domains are found in the prokaryotic proteins. (Mok and Edwards, 2000, J. Biol. Chem. 280(47), 39363-39372), The amino acids Gly (position 112), Gly (position 114), Thr (position 115), Arg (position 116), Pro (position 122) and Lys (position 123) in the amino acid sequence shown under SEQ ID No 11 are conserved in the primary sequences coding for proteins having the activity of a UDP-GlcNAc pyrophosphorylase. An exchange of the amino acids Gly (position 112), Arg (position 116), or Lys (position 123) in the amino acid sequence shown under SEQ ID No 11 leads to virtually inactive proteins. In contrast, an exchange of the amino acids Gly (position 114), Thr (position 115) or Pro (position 122) in the amino acid sequence shown under SEQ ID No 11 shows only a reduction of the activity of the protein in question. Accordingly, the amino acids Gly (position 112), Arg (position 116) and Lys (position 123) in the amino acid sequence shown under SEQ ID No 11 are amino acids which have a catalytic function in proteins having the activity of a UDP-GlcNAc pyrophosphorylase (Mio et al., 1998, J. Biol. Chem. 273(23), 14392-14397).

In the amino acid sequence coding for a protein having the activity of a UDP-GlcNAc pyrophosphorylase from *Giardia intestinales* (EMBL acc. No: AAM54702.1), the amino acid Gly (position 108) corresponds to the amino acid Gly (position 112) of the sequence shown under SEQ ID No 11. The exchange of the amino acid Gly (position 108) in the amino acid sequence coding for a protein having the activity of a UDP-GlcNAc pyrophosphorylase from *Giardia intestinales* via the amino acid Ala also results in an almost complete reduction of the activity of the protein (Mok and Edwards, 2005, J. Biol. Chem. 280(47), 39363-39372). The exchange of the amino acid Gly (position 111) in the amino acid sequence coding for a protein having the activity of a UDP-GlcNAc pyrophosphorylase from *Homo sapiens* (EMBL acc. No: BAA31202.1), which corresponds to the amino acid Gly (position 112) in the sequence shown under SEQ ID No 11, also leads to almost complete reduction of the activity (Wang-Gillam et al., 2000, J. Biol. Chem. 275(2), 1433-1438).

An exchange of the amino acid Gly (position 222) in the protein coding for a UDP-GlcNAc pyrophosphorylase from *Homo sapiens* (EMBL acc. No: BAA31202) and the corresponding amino acid Gly (position 210) of a corresponding protein from *Giardia intestinales* (EMBL acc. No: AAM54702.1) results in both cases likewise in an almost complete loss of activity, which indicates that the amino acids mentioned are likewise amino acids involved in the catalysis (Mok and Edwards, 2005, J. Biol. Chem. 280(47), 39363-39372). An exchange of the amino acid Gly (position 224) in the protein coding for a UDP-GlcNAc pyrophosphorylase from *Homo sapiens* (EMBL acc. No: BAA31202) lead to a considerable, but not complete, loss of the activity of the protein, and an exchange of the amino acid Pro (position 222) resulted in only a slight reduction of activity. From this, it was concluded that the amino acids Gly (position 221) and Gly (position 223) of the sequence shown under SEQ ID No 11 take part in the recognition of the UTP and amino acids Gly (position 111) and Gly (position 112), conserved in the respective primary sequences, of the sequence shown under SEQ ID No 11 are involved in binding GlcNAc-1-P (Wang-Gillam et al., 2000, J. Biol. Chem. 275(2), 1433-1438).

Nucleic acid molecules and corresponding protein sequences coding for proteins having the monofunctional activity of a UDP-GlcNAc pyrophosphorylase having the properties mentioned above have been described inter alia for the following organisms: *Giardia intestinales* (EMBL acc. No: AAM54702.1), *Saccharomyces cerevisiae* (EMBL acc. No: X79380.1, NCBI protein ID: accession No: CAA557927), *Candida albicans* (NCBI acc. No: XM_715480.1), *Pichia stipitis* (NCBI acc. No: XM_001385151.1), *Mus musculus* (NCBI acc. No: NM_133806.4), *Canis lupus* (NCBI acc. No: XM_844774.1); *Bos taurus* (NCBI acc. No: NM_001046404.1), *Xenopus tropicalis* (NM_001011142.1), *Xenopus laevis* (NCBI acc. No: BC077836.1), *Arabidopsis thaliana* (NCBI acc. No: NM_102845.4), *Danio rerio* (NCBI acc. No: NM_212621.1), *Homo sapiens* (NCBI acc. No: NM_003115.3, EMBL acc. No.: BAA31202.1).

According to the invention, the foreign nucleic acid molecule coding for a protein having the enyzmatic activity of a UDP-GlcNAc pyrophosphorylase may originate from any eukaryotic organism; preferably, said nucleic acid molecule originates from fungi, animals or plants, particularly preferably from fungi, especially preferably from *Saccharomyces cerevisiae*.

Preferably, the foreign nucleic acid molecule coding for a protein having the activity of a UDP-GlcNAc pyrophosphorylase is characterized in that it codes for a UDP-GlcNAc pyrophosphorylase whose amino acid sequence at least 70%, with preference at least 80%, preferably at least 90%, particularly preferably at least 95% and especially preferably at least 98% identical to the amino acid sequence shown under SEQ ID NO 11. In a particularly preferred embodiment, the foreign nucleic acid molecule coding for a protein having the activity of a UDP-GlcNAc pyrophosphorylase is characterized in that it codes for a protein having the activity of a UDP-GlcNAc pyrophosphorylase having the amino acid sequence shown under SEQ ID No 11.

In a further embodiment, the foreign nucleic acid molecule coding for a protein having the activity of a UDP-GlcNAc pyrophosphorylase is at least 70%, with preference at least 80%, preferably at least 90%, particularly preferably at least 95% and especially preferably at least 98% identical to the nucleic acid sequence shown under SEQ ID NO 10. In a particularly preferred embodiment, the nucleic acid molecule coding for a UDP-GlcNAc pyrophosphorylase is characterized in that it has the nucleic acid sequence shown under SEQ ID No 10 or that the sequence of the foreign nucleic acid molecule differs from the nucleic acid sequence shown under SEQ ID No 10 owing to the degeneration of the genetic code.

In the context of the present invention, the term "foreign nucleic acid molecule" is to be understood as meaning a molecule which either does not naturally occur in the corresponding wild-type plant cells or which does not naturally occur in the concrete spatial arrangement in wild-type plant cells or which is localized at a site in the genome of the wild-type plant cell where it does not naturally occur.

Preferably, the foreign nucleic acid molecule is a recombinant molecule comprising various elements whose combination or specific spatial arrangement does not naturally occur in plant cells.

In the context of the present invention, the term "recombinant nucleic acid molecule" is to be understood as meaning a nucleic acid molecule which comprises various nucleic acid molecules which are not naturally present in a combination like that present in a recombinant nucleic acid molecule. Thus, recombinant nucleic acid molecules may, in addition to nucleic acid molecules coding for a glucosaminoglycan synthase and/or a protein having the activity of a GlcN-6-P acetyltransferase and/or a protein having the activity of a UDP-GlcNAc pyrophosphorylase, additionally comprise nucleic acid sequences which are not naturally present in combination with the nucleic acid molecules mentioned. The additional nucleic acid sequences mentioned which are present on a recombinant nucleic acid molecule in combination with a nucleic acid molecule coding for a glucosaminoglycan synthase and/or a protein having the activity of a GlcN-6-P acetyltransferase and/or a protein having the activity of a UDP-GlcNAc pyrophosphorylase may be any sequences. For example, they may be genomic plant nucleic acid sequences. The additional nucleic acid sequences are preferably regulatory sequences (promoters, termination signals, enhancers), particularly preferably regulatory sequences which are active in plant tissue, especially preferably tissue-specific regulatory sequences which are active in plant tissue. Methods for generating recombinant nucleic acid molecules are known to the person skilled in the art and comprise genetic engineering methods, such as, for example, linking of nucleic acid molecules by ligation, genetic recombination or the de novo synthesis of nucleic acid molecules (see, for example, Sambrok et al., Molecular Cloning, A Laboratory Manual, 3rd edition (2001) Cold Spring Harbor Laboratory Press, Cold Spring Harbor, N.Y. ISBN: 0879695773, Ausubel et al., Short Protocols in Molecular Biology, John Wiley & Sons; 5th edition (2002), ISBN: 0471250929).

A preferred embodiment of the present invention relates to plant cells according to the invention or plants according to the invention in which the foreign nucleic acid molecules are stably integrated into the genome of the plant cell or plant.

Genetically modified plant cells and genetically modified plants having a foreign nucleic acid molecule (stably) integrated into their genome or a plurality of foreign nucleic acid molecules integrated into their genome which code for a glucosaminoglycan synthase and/or a protein having the activity of a GlcN-6-P acetyltransferase and/or a protein having the activity of a UDP-GlcNAc pyrophosphorylase can be distinguished from wild-type plant cells and wild-type plants inter alia by the fact that they comprise a foreign nucleic acid molecule which does not naturally occur in wild-type plant cells and wild-type plants, respectively, or in that such a molecule is integrated at a site in the genome of the genetically modified plant cell according to the invention or in the genome of the genetically modified plant according to the invention where it does not occur in wild-type plant cells and wild-type plants, respectively, i.e. in a different genomic environment. Furthermore, such genetically modified plant cells according to the invention and genetically modified plants according to the invention can be distinguished from not genetically modified wild-type plant cells and not genetically modified wild-type plants, respectively, in that they comprise at least one copy of the foreign nucleic acid molecule integrated into their genome, if appropriate in addition to copies of such a molecule naturally present in the wild-type plant cells or wild-type plants. If the foreign nucleic acid molecule(s) introduced into the genetically modified plant cells according to the invention or the genetically modified plant according to the invention are additional copies of molecules already naturally present in the wild-type plant cells or the wild-type plants, the genetically modified plant cells according to the invention and the genetically modified plants according to the invention can be distinguished from wild-type plant cells and wild-type plants, respectively, in particular by the fact that this additional copy/these additional copies is/are localized at sites in the genome where it/they is/are not present in wild-type plant cells and wild-type plants, respectively.

The integration of a nucleic acid molecule into the genome of a plant cell or a plant can be demonstrated by genetic methods and/or methods of molecular biology. A stable integration of a nucleic acid molecule into the genome of a plant cell or the genome of a plant is characterized in that in the progeny which has inherited said nucleic acid molecule, the stably integrated nucleic acid molecule is present in the same genomic environment as in the parent generation. The presence of a stable integration of a nucleic acid sequence in the genome of a plant cell or in the genome of a plant can be demonstrated using methods known to the person skilled in the art, inter alia with the aid of Southern blot analysis of the RFLP analysis (Restriction Fragment Length Polymorphism) (Nam et al., 1989, The Plant Cell 1, 699-705; Leister and Dean, 1993, The Plant Journal 4 (4), 745-750), with methods based on PCR, such as, for example, the analysis of differences in length in the amplified fragment (Amplified Fragment Length Polymorphism, AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160) or using amplified fragments cleaved using restriction endonucleases (Cleaved Amplified Polymorphic Sequences, CAPS) (Konieczny and Ausubel, 1993, The Plant Journal 4, 403-410; Jarvis et al., 1994, Plant Molecular Biology 24, 685-687; Bachem et al., 1996, The Plant Journal 9 (5), 745-753).

In the context of the present invention, the term "wild-type plant cell" is to be understood as meaning plant cells which served as starting material for the production of the genetically modified plant cells according to the invention, i.e. their genetic information, apart from the genetic modifications introduced and resulting in an integration of a nucleic acid molecule coding for a glucosaminoglycan synthase and/or a protein having the activity of a GlcN-6-P acetyltransferase and/or a protein having the activity of a UDP-GlcNAc pyrophosphorylase corresponds to that of a genetically modified plant cell according to the invention.

In the context of the present invention, the term "wild-type plant" is to be understood as meaning plants which served as starting material for the production of the genetically modified plants according to the invention, i.e. their genetic information, apart from the genetic modifications introduced and resulting in an integration of a nucleic acid molecule encoding for a glucosaminoglycan synthase and/or a protein having the activity of a GlcN-6-P acetyltransferase and/or a protein having the activity of a UDP-GlcNAc pyrophosphorylase corresponds to that of a genetically modified plant according to the invention.

In the context of the present invention, the term "genome" is to be understood as meaning the entire genetic material present in a plant cell. It is known to the person skilled in the art that, in addition to the nucleus, other compartments (for example plastids, mitochondria) also contain genetic material.

A large number of techniques for (stably) integrating nucleic acid molecules into a plant host cell is available. These techniques include the transformation of plant cells with t-DNA using *Agrobacterium tumefaciens* or *Agrobacterium rhizogenes* as means of transformation, protoplast fusion, injection, electroporation of DNA, introduction of DNA by the biolistic approach and also further options (review in "Transgenic Plants", Leandro ed., Humana Press 2004, ISBN 1-59259-827-7).

The use of agrobacterium-mediated transformation of plant cells has been subject to in-depth studies and has been described exhaustively in EP 120516; Hoekema, I N: The Binary Plant Vector System Offsetdrukkerij Kanters B. V. Alblasserdam (1985), Chapter V; Fraley et al., Crit. Rev. Plant Sci. 4, 1-46 and in An et al. EMBO J. 4, (1985), 277-287. For the transformation of potatoes see, for example, Rocha-Sosa et al., EMBO J. 8, (1989), 29-33), for the transformation of tomato plants see, for example, U.S. Pat. No. 5,565,347.

The transformation of monocotyledonous plants using vectors based on *Agrobacterium* transformation has been described, too (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al, Transgenic Res. 2, (1993), 252-265). An alternative system for transforming monocotyledonous plants is the transformation using the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), the protoplast transformation, the electroporation of partially permeabilized cells, the introduction of DNA using glass fibers. In particular the transformation of corn has been described several times in the literature (cf., for example, WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726). The transformation of other grasses, such as, for example, switchgrass (*Panicum virgatum*, Somleva et al., 2002 Crop Science 42: 2080-2087; Richards et al., 2001, Plant Cell Reporters 20, 48-54) of sugar cane (Bower and Birch, 1992, Plant Journal 2(3), 409-416; Bower et al., 1996 Molecular Breeding 2, 239-249; Arencibia et al., 1998, Transgenic Research 7, 213-222) or millet (Casas et al., 1993, PNAS 90, 11212-11216; U.S. Pat. No. 6,369,298) has also been described.

The successful transformation of other cereal species has also been described, for example for barley (Wan and Lemaux, s.o.; Ritala et al., s.o.; Krens et al., Nature 296, (1982), 72-74) and for wheat (Nehra et al., Plant J. 5, (1994), 285-297; Becker et al., 1994, Plant Journal 5, 299-307). All of the above methods are suitable in the context of the present invention.

Compared to the prior art, genetically modified plant cells according to the invention or genetically modified plants according to the invention offer the advantage that they produce higher amounts of glucosaminoglycan (for example hyaluronan) than plants having only the activity of a glucosamino-glycan synthase. This allows glucosaminoglycan to be produced at little expense since the isolation of glucosaminoglycan from plants having a higher glucosaminoglycan content is less complicated and more cost efficient. Furthermore, compared to the plants described in the prior art, smaller cultivation areas are required to produce glucosaminoglycan using the genetically modified plants according to the invention. This leads to the possibility to provide glucosaminoglycan in sufficient amounts even for industrial application where it is currently not used owing to its scarcity and the high price. Virus-infected plant organisms of the genus *Chlorella* are unsuitable for producing relatively large amounts of glucosaminoglycan (hyaluronan). In the production of glucosaminoglycan (hyaluronan), virus-infected algae have the disadvantage that the genes required for glucosaminoglycan synthase are not stably integrated into their genome (Van Etten and Meints, 1999, Annu. Rev. Microbiol. 53, 447-494), so that, for producing glucosaminoglycan (hyaluronan), the virus infection has to be repeated. Accordingly, it is not possible to isolate individual *Chlorella* cells which synthesize continuously the desired quality and quantity of glucosaminoglycan (hyaluronan). Furthermore, in virus-infected *Chlorella* algae, glucosaminoglycan (hyaluronan) is only produced for a limited period of time, and as a result of the lysis caused by the virus, the algae are killed only about 8 hours after the infection (Van Etten et al., 2002, Arch Virol 147, 1479-1516). In contrast, the present invention offers the advantage that the genetically modified plant cells according to the invention and the genetically modified plants according to the invention can be propagated in an unlimited manner vegetatively or sexually and that they produce glucosaminoglycan (hyaluronan) continuously.

The transgenic plants described in WO 05 012529, which have a nucleic acid molecule coding for a hyaluronan synthase, synthesize a relatively small amount of glucosaminoglycan (hyaluronan). In contrast, the present invention offers the advantage that genetically modified plant cells according to the invention and genetically modified plants according to the invention synthesize considerably higher amounts of glucosaminoglycan.

Accordingly, the present invention also provides genetically modified plant cells according to the invention or genetically modified plants according to the invention which synthesize glucosaminoglycan.

In a preferred embodiment, plant cells according to the invention or plants according to the invention synthetize glucosaminoglycans selected from the group consisting of chondroitin, heparin/heparosan and hyaluronan.

To determine the glucosaminoglycan content with respect to the fresh weight in genetically modified plants according to the invention, use is preferably made of the entire above-ground material of the plants, i.e. all plant parts except for the root.

Genetically modified plant cells according to the invention or genetically modified plants according to the invention which synthesize glucosaminoglycan can be identified by isolating the glucosaminoglycan synthesized by them and confirming its structure. Since plant tissue has the advantage that it does not contain any glucosaminoglycans, a simple and quick isolation method can be used for demonstrating the presence of glucosaminoglycans in genetically modified plant cells according to the invention or genetically modified plants according to the invention. Since plant tissue furthermore has the advantage that it does not contain any glucosaminoglycan-degrading enzymes, a simple and quick isolation method can be used for demonstrating the presence of glucosaminoglycans in genetically modified plant cells according to the invention or genetically modified plants according to the invention. To this end, water is added to the plant tissue to be examined, and the plant tissue is then comminuted mechanically (for example with the aid of a bead mill, a Warring Blender, a juice extractor, etc.). If required, more water may then be added to the suspension, and cell debris and water-insoluble components are then removed by centrifugation. The presence of glucosaminoglycans (for example hyaluronan) in the supernatant obtained after centrifugation can then be demonstrated using, for example, a protein which binds specifically to the relevant glucosaminoglycan (for example hyaluronan).

Such test kits based on immunological reagents (ELISA) for various glucosaminoglycans are known to the person skilled in the art and commercially available (for example test kit for heparin: Lifespan Technologies, 2401 Foothill Drive, Salt Lake City, Utah 84109-1405, Prod. No.: K-2100).

A method for the detection of hyaluronan with the aid of a protein which specifically binds to hyaluronan is described, for example, in U.S. Pat. No. 5,019,498. Test kits for carrying out the method described in U.S. Pat. No. 5,019,498 are commercially available (for example the hyaluronic acid (HA) test kit from Corgenix, Inc., Colorado, USA, Prod. No. 029-001; see also General Methods item 4).

Chondroitin can be detected, for example, with the aid of immunological methods (Mizuguchi et al., 2003, Nature 423, 443-448).

The presence of glucosaminoglycans in the centrifugation supernatant can furthermore also be confirmed using other analysis methods, such as, for example, IR, NMR or mass spectroscopy.

Since it has been observed that, over the time of the development of plants according to the invention, glucosaminoglycans accumulate in plant tissue, the amount of glucosaminoglycan with respect to the fresh weight in genetically modified plants according to the invention is particularly preferably determined at the time of harvest or (one or two) days before harvesting of the plants in question.

In a preferred embodiment, the present invention relates to genetically modified plant cells according to the invention or genetically modified plants according to the invention, characterized in that they produce an increased amount of glucosaminoglycan compared to genetically modified plant cells or compared to genetically modified plants having only a foreign nucleic acid molecule coding for a glucosaminoglycan synthase or compared to genetically modified plant cells or compared to genetically modified plants having a foreign nucleic acid molecule, coding for a glucosaminoglycan synthase and no foreign nucleic acid molecules, coding for proteins having the activity of a UDP-GlcNAc acetyltransferase and no foreign nucleic acid molecules coding for proteins having the activity of a UDP-GlcNAc pyrophosphorylase.

Preferably, the amount of glucosaminoglycan produced with respect to the fresh weight of the plant material in genetically modified plant cells according to the invention or in genetically modified plants according to the invention is increased by a factor of at least 1.2, with preference by a factor of at least 1.4, particularly preferably by a factor of at least 1.6 and especially preferably by a factor of at least 1.8 compared to corresponding genetically modified plant cells or compared to corresponding genetically modified plants having (only) the activity of a glucosaminoglycan synthase. To determine the increase of the glucosaminoglycan content with respect to the fresh weight of the plant material in genetically modified plant cells according to the invention or in genetically modified plants according to the invention, use will preferably be made of a comparison between genetically modified plant cells according to the invention or genetically modified plants according to the invention with corresponding plant cells and plants, respectively, which (only) have glucosaminoglycan synthase activity, where equivalent material (for example leaf, tuber) of plant cells or plants is to be compared where the plant cells or plants from which this material is taken have been cultivated under identical conditions and where the glucosaminoglycan content of plant material having a comparable age (development stage) is to be compared. For example, young leaves of a plant should not be compared to old leaves of a different plant. The same applies to the determination of the glucosaminoglycan content of entire above-ground parts of plants. The plants to be compared should have been cultivated under comparable conditions and have the same development stage.

In a preferred embodiment, the present invention relates to plant cells according to the invention or plants according to the invention synthesizing at least 160 µg, preferably at least 180 µg, particularly preferably at least 200 µg, especially preferably at least 225 µg and most preferably at least 250 µg of glucosaminoglycan per g of fresh weight (FW) of plant material.

In a further embodiment, plant cells according to the invention or plants according to the invention synthesize at most 450 µg, preferably at most 400 µg, particularly preferably at most 300 µg, especially preferably at most 280 µg and most preferably at most 260 µg of glucosaminoglycan per g of fresh weight (FW) of plant material.

In a further embodiment of the present invention, the genetically modified plant cells according to the invention or the genetically modified plants according to the invention are plant cells of a green terrestrial plant or green terrestrial plants, respectively, which synthesize glucosaminoglycans.

In the context of the present invention, the term "green terrestrial plant (Embryophyta)" is to be understood as defined in Strasburger, "Lehrbuch der Botanik" [Textbook of Botany], 34th ed., Spektrum Akad. Verl., 1999, (ISBN 3-8274-0779-6).

A preferred embodiment of the present invention relates to genetically modified plant cells according to the invention of multicellular plants or genetically modified plants according to the invention which are multicellular organisms. Accordingly, this embodiment relates to plant cells or plants which do not originate from single-cell plants (protists) or which are not protists.

The genetically modified plant cells according to the invention or the genetically modified plants according to the invention may, in principle, be plant cells and plants, respectively, of any plant species, i.e. both monocotyledonous and dicotyledonous plants. They are preferably crop plants, i.e. plants cultivated by man for the purpose of feeding man and animal or for producing biomass and/or for preparing substances for technical, industrial purposes (for example corn, rice, wheat, alfalfa, rye, oats, barley, manioc, potato, tomato, switchgrass (*Panicum virgatum*), sago, mung beans, peas, sorghum, carrots, aubergine, radish, oilseed rape, soybeans, peanuts, cucumbers, pumpkins, melons, leek, garlic, cabbage, spinach, sweet potato, asparagus, courgettes, lettuce, artichokes, sweetcorn, parsnip, scorzonera, jerusalem artichoke, banana, sugarbeet, sugarcane, beetroot, broccoli, cabbage, onion, yellow beet, dandelion, strawberry, apple, apricot, plum, peach, grapevines, cauliflower, celery, bell peppers, swede, rhubarb). Particularly preferred are corn, sugar cane, sweet potato or sugar millet, very particularly preferred are tomato or potato plants.

In a preferred embodiment, the present invention relates to genetically modified plant cells according to the invention or genetically modified plants according to the invention where the foreign nucleic acid molecule coding for proteins are characterized in that the codons of the foreign nucleic acid molecule are modified compared to the codons of the nucleic acid molecule coding for the respective protein of the original organism. With particular preference, the codons of the foreign nucleic acid molecules have been modified such that they are adapted to the frequency of the use of the codons of the plant cell or the plant into whose genome they are integrated or to be integrated.

Owing to the degeneration of the genetic code, amino acids can be coded by one or more codons. In different organisms, the codons coding for an amino acid are used at different frequencies. Adapting the codon of a coding nucleic acid sequence to the frequency of their use in the plant cell or in the plant into whose genome the sequence to be expressed is to be integrated may contribute to an increased amount of translated protein and/or to the stability of the mRNA in question in the particular plant cells or plants. The frequency of use of codons in the plant cells or plants in question can be determined by the person skilled in the art by examining as many coding nucleic acid sequences of the organism in question as possible for the frequency with which certain codons are used for coding a certain amino acid. The frequency of the use of codons of certain organisms is known to the person skilled in the art and can be determined in a simple and rapid manner using computer programs. Suitable computer programs are publicly accessible and provided for free inter alia on the internet (for example Dr. Thomas Schödl, Universität Regensburg Naturwissenschaftilche Fakultät III, Biologie and Vorklinisch Medizin, Universtätsstraβe 31, 93040 Regensburg; Kazusa DANN Research Institute, 2-6-7 Kazusa-kamatari, Kisarazu, Chiba 292-0818. Japan; Entelechon GmbH, Industriestraβe 1, 93077 Bad Abbach). Adapting the codons of a coding nucleic acid sequence to the frequency of their use in the plant cell or in the plant into whose genome the sequence to be expressed is to be integrated can be carried out by in vitro mutagenesis or, preferably, by de novo synthesis of the gene sequence. Methods for the de novo synthesis of nucleic acid sequences are known to the person skilled in the art. A de novo synthesis can be carried out, for example, by initially synthesizing individual nucleic acid oligonucleotides, hybridizing these with oligonucleotides complementary thereto, so that they form a DNA double strand, and then ligating the individual double-stranded oligonucleotides such that the desired nucleic acid sequence is obtained. The de novo synthesis of nucleic acid sequences including the adaptation of the frequency with which the codons are used to a certain target organism can also be sourced out to companies offering this service (for example Entelechon GmbH, Regensburg, Germany).

In the context of the present invention, the term "identity" means a sequence identity over the entire length of the coding region of a nucleic acid molecule or the entire length of an amino acid sequence coding for a protein of at least 60%, in particular in identity of at least 70%, preferably of at least 80%, particularly preferably of at least 90% and especially preferably of at least 95%. In the context of the present invention, the term "identity" is to be understood as meaning the number of identical amino acids/nucleotides (identity) with other proteins/nucleic acids, expressed in percent. Preferably, the identity with respect to a protein having the activity of a hyaluronan synthase is determined by comparison with the amino acid sequence given under SEQ ID NO 2 and the identity with respect to a nucleic acid molecule coding for a protein having the activity of a hyaluronan synthase is determined by comparison with the nucleic acid sequence given under SEQ ID NO 1 or SEQ ID NO 3, the identity with respect to a protein having the activity of a chondroitin synthase is determined by comparison with the amino acid sequence shown under SEQ ID NO 5 or the identity with respect to a nucleic acid molecule coding for a protein having the activity of a chondroitin synthase is determined by comparison with the nucleic acid sequence shown under SEQ ID NO 4, the identity with respect to a protein having the activity of a heparin/heparosan synthase is determined by comparison with the amino acid sequence shown under SEQ ID NO 7 or the identity with respect to a nucleic acid molecule coding for a protein having the activity of a heparin/heparosan synthase is determined by comparison with the nucleic acid sequence shown under SEQ ID NO 6, the identity with respect to a protein having the activity iof a GIcNAc-6-P acetyltransferase is determined by comparison with the amino acid sequence shown under SEQ ID NO 9 or the identity with respect to a nucleic acid molecule coding for a protein having the activity of a GIcNAc-6-P acetyltransferase is determined by comparison with the nucleic acid sequence shown under SEQ ID NO 8, the identity with respect to a protein having the activity of a UDP-GIcNAc pyrophosphorylase is determined by comparison with the amino acid sequence given under SEQ ID NO 11 or the identity with respect to a nucleic acid molecule coding for a protein having the activity of a UDP-GIcNAc pyrophosphorylase is determined by comparison with the nucleic acid sequence shown under unter SEQ ID NO 10 with other proteins/nucleic acids with the aid of computer programs. If sequences to be compared with one another are of different lengths, the identity is to be determined by determining the identity in percent of the number of amino acids which the shorter sequence shares with the longer sequence. Preferably, the identity is determined using the known and publicly available computer program ClustalW (Thompson et al., Nucleic Acids Research 22 (1994), 4673-4680). ClustalW is made publicly available by Julie Thompson EMBL Heidelberg, Meyerhofstraβe 1, 69117 Heidelberg, Germany and Toby Gibson EMBL Heidelberg, Meyerhofstraβe 1, 69117 Heidelberg, Germany, European Molecular Biology Laboratory, Meyerhofstrasse 1, D 69117 Heidelberg, Germany. ClustalW can also be downloaded from various internet pages, inter alia from IGBMC (Institut de Génétique et de Biologie Moleculaire et Cellulaire, B.P.163, 67404 Illkirch Cedex, France; and from EBI and all mirrored internet pages of the EBI (European Bioinformatics Institute, Wellcome Trust Genome Campus, Hinxton, Cambridge CB 10 1SD, UK).

Preferably, use is made of the ClustalW computer program of version 1.8 to determine the identity between proteins described in the context of the present invention and other proteins. Here, the parameters have to be set as follows: KTUPLE=1, TOPDIAG=5, WINDOW=5, PAIRGAP=3, GAPOPEN=10, GAPEXTEND=0.05, GAPDIST=8, MAXDIV=40, MATRIX=GONNET; ENDGAPS(OFF), NOPGAP, NOHGAP.

Preferably, use is made of the ClustalW computer program of version 1.8 to determine the identity for example between the nucleotide sequence of the nucleic acid molecules described in the context of the present invention and the nucleotide sequence of other nucleic acid molecules. Here, the parameters have to be set as follows:
KTUPLE=2, TOPDIAGS=4, PAIRGAP=5, DNAMATRIX: IUB, GAPOPEN=10, GAPEXT=5, MAXDIV=40, TRANSITIONS: unweighted.

Identity furthermore means that there is a functional and/or structural equivalence between the nucleic acid molecules in question or the proteins encoded by them. The nucleic acid molecules which are homologous to the molecules described above and represent derivatives of these molecules are generally variations of these molecules which represent modifications having the same biological function. They may be either naturally occurring variations, for example sequences from other species, or mutations, where these mutations may have occurred in a natural manner or were introduced by targeted mutagenesis. Furthermore, the variations may be synthetically produced sequences. The allelic variants may be either naturally occurring variants or synthetically produced variants or variants generated by recombinant DNA techniques. A special form of derivatives are, for example, nucleic acid molecules which differ from the nucleic acid molecules described in the context of the present invention owing to the degeneration of the genetic code.

Proteins encoded by different nucleic acid molecule derivatives have certain common characteristics.

These may, for example, be biological activity, substrate specificity, molecular weight, immunological reactivity, conformation, etc.

The present invention furthermore provides genetically modified plant cells according to the invention or genetically modified plants according to the invention characterized in that the foreign nucleic acid molecules integrated into the genome of the plant cell or the plant coding for a glucosaminoglycan synthase and coding for a protein having the activity of a GlcNAc-6-P acetyltransferase and/or coding for a protein having the activity of a UDP-GlcNAc acetyltransferase are linked to regulatory elements initiating the transcription in plant cells (promoters). These may be homologous or heterologous promoters. The promoters can be constitutive, tissue-specific, development-specific or regulated by external factors (for example after application of chemical substances, by action of abiotic factors, such as heat and/or cold, drought, disease, etc.). Here, nucleic acid molecules coding for a glucosaminoglycan synthase or a protein having the activity of a GlcNAc-6-P acetyltransferase or a protein having the activity of a UDP-GlcNAc pyrophosphorylase which are integrated into the genome of a genetically modified plant cell according to the invention or a genetically modified plant according to the invention may in each case be attached to the same promoter, or different promoters may be attached to the individual sequences. Here, two or three different promoters may be present in any combination, in each case attached to a relevant foreign nucleic acid molecule coding for a glucosaminoglycan synthase or to a protein having the activity of a GlcNAc-6-P acetyltransferase or to a protein having the activity of a UDP-GlcNAc pyrophosphorylase in a genetically modified plant cell according to the invention or a genetically modified plant according to the invention.

A preferred embodiment of the present invention relates to genetically modified plant cells according to the invention or genetically modified plants according to the invention where at least one foreign nucleic acid molecule, particularly preferably at least two foreign nucleic acid molecules, especially preferably three foreign nucleic acid molecules selected from the group consisting of nucleic acid molecules coding for a glucosaminoglycan synthase or a protein having the activity of a GlcNAc-6-P acetyltransferase or a protein having the activity of a UDP-GlcNAc pyrophosphorylase is (are) linked to a tissue-specific promoter. Preferred tissue-specific promoters are promoters which initiate the initiation of the transcription specifically in plant tuber, fruit or seed cells or leaves.

In general, each promoter which is active in plant cells is suitable for the expression of nucleic acid molecules coding for a glucosaminoglycan synthase or a protein having the activity of a GlcNAc-6-P acetyltransferase or a protein having the activity of a UDP-GlcNAc pyrophosphorylase.

Here, the promoter may be chosen such that expression is constitutively or only in a certain tissue, at a certain point of the development of the plant or at a point of time determined by external factors. Both in respect to the plant and in respect of the nucleic acid molecule to be expressed, the promoter may be homologous or heterologous.

Suitable promoters are, for example, the promoter of 35S RNS of the cauliflower mosaic virus or the ubiquitin promoter from corn Christensen and Quail, 1996, Transgenic Research 5(3), 213-218), the kafirin promoter from millet (De Rose et al., 1996, Plant Molecular Biology 32 1029-1035; Mishra et al., 2007, Molecular Biology Reports online: 2 Feb. 2007, DOI: 10.1007/s11033-007-9056-8) or the *Cestrum* YLCV promoter (Yellow Leaf Curling Virus; WO 01 73087; Stavolone et al., 2003, Plant Mol. Biol. 53, 703-713) for a constitutive expression, the patatingen promoter B33 (Rocha-Sosa et al., EMBO J. 8 (1989), 23-29) for a tuber-specific expression in potatoes or a fruit-specific promoter for tomato, such as, for example, the polygalacturonase promoter from tomato (Montgomery et al., 1993, Plant Cell 5, 1049-1062) or the E8 promoter from tomato (Metha et al., 2002, Nature Biotechnol. 20(6), 613-618) or the ACC oxidase promoter from peach (Moon and Callahan, 2004, J. Experimental Botany 55 (402), 1519-1528) or a promoter which ensures expression only in photosynthetically active tissues, for example the ST-LS1 promoter (Stockhaus et al., Proc. Natl. Acad. Sci. USA 84 (1987), 7943-7947; Stockhaus et al., EMBO J. 8 (1989), 2445-2451) or for an endosperm-specific expression the HMWG promoter from wheat, the USP promoter, the phaseolin promoter, promoters of zein genes from corn (Pedersen et al., Cell 29 (1982), 1015-1026; Quatroccio et al., Plant Mol. Biol. 15 (1990), 81-93), the glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218) or the shrunken-1 promoter (Werr et al., EMBO J. 4 (1985), 1373-1380). However, it is also possible to use promoters which are only active at a point in time determined by external factors (see, for example, WO 9307279). Of particular interest here may be promoters of heat-shock proteins which permit a simple induction. It is furthermore possible to use seed-specific promoters, such as, for example, the USP promoter from *Vicia faba* which ensures a seed-specific expression in *Vicia faba* and other plants (Fiedler et al., Plant Mol. Biol. 22 (1993), 669-679; Bäumlein et al., Mol. Gen. Genet. 225 (1991), 459-467).

The use of promoters present in the genome of algae-infecting viruses are also suitable for expressing nucleic acid sequences in plants (Mitra et al., 1994, Biochem. Biophys Res Commun 204(1), 187-194; Mitra and Higgins, 1994, Plant Mol Biol 26(1), 85-93, Van Etten et al., 2002, Arch Virol 147, 1479-1516).

In the context of the present invention, the term "tissue specific" is to be understood as meaning the substantial limitation of a manifestation (for example initiation of transcription) to a certain tissue.

In the context of the present invention, the terms "tuber, fruit or seed cell" are to be understood as meaning all cells present in a tuber, a fruit or in a seed.

In the context of the present invention, the term "homologous promoter" is to be understood as meaning a promoter which is naturally present in plant cells or plants used for the production of genetically modified plant cells according to the invention or genetically modified plants according to the invention (homologous with respect to the plant cell or the plant) or as meaning a promoter which regulates the regulation of the expression of a gene in the organism from which the sequence was isolated (homologous with respect to the nucleic acid molecule to be expressed).

In the context of the present invention, the term "heterologous promoter" is to be understood as meaning a promoter which is not naturally present in plant cells or plants used for the production of genetically modified plant cells according to the invention or genetically modified plants according to the invention (heterologous with respect to the plant cell or plant) or as meaning a promoter which is, in the organism from which a nucleic acid sequence to be expressed was isolated, not naturally present for regulating the expression of said nucleic acid sequence (heterologous with respect to the gene to be expressed).

Also present may be a termination sequence (polyadenylation signal) which serves to add a poly-A tail to the mRNA transcript of the nucleic acid molecule. The poly-A tail is thought to act in stabilizing the transcripts. Such elements are described in the literature (cf. Gielen et al., EMBO J. 8 (1989), 23-29) and can be exchanged as desired.

It is also possible for intron sequences to be present between the promoter and the coding region or in the foreign nucleic acid molecule, coding for a protein. Such intron sequences may lead to stability of expression and in increased expression in plants (Callis et al., 1987, Genes Devel. 1, 1183-1200; Luehrsen, and Walbot, 1991, Mol. Gen. Genet. 225, 81-93; Rethmeier et al., 1997; Plant Journal 12(4), 895-899; Rose and Beliakoff, 2000, Plant Physiol. 122 (2), 535-542; Vasil et al., 1989, Plant Physiol. 91, 1575-1579; X U et al., 2003, Science in China Series C Vol. 46 No. 6, 561-569). Suitable intron sequences are, for example, the first intron of the sh1 gene from corn, the first intron of the poly-ubiquitin gene 1 from corn, the first intron of the EPSPS gene from rice or one of the first two introns of the PAT1 gene from *Arabidopsis*.

The present invention also relates to plants comprising genetically modified plant cells according to the invention. Such plants may be produced by regeneration from genetically modified plant cells according to the invention.

In a further embodiment, the present invention relates to harvestable plant parts of genetically modified plants according to the invention, such as fruits, storage and other roots, flowers, buds, shoots, leaves or stalks, preferably seeds, fruits or tubers, these harvestable parts comprising genetically modified plant cells according to the invention.

In a preferred embodiment of the present invention, the harvestable plant parts according to the invention are processable or consumable parts of genetically modified plants according to the invention comprising genetically modified plant cells according to the invention.

In the context of the present invention, the term "processable parts" is to be understood as meaning plant parts which are used for preparing foodstuff or feedstuff, which are used as a raw material source for industrial processes, as a raw material source for the production of pharmaceutical products or as a raw material source for the production of cosmetic products.

In the context of the present invention, the term "consumable parts" is to be understood as meaning plant parts which serve as food for man or are used as animal feed.

The present invention also relates to a propagation material of genetically modified plants according to the invention comprising a genetically modified plant cell according to the invention.

Here, the term "propagation material" comprises those components of the plant which are suitable for generating progeny via the vegetative or sexual route. Suitable for vegetative propagation are, for example, cuttings, callus cultures, rhizomes or tubers but also e.g. protoplasts and cell cultures. Propagation material produced by means of sexual processes includes, for example, fruits, seeds, seedlings, etc. The propagation material preferably takes the form of tubers, fruits or seeds.

Preferably, the present invention relates to propagation material according to the invention or harvestable parts of plants according to the invention comprising glucosaminoglycan (for example hyaluronan). Particularly preferably, the propagation material according to the invention or the harvestable parts of plants according to the invention is/are propagation material according to the invention or harvestable parts of plants according to the invention synthesizing glucosaminoglycan. Preferably, said glucosaminoglycan is chondroitin, heparin/heparan or hyaluronan, particularly preferably hyaluronan.

In the context of the present invention, the term "potato plant" or "potato" is to be understood as meaning plant species of the genus *Solanum*, particularly tuber-producing species of the genus *Solanum* and in particular *Solanum tuberosum*.

In the context of the present invention, the term "tomato plant" or "tomato" is to be understood as meaning plant species of the genus *Lycopersicon*, in particular *Lycopersicon esculentum*.

A further advantage of the present invention is that harvestable parts, propagation material, processible parts or consumable parts of genetically modified plants according to the invention comprise more glucosaminoglycan (for example hyaluronan) than plants comprising only a foreign nucleic acid molecule coding for a glucosamine synthase. Accordingly, genetically modified plants according to the invention are not only particularly suitable for use as raw material from which glucosaminoglycan (for example hyaluronan) may be isolated but can also be used directly as foodstuff/feedstuff or for preparing foodstuff/feedstuff having a prophylactic or therapeutic character (for example for osteoarthritis prophylaxis, U.S. Pat. No. 6,607,745). Since genetically modified plants according to the invention have a higher glucosaminoglycan content than plants having only a foreign nucleic acid molecule, coding for a glucosaminoglycan synthase, the production of such foodstuff/feedstuff requires lower amounts of harvestable parts, propagation material, processible parts or consumable parts of genetically modified plants according to the invention. If consumable parts of genetically modified plants according to the invention are consumed, for example, directly as a so-called "nutraceutical", it is possible to achieve a positive effect even by ingesting relatively small amounts of substance. This may be of particular significance inter alia in the production of animal feed, since animal feed having too high a content of plant components is unsuitable as feedstuff for various animal species.

By virtue of the high capacity of glucosaminoglycans, in particular hyaluronan, to bind water, harvestable parts, propagation material, processible parts or consumable parts of genetically modified plants according to the invention furthermore have the advantage that less thickeners are required when solidified foodstuff/feedstuff is produced. Thus, for example, the production of jelly requires less sugar, which is associated with an additional positive effect on health. In the production of foodstuff/feedstuff requiring the dehydration of the crude plant material, the advantage of using harvestable parts, propagation material, processible parts or consumable parts of genetically modified plants according to the invention consists in the fact that less water has to be removed from the plant material in question, resulting in lower production costs and, owing to more gentle preparation methods (for example lower and/or shorter input of heat), an elevated nutritional value of the foodstuff/feedstuff in question. Thus, for example, in the production of tomato ketchup less energy has to be introduced in order to achieve the desired consistency.

The present invention furthermore provides a process for producing a plant, which comprises
a) genetically modifying a plant cell, where the genetic modification comprises steps i to iii below
   i) introduction of a foreign nucleic acid molecule coding for a glucosaminoglycan synthase into a plant cell
   ii) introduction of a foreign nucleic acid molecule coding for a glucosamine 6-phosphate acetyltransferase into a plant cell
   iii) introduction of a foreign nucleic acid molecule coding for a UDP-N-acetyl-glucosamine pyrophosphorylase into a plant cell
where steps i to iii can be carried out in any order, individually or any combinations of steps i to iii may be carried out simultaneously
b) regenerating a plant from plant cells from step a) i and/or a) ii and/or a) iii;
c) generating, if appropriate, further plants using the plants according to step b),
where, if appropriate, plant cells are isolated from plants according to step b) or c) and the process steps a) to c) are repeated until a plant is generated which has a foreign nucleic acid molecule coding for a glucosaminoglycan synthase and a foreign nucleic acid molecule coding for a protein having the activity of a glucosamine 6-phosphate acetyltransferase and a foreign nucleic acid molecule coding for a protein having the activity of a UDP-GlcNAc pyrophosphorylase.

A preferred embodiment of the process according to the invention for producing a plant relates to a process for preparing a plant, which comprises
a) genetically modifying a plant cell, where the genetic modification comprises steps i to iii below in any order or any combinations of the following steps i to iii carried out individually or simultaneously
   i) introduction of a foreign nucleic acid molecule coding for a glucosaminoglycan synthase into the plant cell
   ii) introduction of a foreign nucleic acid molecule coding for a glucosamine 6-phosphate acetyltransferase into a plant cell
   iii) introduction of a foreign nucleic acid molecule coding for a UDP-GlcNAc pyrophosphorylase into a plant cell
b) regenerating a plant from plant cells comprising the genetic modification according to steps
   i) a) i
   ii) a) ii
   iii) a) iii
   iv) a) i and a) ii,
   v) a) i and a) iii,
   vi) a) ii and a) iii, or
   vii) a) i and a) ii and a) iii
c) introducing into plant cells of plants according to step
   i) b) i a genetic modification according to step a) ii,
   ii) b) i a genetic modification according to step a) iii,
   iii) b) i a genetic modification according to step a) ii and at the same time a genetic modification according to step a) iii,
   iv) b) ii a genetic modification according to step a) i,
   v) b) ii a genetic modification according to step a)
   vi) b) ii a genetic modification according to step a) i and at the same time a genetic modification according to step a) iii,
   vii) b) iii a genetic modification according to step a) i,
   viii) b) iii a genetic modification according to step a) ii,
   ix) b) iii a genetic modification according to step a) i and at the same time a genetic modification according to step a) ii,
   x) b) iv a genetic modification according to step a) iii,
   xi) b) v a genetic modification according to step a) ii, or
   xii) b) vi a genetic modification according to step a) i
and regenerating a plant
d) introducing into plant cells of plants according to step
   i) c) i a genetic modification according to step a) iii,
   ii) c) ii a genetic modification according to step a) ii,
   iii) c) iv a genetic modification according to step a) iii,
   iv) c) v a genetic modification according to step a) ii,
   v) c) vii a genetic modification according to step a) ii,
   vi) c) vii a genetic modification according to step a) i, or
   vii) c) ix a genetic modification according to step a) ii
and regenerating a plant
e) if appropriate generating further plants with the aid of the plants according to any of steps b) vii c) iii, c) vi, c) x, c) xi, c) xii or according to any of steps d) i to d) vii.

For introducing foreign nucleic acid molecules according to step a) of the process according to the invention for producing a plant, any available method may be used. Various processes for the transformation of plant cells have already been described above and can be applied here in a corresponding manner. If the process steps according to step a) of the process according to the invention for producing a plant are not carried out simultaneously but in succession, identical or different methods may be used for the individual transformation steps.

The regeneration of the plants according to step b) and, if appropriate, steps c) and d) of the processes according to the invention for producing a plant can be carried out by methods known to the person skilled in the art (described, for example, in "Plant Cell Culture Protocols", 1999, edt. by R. D. Hall, Humana Press, ISBN 0-89603-549-2).

The generation of further plants (according to step c) or step e), depending on the process) of the processes according to the invention for producing a plant may take place, for example, by vegetative propagation (for example via cuttings, tubers or via callus cultivation and regeneration of entire plants) or by sexual propagation. Here, sexual propagation is preferably carried out in a controlled manner, i.e. selected plants with certain properties are crossed with one another and propagated. Selection is preferably carried out such that the further plants (which, depending on the process, are generated according to step c) or step e)) have the foreign nucleic acid molecules introduced in the preceding steps.

In the processes according to the invention for producing plants, the genetic modifications for generating the genetically modified plant cells according to the invention can be carried out simultaneously or in successive steps and in any combination. It is possible to use both wild-type plants and wild-type plant cells into which a foreign nucleic acid molecule has not yet been introduced, or it is possible to use plant cells or plants which are already genetically modified and into which one or more foreign nucleic acid molecules have already been introduced.

In the genetic modification of introducing the foreign nucleic acid molecules into the plant cell or the plant, in step a) of the process according to the invention for producing a plant the foreign nucleic acid molecules may be a single nucleic acid molecule or a plurality of nucleic acid molecules. Thus, the foreign nucleic acid molecules coding for a glucosaminoglycan synthase or coding for a protein having the enyzmatic activity of a GlcNAc-6-P acetyltransferase or coding for a protein having the enyzmatic activity of a UDP-GlcNAc pyrophosphorylase can be present together on a single nucleic acid molecule, or two of the foreign nucleic acid molecules mentioned may be present together on a single nucleic acid molecule and the third foreign nucleic acid molecule may be present on another nucleic acid molecule in any possible combination, or all three of the foreign nucleic acid molecules mentioned may each be present on individual separate nucleic acid molecules.

Preferred properties of foreign nucleic acid molecules or recombinant nucleic acid molecules have already been described above in connection with plant cells according to the invention or plants according to the invention, and they can be applied correspondingly in the practice of processes according to the invention for producing a plant.

In a further preferred embodiment, processes according to the invention for producing a plant are used for producing genetically modified plants according to the invention.

The present invention also provides plants obtainable by a process according to the invention for producing a plant which synthesizes hyaluronan.

The present invention furthermore relates to a process for producing glucosaminoglycans (for example hyaluronan) which comprises the step of extracting glucosaminoglycans from genetically modified plant cells according to the invention, from genetically modified plants according to the invention, from propagation material according to the invention, from harvestable plant parts according to the invention or from plants or parts of these plants obtainable by a process according to the invention for producing plants. Preferably, such a process also comprises the step of harvesting the cultivated genetically modified plant cells according to the invention, the genetically modified plants according to the invention, the propagation material according to the invention, the harvestable plant parts according to the invention, the processible plant parts according to the invention prior to extracting the glucosaminoglycan (for example hyaluronan) and particularly preferably furthermore the step of cultivating genetically modified plant cells according to the invention or genetically modified plants according to the invention prior to harvesting.

In contrast to bacterial or animal tissues, plant tissues have no glucosaminoglycan-degrading enzymes (for example hyaluronidases). Accordingly, as already described above, extraction of glucosaminoglycans from plant tissues is possible using relatively simple methods. If required, the aqueous extracts, described above, of plant cells or tissues containing glucosaminoglycans can be purified further using methods known to the person skilled in the art, such as, for example, repeated precipitation with ethanol. A preferred method for purifying hyaluronan is described under General Methods item 3.

The processes already described for extracting glucosaminoglycans from genetically modified plant cells according to the invention or genetically modified plants according to the invention are also suitable for isolating glucosaminoglycans (for example hyaluronan) from propagation material according to the invention, from harvestable plant parts according to the invention or from plants or parts of these plants obtainable by a process according to the invention for preparing plants which synthesize hyaluronan.

The present invention also provides the use of genetically modified plant cells according to the invention, genetically modified plants according to the invention, propagation material according to the invention, harvestable plant parts according to the invention or plants obtainable by a process according to the invention for producing a plant for preparing glucosaminoglycans.

The present invention furthermore relates to compositions comprising genetically modified plant cells according to the invention. Here, it is immaterial whether the plant cells are intact or no longer intact because they have been destroyed, for example, by processing. The compositions are preferably foodstuff or feedstuff, pharmaceutical or cosmetic products.

The present invention preferably provides compositions comprising components of genetically modified plant cells according to the invention, of genetically modified plants according to the invention, of propagation material according to the invention, of harvestable plant parts according to the invention or of plants obtainable by a process according to the invention and comprising recombinant nucleic acid molecules, where the recombinant nucleic acid molecules are characterized in that they comprise nucleic acid molecules coding for a glucosaminoglycan synthase and proteins having the enzymatic activity of a GlcNAc-6-P acetyltransferase and proteins having the enzymatic activity of a UDP-GlcNAc pyrophosphorylase.

A stable integration of foreign nucleic acid molecules into the genome of a plant cell or plant results in the foreign nucleic acid molecules being flanked after integration into the genome of a plant cell or plant by genomic plant nucleic acid sequences.

Accordingly, in a preferred embodiment, compositions according to the invention are characterized in that the recombinant nucleic acid molecules present in the composition according to the invention are flanked by genomic plant nucleic acid sequences.

Here, the genomic plant nucleic acid sequences may be any sequences naturally present in the genome of the plant cell or plant used for preparing the composition.

The recombinant nucleic acid molecules present in the compositions according to the invention may be individual or different recombinant nucleic acid molecules, in which nucleic acid molecules coding for a glucosaminoglycan synthase (for example hyaluronan synthase) and proteins having the activity of a GlcN-6-P acetyltransferase and proteins having the activity of a UDP-GlcNAc pyrophosphorylase are present in one nucleic acid molecule, or those where the nucleic acid molecules mentioned are present in separate nucleic acid molecules. Nucleic acid molecules coding for a glucosaminoglycan synthase (for example hyaluronan synthase) or coding for a protein having the activity of a GlcN-6-P acetyltransferase or coding for a protein having the activity of a UDP-GlcNAc pyrophosphorylase may be present together on a single recombinant nucleic acid molecule, or two of the nucleic acid molecules mentioned may be present together on a single recombinant nucleic acid molecule and the third nucleic acid molecule may be present on another recombinant nucleic acid molecule in any possible combination, or all three nucleic acid molecules mentioned may in each case be present on individual separate recombinant nucleic acid molecules. Depending on how the nucleic acid molecules coding for a glucosaminoglycan synthase (for example hyaluronan synthase) or coding for a protein having the activity of a GlcN-6-P acetyltransferase or coding for a protein having the activity of a UDP-GlcNAc pyrophosphorylase are present in a composition according to the invention, they may be flanked by identical or different genomic plant nucleic acid sequences.

That compositions according to the invention comprise recombinant nucleic acid molecules may be demonstrated using methods known to the person skilled in the art, such as, for example, methods based on hybridization or, preferably, using methods based on PCR (polymerase chain reaction).

As already mentioned above, it is possible to use genetically modified plant cells according to the invention, genetically modified plants according to the invention, propagation material according to the invention, harvestable plant parts according to the invention, or plants obtainable by a process according to the invention to prepare foodstuff or feedstuff. However, use as raw materials for industrial applications is also possible, without glucosaminoglycans (for example hyaluronan) having to be isolated. Thus, for example, genetically modified plants according to the invention or parts of genetically modified plants according to the invention can be applied to areas under agricultural cultivation to achieve increased water binding of the soil. Furthermore, genetically modified plants according to the invention or genetically modified plant cells according to the invention can be used for preparing drying agents (for example for use when shipping moisture-sensitive items) or as absorbers of liquids (for example in diapers or for absorbing spilt aqueous liquids). For such applications, it is possible to use entire genetically modified plants according to the invention, parts of genetically modified plants according to the invention or comminuted (for example ground) genetically modified plants according to the invention or plant parts according to the invention, as required. Suitable for applications in which ground plants or plant parts are used are in particular plant parts containing glucosaminoglycans (for example hyaluronan), but only a low proportion of water. These are preferably grains of cereal plants (corn, rice, wheat, rye, oats, barley, sago or sorghum). Since genetically modified plant cells according to the invention and genetically modified plants according to the invention have a higher glucosaminoglycan (for example hyaluronan) content than plants which have only one foreign nucleic acid molecule coding for glucosaminoglycan synthase, compared to these less material has to be used for industrial applications when use is made of genetically modified plant cells according to the invention or genetically modified plants according to the invention.

The present invention also provides processes for preparing a composition according to the invention, where genetically modified plant cells according to the invention, genetically modified plants according to the invention, propagation material according to the invention, harvestable plant parts according to the invention, or plants obtainable by a process according to the invention for producing a plant are used. The processes for preparing a composition according to the invention are preferably processes for preparing foodstuff or feedstuff, processes for preparing a pharmaceutical product or processes for preparing a cosmetic product.

Process for preparing foodstuff or feedstuff are known to the person skilled in the art. Processes for using genetically modified plants according to the invention or plant parts according to the invention in industrial areas are also known to the person skilled in the art and include inter alia comminuting or grinding of genetically modified plants according to the invention or plant parts according to the invention; however, they are not exclusively limited thereto. Some of the advantages resulting from using subject-matters according to the invention for preparing foodstuff/feedstuff or for use in industrial areas have already been described above.

A process according to the invention for preparing a composition is particularly preferably a process for preparing a composition which comprises glucosaminoglycan (for example hyaluronan).

Compositions obtainable by a process for preparing a composition according to the invention are likewise provided by the present invention.

The present invention also relates to the use of genetically modified plant cells according to the invention, genetically modified plants according to the invention, propagation material according to the invention, harvestable plant parts according to the invention, or plants obtainable by a process according to the invention for producing a plant for preparing a composition according to the invention. Preference is given to the use of genetically modified plant cells according to the invention, genetically modified plants according to the invention, propagation material according to the invention, harvestable plant parts according to the invention, or of plants obtainable by a process according to the invention for producing a plant for preparing foodstuff or feedstuff, for preparing a pharmaceutic or for preparing a cosmetic product.

Description of the Sequences

SEQ ID NO 1: Nucleic acid sequence coding for a hyaluronan synthase from *Paramecium bursaria Chlorella* virus 1.

SEQ ID NO 2: Amino acid sequence of a hyaluronan synthase from *Paramecium bursaria Chlorella* virus 1. The amino acid sequence shown can be derived from SEQ ID NO 1.

SEQ ID NO 3: Synthetic nucleic acid sequence coding for a hyaluronan synthase from *Paramecium bursaria Chlorella* virus 1. The synthesis of the codons of the sequence shown was performed in a manner that they were adapted to the use of codons in plant cells. The nucleic acid sequence shown codes for a protein having the amino acid sequence shown under SEQ ID No 2.

SEQ ID NO 4: Nucleic acid sequence coding for a protein having the activity of a chondroitin synthase from *Pasteurella multocida*.

SEQ ID NO 5: Amino acid sequence of a protein having the activity of a chondroitin synthase from *Pasteurella multocida*. The amino acid sequence shown can be derived from SEQ ID NO 4.

SEQ ID NO 6: Nucleic acid sequence coding for a protein having the activity of a heparosan synthase from *Pasteurella multocida*.

SEQ ID NO 7: Amino acid sequence of a protein having the activity of a heparosan synthase from *Pasteurella multocida*. The amino acid sequence shown can be derived from SEQ ID NO 6.

SEQ ID NO 8: Nucleic acid sequence coding for a protein having the activity of a GlcN-6-P acetyltransferase from *Saccharomyces cerevisiae*.

SEQ ID NO 9: Amino acid sequence of a protein having the activity of a GlcN-6-P acetyltransferase from *Saccharomyces cerevisiae*. The amino acid sequence shown can be derived from SEQ ID NO 8.

SEQ ID NO 10: Nucleic acid sequence coding for a protein having the activity of a UDP-GlcNAc pyrophosphorylase from *Saccharomyces cerevisiae*.

SEQ ID NO 11: Amino acid sequence of a protein having the activity of a UDP-GlcNAc pyrophosphorylase from *Saccharomyces cerevisiae*. The amino acid sequence shown can be derived from SEQ ID NO 10.

SEQ ID NO 12: Nucleic acid sequence of an expression cassette comprising the YLCV promoter, restriction sites, the polyadenylation signal sequence of the ocs terminator from *Agrobacterium* and the polyadenylation signal sequence of the nos terminators from *Agrobacterium*.

SEQ ID NO 13: Synthetic oligonucleotide for preparing an MCS ("Multiple Cloning Site").

SEQ ID NO 14: Synthetic oligonucleotide for preparing an MCS ("Multiple Cloning Site").

SEQ ID NO 15: Primer used for PCR reactions.
SEQ ID NO 16: Primer used for PCR reactions.
SEQ ID NO 17: Primer used for PCR reactions.
SEQ ID NO 18: Primer used for PCR reactions.
SEQ ID NO 19: Primer used for PCR reactions.
SEQ ID NO 20: Primer used for PCR reactions.
SEQ ID NO 21: Nucleic acid sequence coding for a protein having the activity of a GlcN-1-P mutase from *Escherichia coli*.

SEQ ID NO 22: Amino acid sequence of a protein having the activity of a GlcN-1-P mutase from *Escherichia coli*. The amino acid sequence shown can be derived from SEQ ID NO 21.

SEQ ID NO 23: Synthetic Oligonucleotide used as PCR primer.

SEQ ID NO 24: Synthetic Oligonucleotide used as PCR primer.

SEQ ID NO 25: Nucleic acid sequence coding for a protein having the bifunctional activities of a glucosamine 1-phosphate acetyltransferase and a UDP-GlcNAc pyrophosphorylase from *E. coli* (glmu).

SEQ ID NO 26: Amino acid sequence of a protein having the bifunctional activities of a glucosamine 1-phosphate acetyltransferase and a UDP-GlcNAc pyrophosphorylase from *E. coli*. The amino acid sequence shown can be derived from SEQ ID NO 25.

SEQ ID NO 27: Primer used for PCR reactions.

SEQ ID NO 28: Primer used for PCR reactions.

SEQ ID NO 29: Nucleic acid sequence coding for a protein having the activity of a phosphoacetylglucosamine (GlcN-P) mutase from *Saccharomyces cerevisiae*.

SEQ ID NO: 30 Amino acid sequence of a protein having the activity of a phosphoacetylglucosamine mutase from *Saccharomyces cerevisiae*. The amino acid sequence shown can be derived from SEQ ID NO 30.

General Methods

Methods which can be used in connection with the present invention are described below. These methods are specific embodiments; however, the present invention is not limited to these methods. It is known to the person skilled in the art that the invention can be carried out in the same manner by modifying the methods described and/or by replacing individual methods or parts of methods by alternative methods or alternative parts of methods.

1. Transformation of Potato Plants

Potato plants were transformed with the aid of *Agrobacterium*, as described in Rocha-Sosa et al. (EMBO J. 8, (1989), 23-29).

2. Isolation of Glucosaminoglycan Using the Example of Hyaluronan from Plant Tissue To detect the presence of hyaluronan and to determine the hyaluronan content in plant tissue, plant material was worked up as follows: 200 µl of water (demineralized, conductivity ≥18 MΩ) were added to about 0.3 g of plant material, and the mixture was comminuted in a laboratory oscillating ball mill (MM200, from Retsch, Germany) (30 sec at 30 Hz). A further 800 µl of water (demineralized, conductivity ≥18 MΩ) was then added, and the mixture was mixed well (using, for example, a Vortex mixer). Cell debris and insoluble components were separated from the supernatant by centrifuging at 16 000×g for 5 minutes. To determine the amount of hyaluronan in the entire above-ground parts of plants, the above-ground parts of the plants were cut off about 1 cm to 3 cm above the culture substrate, cut into small pieces and then comminuted using a Warring blender as described under General Methods item 3. To determine the hyaluronan content, an aliquot may then be removed from the centrifugation supernatant obtained (see General Methods item 3).

3. Purification of Glucosaminoglycan Using the Example of Hyaluronan

Comminuted plant material or the entire above-ground part of a plant was, after addition of water (about 100 ml of water, demineralized, conductivity ≥18 MΩ, in each case 100 g of plant material) comminuted in a Warring blender at maximum speed for about 30 seconds. The cell debris was then removed using a tea sieve. The cell debris that had been removed was resuspended in 300 ml of water (demineralized, conductivity ≥18 MΩ) and again removed using a tea sieve. The two suspensions obtained (100 ml+300 ml) were combined and centrifuged at 13 000×g for 15 minutes. NaCl was added to the centrifugation supernatant obtained until a final concentration of 1% had been reached. After the NaCl had gone into solution, precipitation was carried out by addition of twice the volume of ethanol followed by thorough mixing and incubation at −20° C. overnight. The mixture was then centrifuged at 13 000×g for 15 minutes. The sedimented precipitate obtained after this centrifugation was dissolved in 100 ml of buffer (50 mM TrisHCl, pH 8, 1 mM CaCl$_2$) and proteinase K was then added to a final concentration of 100 µg/ml and the solution was incubated at 42° C. for 2 hours. This was followed by 10 minutes of incubation at 95° C. Once more, NaCl was added to this solution until a final concentration of 1% had been reached. After the NaCl had gone into solution, another precipitation was carried out by addition of twice the volume of ethanol, thorough mixing and incubation at −20° C. for about 96 hours. This was followed by 15 minutes of centrifugation at 13 000×g. The sedimented precipitate obtained after this centrifugation was dissolved in 30 ml of water (demineralized, conductivity ≥18 MΩ), and once more, NaCl was added to a final concentration of 1%. By adding twice the volume of ethanol, thorough mixing and incubation at −20° C. overnight, another precipitation was carried out. The precipitate obtained after subsequent centrifugation at 13 000×g for 15 minutes was dissolved in 20 ml of water (demineralized, conductivity ≥18 MΩ).

Further purification was carried out by centrifugal filtration. To this end, in each case 5 ml of the dissolved precipitate were applied to a membrane filter (CentriconAmicon, pore width 10 000 NMWL, Prod. No. UCF8 010 96), and the sample was centrifuged at 2200×g until only about 3 ml of the solution above the filter remained. Two more times, in each case 3 ml of water (demineralized, conductivity ≥18 MΩ) were then added to the solution above the membrane and in each case re-centrifuged under identical conditions until, at the end, only about 3 ml of the solution above the filter remained. The solutions still present above the membrane after centrifugal filtration were taken off, and the membrane was rinsed repeatedly (three to five times) with about 1.5 ml of water (demineralized, conductivity ≥18 MΩ). All solutions which were still present above the membrane and the solutions obtained from rinsing were combined, NaCl was added to a final concentration of 1%, after the NaCl had gone into solution, twice the volume of ethanol was added, the sample was mixed and a precipitate was obtained by storage at −20° C. overnight. The precipitate obtained after subsequent centrifugation at 13 000×g for 15 minutes was dissolved in 4 ml of water (demineralized, conductivity ≥18 MΩ) and then freeze-dried (24 hours under a pressure of 0.37 mbar, freeze drying apparatus Christ Alpha 1-4 from Christ, Osterode, Germany).

4. Detection of Hyaluronan and Determination of the Hyaluronan Content

Hyaluronan was detected using a commercial test (hyaluronic acid (HA) test kit from Corgenix, Inc., Colorado, USA, Prod. No. 029-001) according to the instructions of the manufacturer which are herewith incorporated into the description by way of reference. The test principle is based on the availability of a protein which binds specifically to hyaluronan (HABP) and is carried out similarly to an ELISA, where a color reaction indicates the hyaluronan content in the sample examined. The hyaluronan values are determined with the aid of a calibration curve using defined amounts of hyaluronan which are included with the test kit. Accordingly, for the quantitative determination of hyaluronan, the samples to be measured should be employed in a concentration such that it is within the stated limits (for example: dilution of the sample in question or use of less water for extracting hyaluronan from plant tissue, depending on whether a limit was exceeded or not reached).

In parallel batches, aliquots of the samples to be determined were initially subjected to hyaluronidase digestion and then measured using the commercial test (hyaluronic acid (HA) test kit from Corgenix, Inc., Colorado, USA, Prod. No. 029-001). Hyaluronidase digestion was carried out using 400 µl of plant extract in hyaluronidase buffer (0.1 M potassium phosphate buffer, pH 5.3; 150 mM NaCl) by adding 5 µg (~3 units) of hyaluronidase (hyaluronidase type III from Sigma, Prod. No. H 2251) and incubating at 37° C. for 30 min.

In each case in a dilution of 1:10, all samples were then used for determining the hyaluronan content.

5. Determination of the Activity of a GFAT

The activity of a protein having the activity of GFAT is determined as described in Rachel et al. (1996, J. Bacteriol. 178 (8), 2320-2327).

To distinguish whether a protein has the activity of a GFAT-1 or GFAT-2, the method described in Hu et al. (2004, J. Biol. Chem. 279 (29), 29988-29993) is used.

EXAMPLES

1. Preparation of the Plant Expression Vector IR 47-71

The plasmid pBinAR is a derivative of the binary vector plasmid pBin19 (Bevan, 1984, Nucl Acids Res 12: 8711-8721) which was constructed as follows:

A fragment of a length of 529 bp which comprised the nucleotides 6909-7437 of the $^{35}$S promoter of the cauliflower mosaic virus was isolated as EcoR I/Kpn I fragment from the plasmid pDH51 (Pietrzak et al, 1986 Nucleic Acids Res. 14, 5858) and ligated between the EcoR I and Kpn I restriction sites of the polylinker of pUC18. In this manner, the plasmid pUC18-35S was formed. Using the restriction endonucleases Hind III and Pvu II, a fragment of a length of 192 bp which included the polyadenylation signal (3' terminus) of the Octopin Synthase gene (gene 3) of the T-DNA of the Ti plasmid pTiACH5 (Gielen et al, 1984, EMBO Journal 3, 835-846) (nucleotides 11 749-11 939) was isolated from the plasmid pAGV40 (Herrera-Estrella et al, 1983 Nature, 303, 209-213). Following addition of Sph I linkers to the Pvu restriction site, the fragment was ligated between the Sph I and Hind III restriction sites of pUC18-35S. This gave the plasmid pA7. Here, the entire polylinker comprising the 35S promoter and Ocs terminator was removed using EcoR I and Hind III and ligated into the appropriately cleaved vector pBin19. This gave the plant expression vector pBinAR (Höfgen and Willmitzer, 1990, Plant Science 66, 221-230). The promoter of the patatin gene B33 from Solanum tuberosum (Rocha-Sosa et al., 1989, EMBO J. 8, 23-29) was, as Dra I fragment (nucleotides-1512-+14), ligated into the Sst I-cleaved vector pUC19 whose ends had been blunted using T4-DNA polymerase. This gave the plasmid pUC19-B33. From this plasmid, the B33 promoter was removed using EcoR I and Sma I and ligated into the appropriately restricted vector pBinAR. This gave the plant expression vector pBinB33.

To facilitate further cloning steps, the MCS (Multiple Cloning Site) was extended. To this end, two complementary oligonucleotides were synthesized, heated at 95° C. for 5 minutes, slowly cooled to room temperature to allow good annealing and cloned into the Sal I and Kpn I restriction sites of pBinB33. The oligonucleotides used for this purpose are shown under SEQ ID NO 13 and SEQ ID NO 14. The plasmid obtained was named IR 47-71.

2. Preparation of the Plant Expression Vector pBinARHyg

The fragment comprising the 35S promoter, the Ocs terminator and the entire Multiple Cloning Site was removed from pA7 using the restriction endonucleases EcoR I and Hind III and cloned into the vector pBIBHyg (Becker, 1990, Nucleic Acids Res. 18, 203) which had been cut using the same restriction endonucleases. The plasmid obtained was named pBinARHyg.

3. Preparation of the Cloning Vector IC 317-204

Using the restriction endonucleases Xho I and Hind III, nucleic acid fragments comprising the ocs terminator were isolated from the plasmid IR 47-71 and cloned into the vector pBlueScript KS (from Stratagene, Prod. No. 212207), which had been cut with the same restriction endonucleases. The plasmid obtained was named IC 306-204.

Using the restriction endonucleases Bam HI and Eco RI, nucleic acid fragments comprising the B33 promoter were isolated from the plasmid IR 47-71 and cloned into the vector pBlueScript KS (from Stratagene, Prod. No. 212207), which had been cut with the same restriction endonucleases. The plasmid obtained was named IC 314-204.

From IC 306-204, the OCS terminator was isolated using the restriction endonuclease Bam HI and cloned into the plasmid IC 314-204, which had been cut with the same restriction endonuclease. The plasmid obtained was named IC 317-204.

4. Synthesis of Nucleic Acid Molecules a) Synthesis of Nucleic Acid Molecules Coding for a Hyaluronan Synthase from Paramecium bursaria Chlorella Virus 1

The nucleic acid sequence coding for a hyaluronan synthase of Paramecium bursaria Chlorella virus 1 was synthesized by Medigenomix GmbH (Munich, Germany) and cloned into the vector pCR2.1 from Invitrogen (Prod. No. K2000-01). The plasmid obtained was named IC 323-215. The synthetic nucleic acid sequence coding for the HAS protein from Paramecium bursaria Chlorella virus 1, is shown under SEQ ID NO 3. The corresponding nucleic acid sequence originally isolated from the Paramecium bursariai Chlorella virus 1 is shown under SEQ ID NO 1.

b) Synthesis of the Nucleic Acid Sequences Comprising a YLCV Promoter and an MCS, an nos Terminator and an ocs Terminator The nucleic acid sequence comprising a YLCV promoter (Stavolone et al., Plant Molecular Biology 53: 703-713, 2003) and an MCS ("Multiple Cloning Site") containing the restriction sites Sac I and Sma I, an nos terminator and an ocs terminator was synthesized by Entelechon GmbH and cloned into the vector pCR4Topo from Invitrogen (Prod. No. K4510-20). The plasmid obtained was named IC 389-337. The synthetic nucleic acid sequence is shown under SEQ ID NO 12.

5. Isolation of Nucleic Acid Molecules a) Isolation and Cloning of a Coding Nucleic Acid Sequence for a Protein Having the Activity of a GlcN-6-P Acetyltransferase The nucleic acid sequence coding for a protein having the activity of a GlcN-6-P acetyltransferase from Saccharomyces

*cerevisiae* (gna1) was isolated by PCR and cloned into the vector pCR 2.1 from Invitrogen (Prod. No. K4510-20). The reaction conditions for the PCR were as follows:

| 1. step: | 5 min 94° C., |
|---|---|
| 2. step: | 45 sec, 94° C. |
| 3. step: | 45 sec, 59° C. |
| 4. step: | 45 sec, 72° C. |
| 5. step: | 10 min, 72° C. |
| 6. step: | 4° C. |

Steps 2 to 4 were repeated 35 times, and the procedure was then continued with step 5.

The 50 µl reaction batch contained buffer (10 mM Tris-HCl, pH 9.0, 50 mM KCl and 3 mM MgSO$_4$), in each case 500 nM of amplification primer, shown under SEQ ID NO 15 and SEQ ID NO 16, 10 µl of Q-solution (contained in Qiagen, Prod. No. 206143), in each case 0.2 mM of deoxyribonucleotide, 0.5 µl of Taq DNA polymerase (Invitrogen, Prod. No.: 11304-011) and 250 ng of genomic yeast DNA as template. The PCR was carried out using the Mastercycler from Eppendorf (Prod. NR. 5331 000.010).

The isolated nucleic acid sequence coding for the protein having the activity of a GlcN-6-P acetyltransferase from *Saccharomyces cerevisiae* is shown under SEQ ID NO 8.

After cloning of the fragment obtained into the vector pCR 2.1 and confirmation of the sequence, the nucleic acid sequence in question coding for a protein having the activity of a GlcN-6-P acetyltransferase from *Saccharomyces cerevisiae* was isolated using the restriction endonucleases Kpn I and Xba I and cloned into the vector pA7, which had been cut with the same restriction endonucleases. The plasmid obtained was named IC 298-204.

b) Isolation and Cloning of a Nucleic Acid Sequence Coding for a Protein Having the Activity of a UDP-GlcNAc Pyrophosphorylase The nucleic acid sequence coding for a protein having the activity of a UDP-GlcNAc pyrophosphorylase from *Saccharomyces cerevisiae* (qn) was isolated by PCR and cloned into the vector pCR 2.1 from Invitrogen (Prod. No. K2000-01). The reaction conditions for the PCR were as follows:

| 1. step: | 5 min 94° C., |
|---|---|
| 2. step: | 45 sec, 94° C. |
| 3. step: | 45 sec, 59° C. |
| 4. step: | 45 sec, 72° C. |
| 5. step: | 30 min, 72° C. |
| 6. step: | 4° C. |

Steps 2 to 4 were repeated 35 times, and the procedure was then continued with step 5.

The 50 µl reaction batch contained buffer (10 mM Tris-HCl, pH 9.0, 50 mM KCl and 3 mM MgSO$_4$), in each case 500 nM of amplification primer, shown under SEQ ID NO 17 and SEQ ID NO 18, 10 µl of Q-solution (contained in Qiagen, Prod. No.: 206143), in each case 0.2 mM of deoxyribonucleotide, 0.5 µl of Taq DNA polymerase (Invitrogen, Prod. No.: 11304-011) and 250 ng of genomic yeast DNA (Invitrogen Prod. No. 40802) as template. The PCR was carried out using the Mastercycler from Eppendorf (Prod. No. 5331 000.010).

The isolated nucleic acid sequence coding for the protein having the activity of a UDP-GlcNAc pyrophosphorylase from *Saccharomyces cerevisiae* is shown under SEQ ID NO 10.

After cloning of the fragment obtained into the vector pCR 2.1 and confirmation of the sequence, the nucleic acid sequence coding for a protein having the activity of a UDP-GlcNAc pyrophosphorylase from *Saccharomyces cerevisiae* was isolated using the restriction endonucleases Kpn I and Xba I and cloned into the vector pA7, which had been cut with the same restriction endonucleases. The plasmid obtained was named IC 303-204.

c) Isolation and Cloning of a Nucleic Acid Sequence Coding for a Protein Having the Activity of a GlcNAc-P Mutase The nucleic acid sequence coding for a protein having the activity of a phosphoacetylglucosamine mutase from *Saccharomyces cerevisiae* (pcm I, EC 5.4.2.3) was isolated by PCR and cloned into the vector pCR 2.1 from Invitrogen (Prod. No. K2000-01). The reaction conditions for the PCR were as follows:

| 1. step: | 5 min 94° C., |
|---|---|
| 2. step: | 45 sec, 94° C. |
| 3. step: | 45 sec, 59° C. |
| 4. step: | 45 sec, 72° C. |
| 5. step: | 30 min, 72° C. |
| 6. step: | 4° C. |

Steps 2 to 4 were repeated 35 times, and the procedure was then continued with step 5.

The 50 µl reaction batch contained buffer (10 mM Tris-HCl, pH 9.0, 50 mM KCl and 3 mM MgSO4), in each case 500 nM of amplification primer, shown under SEQ ID NO 27 and SEQ ID NO 28, 10 µl of Q-solution (contained in Qiagen, Prod. No.: 206143), in each case 0.2 mM of deoxyribonucleotide, 0.5 µl of Taq DNA polymerase (Invitrogen, Prod. No.: 11304-011) and 250 ng of genomic yeast DNA (Invitrogen Prod. No. 40802) as template. The PCR was carried out using the Mastercycler from Eppendorf (Prod. No. 5331 000.010).

After cloning of the fragment obtained into the vector pCR 2.1 and confirmation of the sequence, the nucleic acid sequence coding for a protein having the activity of a phosphoacetylglucosamine mutase from *Saccharomyces cerevisiae* was isolated using the restriction endonucleases Kpn I and Xba I and cloned into the vector pA7, which had been cut with the same restriction endonucleases. The plasmid obtained was named IC 304-204.

d) Isolation and Cloning of a Nucleic Acid Sequence Coding for a Protein Having the Activity of a GlcN-1-P Mutase from *Escherichia coli*

The nucleic acid sequence coding for a protein having the activity of a glucosamine 1-phosphate mutase (GlcN-1-P mutase) from *E. coli* (glmm) was isolated by PCR and cloned into the vector pCR 2.1 from Invitrogen (Prod. No. K2000-01). The reaction conditions for the PCR were as follows:

| 1. step: | 5 min 94° C., |
|---|---|
| 2. step: | 45 sec, 94° C. |
| 3. step: | 45 sec, 59° C. |
| 4. step: | 45 sec, 72° C. |
| 5. step: | 30 min, 72° C. |
| 6. step: | 4° C. |

Steps 2 to 4 were repeated 35 times, and the procedure was then continued with step 5.

The 50 µl reaction batch contained buffer (10 mM Tris-HCl, pH 9.0, 50 mM KCl and 3 mM MgSO$_4$), in each case 500 nM of amplification primer, shown under SEQ ID NO 19 and SEQ ID NO 20, 10 µl of Q-solution (contained in Qiagen, Prod. No.: 206143), in each case 0.2 mM of deoxyribonucleotide, 0.5 µl of Taq DNA polymerase (Invitrogen, Prod. No.: 11304-011) and 250 ng of genomic *E. coli* DNA as template.

The PCR was carried out using the Mastercycler from Eppendorf (Prod. No. 5331 000.010).

The isolated nucleic acid sequence coding for the protein having the activity of a glucosamine 1-phosphate mutase protein from *E. coli* (glmm) is shown under SEQ ID NO 21

After cloning of the fragment obtained into the vector pCR 2.1 and confirmation of the sequence, the nucleic acid sequence coding for a protein having the activity of a GlcN-1-P mutase from *E. coli* was isolated using the restriction endonucleases Kpn I and Xba I and cloned into the vector pA7, which had been cut with the same restriction endonucleases. The plasmid obtained was named IC 300-204.

e) Isolation and Cloning of a Nucleic Acid Sequence Coding for a Protein Having the Bifunctional Activity of a GlcN-1-P Acetyltransferase and a UDP-GlcNAc-1-P Pyrophosphorylase from *Escherichia coli*

The nucleic acid sequence coding for a bifunctional protein having the activity of a glucosamine 1-phosphate acetyltransferase and a UDP-GlcNAc pyrophosphorylase from *E. coli* (glmu) was isolated by PCR and cloned into the vector pCR2.1 from Invitrogen (Prod. No. K2000-01). The reaction conditions for the PCR were as follows:

| | |
|---|---|
| 1. step: | 5 min 94° C., |
| 2. step: | 45 sec, 94° C. |
| 3. step: | 45 sec, 59° C. |
| 4. step: | 45 sec, 72° C. |
| 5. step: | 30 min, 72° C. |
| 6. step: | 4° C. |

Steps 2 to 4 were repeated 35 times, and the procedure was then continued with step 5.

The 50 µl reaction batch contained buffer (10 mM Tris-HCl, pH 9.0, 50 mM KCl and 3 mM MgSO$_4$), in each case 500 nM of amplification primer, shown under SEQ ID NO 23 and SEQ ID NO 24, 10 µl of Q-solution (contained in Qiagen, Prod. No.: 206143), in each case 0.2 mM of deoxyribonucleotide, 0.5 µl of Taq DNA polymerase (Invitrogen, Prod. No.: 11304-011) and 250 ng of genomic *E. coli* DNA as template. The PCR was carried out using the Mastercycler from Eppendorf (Prod. No. 5331 000.010).

The isolated nucleic acid sequence coding for a protein having the bifunctional activities of a glucosamine 1-phosphate acetyltransferase and a UDP-GlcNAc pyrophosphorylase from *E. coli* (glmu) is shown under SEQ ID NO 25.

After cloning of the fragment obtained into the vector pCR 21 and confirmation of the sequence, the nucleic acid sequence coding for a bifunctional protein having the activity of a GlcN-1-P acetyltransferase and a UDP-GlcNAc pyrophosphorylase from *E. coli* (glmu) was isolated using the restriction endonucleases Kpn I and Xba I and cloned into the vector pA7, which had been cut with the same restriction endonucleases. The plasmid obtained was named IC 299-204.

6. Preparation of the Plant Expression Vector IC 341-222 Comprising a Coding Nucleic Acid Sequence for a Hyaluronan Synthase from *Paramecium bursaria Chlorella* Virus 1

Nucleic acid molecules comprising the coding sequence of the hyaluronan synthase, were isolated from the plasmid IC 323-215 by restriction digestion with BamH I and Xho I and cloned into the BamH I and Xho I restriction sites of the plasmid IR 47-71. The plant expression vector obtained was named IC 341-222.

7. Preparation of the Plant Expression Vector IC 351-222 Comprising a Coding Nucleic Acid Sequence for a Protein Having the Activity of a GlcN-6-P Acetyltransferase from *Saccharomyces cerevisiae*

Starting plasmid is the above-described plant expression vector pUBI bar (WO 97 44472) into whose EcoR I and Sda I restriction sites the coding sequence of the gna gene from yeast was cloned. The coding sequence of the gna gene from yeast was isolated by EcoR I and Sda I restriction digestion from the plasmid IC 298-204. The vector obtained was named IC 351-222.

8. Preparation of the Plant Expression Vector IC 392-337 Containing Coding Nucleic Acid Sequences for a Protein Having the Activity of a GlcN-6-P Acetyltransferase and a Protein Having the Activity of a UDP-GlcNAc Pyrophosphorylase Starting plasmid is the plasmid IC 351-222 described further above into whose Eco RI restriction site the cassette of YLCV promoter and NOS terminator and OCS terminator, isolated using the restriction endonuclease Eco RI from the plasmid IC 389-337, was cloned. The vector obtained was named IC 390-337.

From the above-described plasmid IC 303-204, the coding sequence of the qri gene was isolated by Sac I and Eco RV restriction digestion and ligated into the Sac I and Sma I restriction sites of the vector IC 390-337. The vector obtained was named IC 391-337.

To remove the redundant OCS terminator, the vector IC 391-337 was digested with Aat II and then religated. The plant expression vector obtained was named IC 392-337.

9. Preparation of the Plant Expression Vector IC 360-237 Comprising a Coding Nucleic Acid Sequence for a Protein Having the Activity of a GlcN-1-P Mutase and a Bifunctional Protein Having the Bifunctional Activity of a GlcN-1-P Acetyltransferase and a UDP-GlcNAc Pyrophosphorylase from *Escherichia coli*

The starting plasmid for the introduction of the nucleic acid sequence coding for a protein having the bifunctional activity of a GlcN-1-P acetyltransferase and a UDP-GlcNAc-1-P pyrophosphorylase from *Escherichia coli* was the plasmid IC 299-204, described further above, whose coding sequence was isolated by Eco RI restriction digestion and cloned into the Eco RI restriction site of the pMCS5 vector (MoBiTec GmbH, Prod. No.: pMCS5). The vector obtained was named IC 307-204. In the next step, the vector IC 307-204 was digested with Pme I and Sma I restriction endonucleases and religated. The vector obtained was named IC 311-204. The nucleic acid sequence coding for a protein having the activity of a GLMU was then isolated from the plasmid IC 311-204 by restriction digestion with Bam HI and KpnI and ligated into the restriction sites Bam HI and Kpn I of the vector IC 312-204. The vector obtained was named IC 315-204. The vector IC 312-204 was prepared by simultaneous ligation of three fragments composed of a 35S promoter fragment, isolated by Eco RI and Sal I restriction digestion from the plasmid pA7, an ocs fragment isolated by Hind III and Sal I restriction digestion from IC 309-204 and the vector IC310-204, which had been opened by Eco RI restriction digestion. The plasmid IC310-204 is a pUC 18 vector, part of whose MCS has been removed by Hind III and Ed 13511 restriction digestion and subsequent religation. IC 309-204 was prepared by isolating the ocs fragment from pA7 using Hind III and SalI and cloning it into the pBS KS vector, digested with Hind III and Sal I.

From the plasmid IC 315-204, the 35S promoter, the nucleic acid sequence coding for a protein having the bifunctional activity of a glucosamine 1-phosphate acetyltransferase and a UDP-GlcNAc pyrophosphorylase from *E. coli* (qlmu) and the ocs terminator were isolated by Eco RI restriction digestion and cloned into the Eco RI restriction site of the Ubi Bar vector (WO 97 44472). The vector obtained was named IC 359-237.

The starting plasmid for the introduction of the nucleic acid sequence coding for a protein having the activity of a GlcN-1-P mutase is the plasmid IC 299-204 described further above, whose coding sequence was isolated by Sda I and Sma I restriction digestion and ligated into the Sda I and Hpa I restriction sites of the Ubi bar vector. The vector obtained was named IC 355-222.

From the plasmid IC 355-222, the coding sequence of the glmm gene was isolated by Spe I and Dra I restriction digestion and cloned into the Spe I and Pme I restriction sites of the IC 359-237 plasmids. The vector obtained was named IC 360-237.

10. Preparation of the Plant Expression Vector IC 393-337 Comprising Coding Nucleic Acid Sequences for a Protein Having the Activity of a GlcN-6-P Acetyltransferase, a Protein Having the Activity of a UDP-GlcNAc Pyrophosphorylase and a Protein Having the Activity of a GlcNAc-P Mutase from *Saccharomyces cerevisiae*

The starting plasmid for the introduction of the nucleic acid sequence coding for GlcNAc-P mutase from *Saccharomyces cerevisiae* is the plasmid IC 304-204 described further above, whose coding sequence was isolated by Eco RI restriction digestion and cloned into the Eco RI restriction site of the pMCS5 vector (MoBiTec GmbH, Prod. No.: pMCS5). The vector obtained was named IC 313-204. In the next step, the nucleic acid sequence coding for GlcNAc-P mutase from *Saccharomyces cerevisiae* was isolated from the vector IC 313-204 by Pme I and Pac I restriction digestion and cloned into the vector IC 393-337, which had been digested with Pme I and Pac I. The vector obtained was named IC 394-337.

Starting vector for the preparation of the plasmid IC 393-337 is the plasmid IC 391-337 described further above, which already contained the nucleic acid sequences for a protein having the activity of a GlcN-6-P acetyltransferase and a protein having the activity of a UDP-GlcNAc pyrophosphorylase. To this end, the B33 promoter described further above was isolated by Pac I and Avr II restriction digestion and cloned into the vector IC 391-337, which had been digested with Pac I and Avr II. The plant expression vector obtained was named IC 393-337.

11. Transformation of Potato Plants

Potato plants were transformed with the plant expression vector IC 341-222, comprising a coding nucleic acid sequence for a hyaluronan synthase from *Paramecium bursariai Chlorella* virus 1 under the control of the promoter of the patatin gene B33 from *Solanum tuberosum* (Rocha-Sosa et al., 1989, EMBO J. 8, 23-29) according to the method described in General Methods item 1.

The potato plants obtained, transformed with the plasmid IC 341-222, were named 365 ES X, where X denotes plants independently obtained from the transformation. The cultivars obtained after the transformation, named 365 ES X, were analyzed for the amount of the hyaluronan synthesized by the plants in question (see also WO 2006 032538). The cultivars 365 ES 13 and 365 ES 74 were chosen for the transformations described below.

Potato plants of the cultivars 365 ES 13 and 365 ES 74 were transformed with the plant expression vector IC 392-337 or IC 360-237 or IC 394-337 according to the method described in General Methods item 1.

The transgenic potato plants obtained of the cultivar 365 ES 13 transformed with the plasmid IC 392-337 were named 437 ES X, where X denotes plants independently obtained from the transformation.

The transgenic potato plants obtained of the cultivar 365 ES 74 transformed with the plasmid IC 392-337 were named 438 ES X, where X denotes plants independently obtained from the transformation.

The transgenic potato plants obtained of the cultivar 365 ES 13 transformed with the plasmid IC 360-237 were named 397 ES X, where X denotes plants independently obtained from the transformation.

The transgenic potato plants obtained of the cultivar 365 ES 74 transformed with the plasmid IC 360-237 were named 398 ES X, where X denotes plants independently obtained from the transformation.

The potato plants obtained of the cultivar 365 ES 13 transformed with the plasmid IC 393-337 were named 444 ES X, where X denotes plants independently obtained from the transformation.

The potato plants obtained of the cultivar 365 ES 74 transformed with the plasmid IC 393-337 were named 445 ES X, where X denotes plants independently obtained from the transformation.

12. Analysis of Potato Plants Containing Foreign Nucleic Acid Molecules Coding for a Hyaluronan Synthase and Coding for a Protein Having the Activity of a GlcNAc-6-P Acetyltransferase and Coding for a Protein Having the Activity of a UDP-GlcNAc Pyrophosphorylase In a greenhouse, individual plants of the cultivars 365 ES 13, 365 ES 74, 437 ES X, 438 ES X, 397 ES X, 398 ES X, 444 ES X and 445 ES X were cultivated in 6 cm pots in soil. The entire above-ground part of the plant was harvested from 7- to 9-week-old plants and processed according to the method described in General Methods item 3. The amount of hyaluronan in the plant extracts in question was determined by measuring the hyaluronan contained in an aliquot of the plant extracts in question using the method described in General Methods item 4 and with the aid of a calibration curve. For the determination of the hyaluronan content, the supernatant obtained after centrifugation was used in a dilution of 1:10. For selected plants, the following results were obtained:

TABLE 1

Amount of hyaluronan (in μg of hyaluronan per g of fresh weight) produced by independent selected transgenic plants of cultivars 365 ES 13 and 365 ES 74 which only contain a foreign nucleic acid molecule coding for a hyaluronan synthase, in the entire above-ground parts of the plant in question.

| Name of the plant | HA [μg/g fw] |
|---|---|
| 365ES 74-67 | 120.9 |
| 365ES 74-68 | 125.1 |

TABLE 1-continued

Amount of hyaluronan (in µg of hyaluronan per g of fresh weight) produced by independent selected transgenic plants of cultivars 365 ES 13 and 365 ES 74 which only contain a foreign nucleic acid molecule coding for a hyaluronan synthase, in the entire above-ground parts of the plant in question.

| Name of the plant | HA [µg/g fw] |
|---|---|
| 365ES 74-71 | 129.2 |
| 365ES 74-72 | 118.2 |
| 365ES 74-79 | 129.0 |
| 365ES 74-80 | 140.2 |
| 365ES 74-81 | 92.7 |
| 365ES 74-82 | 100.9 |
| wt Desiree 1 | 0.2 |
| wt Desiree 2 | −0.2 |
| wt Desiree 3 | 2.1 |
| 365ES 13-221 | 90.6 |
| 365ES 13-222 | 57.9 |
| 365ES 13-223 | 59.0 |
| 365ES 13-224 | 95.3 |
| 365ES 13-225 | 84.0 |
| 365ES 13-226 | 91.7 |
| 365ES 13-227 | 69.1 |
| 365ES 13-228 | 76.2 |
| 265ES 13-231 | 84.3 |
| 365ES 13-232 | 75.5 |

Column 1 shows the name of the plant from which material was harvested ("wt Desiree" refers to untransformed wild-type plants of the cultivar Désirée).
Column 2 shows the amount of haluronan based on the fresh weight employed.

TABLE 2

Amount of hyaluronan (in µg of hyaluronan per g of fresh weight) produced by independent selected transgenic plants of cultivar 437 ES or 438 ES in the entire above-ground parts of the plant in question.

| Name of the plant | HA [µg/g fw] |
|---|---|
| 438ES 1 | 183.0 |
| 438ES 5 | 192.5 |
| 438ES 10 | 189.5 |
| 438ES 11 | 168.9 |
| 438ES 13 | 195.5 |
| 438ES 14 | 184.3 |
| 438ES 16 | 168.9 |
| 438ES 23 | 231.2 |
| 438ES 25 | 169.2 |
| 438ES 32 | 178.6 |
| 438ES 33 | 173.4 |
| 438ES 41 | 178.7 |
| 438ES 57 | 239.4 |
| 438ES 62 | 172.5 |
| 438ES 64 | 199.5 |
| 438ES 80 | 235.4 |
| 438ES 84 | 189.2 |
| 438ES 85 | 168.1 |
| 438ES 88 | 167.4 |
| 438ES 97 | 164.4 |
| 438ES 102 | 160.4 |
| 438ES 108 | 209.8 |
| 438ES 112 | 185.9 |
| 437ES 2 | 105.6 |
| 437ES 3 | 97.6 |
| 437ES 6 | 129.4 |
| 437ES 12 | 103.2 |
| 437ES 13 | 144.2 |
| 437ES 14 | 163.7 |
| 437ES 15 | 128.2 |
| 437ES 16 | 100.3 |
| 437ES 17 | 186.3 |
| 437ES 21 | 100.7 |
| 437ES 23 | 114.5 |
| 437ES 26 | 105.1 |
| 437ES 31 | 102.0 |
| 437ES 34 | 178.9 |

TABLE 2-continued

Amount of hyaluronan (in µg of hyaluronan per g of fresh weight) produced by independent selected transgenic plants of cultivar 437 ES or 438 ES in the entire above-ground parts of the plant in question.

| Name of the plant | HA [µg/g fw] |
|---|---|
| 437ES 35 | 104.4 |
| 437ES 39 | 98.2 |
| 437ES 40 | 116.8 |
| 437ES 48 | 125.1 |
| 437ES 66 | 146.8 |
| 437ES 69 | 106.8 |
| 437ES 70 | 115.4 |
| 437ES 75 | 100.3 |
| 437ES 76 | 125.5 |
| 437ES 79 | 102.0 |
| 437ES 80 | 125.7 |
| 437ES 82 | 135.7 |
| 437ES 95 | 100.3 |
| 437ES 105 | 108.8 |

Column 1 shows the name of the plant from which material was harvested.
Column 2 shows the amount of haluronan based on the fresh weight employed.

The results shown illustrate that plants containing simultaneously foreign nucleic acid molecules coding for a hyaluronan synthase and coding for a protein having the activity of a GlcN-6-P acetyltransferase and coding for a protein having the activity of a UDP-GlcNAc pyrophosphorylase synthesize considerably higher amounts of hyaluronan than plants containing only a foreign nucleic acid molecule coding for a hyaluronan synthase.

TABLE 3

Amount of hyaluronan (in µg of hyaluronan per g of fresh weight) produced by independent selected transgenic plants of cultivar 397 ES or 398 ES in the entire above-ground parts of the plant in question.

| Name of the plant | HA [µg/g fw] |
|---|---|
| 397 ES 1 | 4.51 |
| 397 ES 2 | 22.54 |
| 397 ES 3 | 16.27 |
| 397 ES 5 | 10.13 |
| 397 ES 6 | 13.60 |
| 397 ES 7 | 33.62 |
| 397 ES 8 | 19.87 |
| 397 ES 9 | 70.37 |
| 397 ES 10 | 51.91 |
| 397 ES 11 | 78.71 |
| 397 ES 12 | 9.76 |
| 397 ES 13 | 6.62 |
| 397 ES 14 | 32.74 |
| 397 ES 16 | 21.34 |
| 397 ES 17 | 81.90 |
| 397 ES 18 | 33.16 |
| 397 ES 19 | 32.18 |
| 397 ES 20 | 26.67 |
| 397 ES 21 | 63.21 |
| 397 ES 22 | 2.66 |
| 397 ES 24 | 1.41 |
| 397 ES 25 | 37.27 |
| 397 ES 26 | 20.34 |
| 397 ES 27 | 32.89 |
| 397 ES 28 | 9.89 |
| 397 ES 29 | 8.31 |
| 397 ES 30 | 85.77 |
| 397 ES 31 | 47.44 |
| 397 ES 32 | 53.47 |
| 397 ES 33 | 5.25 |
| 397 ES 34 | 17.10 |
| 397 ES 35 | 16.80 |
| 397 ES 36 | 17.53 |
| 397 ES 37 | 25.90 |

TABLE 3-continued

Amount of hyaluronan (in μg of hyaluronan per g of fresh weight) produced by independent selected transgenic plants of cultivar 397 ES or 398 ES in the entire above-ground parts of the plant in question.

| Name of the plant | HA [μg/g fw] |
|---|---|
| 397 ES 38 | 7.68 |
| 397 ES 39 | 0.49 |
| 397 ES 40 | 0.85 |
| 397 ES 41 | 14.65 |
| 397 ES 42 | 35.36 |
| 397 ES 43 | 49.96 |
| 397 ES 44 | 28.78 |
| 397 ES 45 | 18.95 |
| 397 ES 46 | 7.93 |
| 397 ES 47 | 28.28 |
| 397 ES 48 | 13.94 |
| 397 ES 49 | 60.16 |
| 397 ES 50 | 29.77 |
| 398 ES 1 | 53.04 |
| 398 ES 2 | 43.64 |
| 398 ES 3 | 130.01 |
| 398 ES 4 | 89.26 |
| 398 ES 5 | 74.35 |
| 398 ES 6 | 55.39 |
| 398 ES 7 | 99.61 |
| 398 ES 8 | 90.82 |
| 398 ES 9 | 41.80 |
| 398 ES 10 | 79.66 |
| 398 ES 11 | 9.57 |
| 398 ES 12 | 41.24 |
| 398 ES 13 | 89.05 |
| 398 ES 14 | 77.19 |
| 398 ES 15 | 96.96 |
| 398 ES 16 | 84.24 |
| 398 ES 17 | 124.63 |
| 398 ES 18 | 76.19 |
| 398 ES 19 | 71.45 |
| 398 ES 20 | 46.17 |
| 398 ES 21 | 80.96 |
| 398 ES 22 | 31.25 |
| 398 ES 23 | 87.35 |
| 398 ES 24 | 62.31 |
| 398 ES 25 | 58.98 |
| 398 ES 26 | 71.14 |
| 398 ES 27 | 18.48 |
| 398 ES 28 | 105.85 |
| 398 ES 29 | 12.24 |
| 398 ES 30 | 95.82 |
| 398 ES 31 | 18.43 |
| 398 ES 32 | 109.41 |
| 398 ES 33 | 87.10 |
| 398 ES 34 | 88.30 |
| 398 ES 35 | 97.85 |
| 398 ES 36 | 58.51 |
| 398 ES 37 | 78.51 |
| 398 ES 38 | 99.67 |
| 398 ES 39 | 11.28 |
| 398 ES 40 | 29.12 |
| 398 ES 41 | 74.15 |
| 398 ES 42 | 22.75 |
| 398 ES 43 | 77.05 |
| 398 ES 44 | 101.34 |
| 398 ES 45 | 57.16 |
| 398 ES 46 | 54.19 |
| 398 ES 47 | 64.35 |
| 398 ES 48 | 60.04 |
| 398 ES 49 | 77.36 |
| 398 ES 50 | 50.84 |

Column 1 shows the name of the plant from which material was harvested.
Column 2 shows the amount of haluronan based on the fresh weight employed.

The results shown illustrate that plants containing simultaneously foreign nucleic acid molecules coding for a hyaluronan synthase and coding for a protein having the activity of a GlcN-P mutase and a protein having the bifunctional activity of a GlcN-1-P acetyltransferase and a UDP-GlcNAc pyrophosphorylase do not synthesize significantly higher amounts of hyaluronan than plants containing only a foreign nucleic acid molecule coding for a hyaluronan synthase.

TABLE 4

Amount of hyaluronan (in μg of hyaluronan per g of fresh weight) produced by independent selected transgenic plants of cultivar 444 ES or 445 ES in the entire above-ground parts of the plant in question.

| Name of the plant | HA [μg/g fw] |
|---|---|
| 444ES 6 | 81.06 |
| 444ES 12 | 95.89 |
| 444ES 14 | 90.76 |
| 444ES 17 | 83.20 |
| 444ES 19 | 69.18 |
| 444ES 23 | 59.45 |
| 444ES 27 | 58.93 |
| 444ES 35 | 58.45 |
| 444ES 37 | 67.34 |
| 444ES 41 | 63.27 |
| 444ES 43 | 60.82 |
| 445ES 1 | 102.53 |
| 445ES 6 | 99.65 |
| 445ES 7 | 152.66 |
| 445ES 8 | 82.24 |
| 445ES 9 | 119.74 |
| 445ES 12 | 82.68 |
| 445ES 16 | 102.24 |
| 445ES 18 | 86.47 |
| 445ES 19 | 103.37 |
| 445ES 20 | 96.06 |
| 445ES 23 | 116.64 |
| 445ES 24 | 95.13 |
| 445ES 34 | 87.24 |
| 445ES 40 | 81.74 |
| 445ES 42 | 98.72 |
| 445ES 47 | 84.41 |
| 445ES 60 | 86.71 |
| 445ES 135 | 94.13 |

Column 1 shows the name of the plant from which material was harvested.
Column 2 shows the amount of haluronan based on the fresh weight employed.

The results shown illustrate that plants containing simultaneously foreign nucleic acid molecules coding for a hyaluronan synthase and coding for a protein having the activity of a GlcN-P mutase and a protein having the activity of a GlcN-6-P acetyltransferase and a protein having the activity of a UDP-GlcNAc pyrophosphorylase do not synthesize significantly higher amounts of hyaluronan than plants containing only a foreign nucleic acid molecule coding for a hyaluronan synthase and a protein having the activity of a GlcN-6-P acetyltransferase and a protein having the activity of a UDP-GlcNAc pyrophosphorylase.

The invention claimed is:

1. A genetically modified plant cell comprising
   (a) a foreign nucleic acid molecule coding for a hyaluronan synthase,
   (b) a foreign nucleic acid molecule coding for a protein having the activity of a glucosamine 6-phosphate acetyltransferase and
   (c) a foreign nucleic acid molecule coding for a protein having the activity of a monofunctional UDP-N-acetyl-glucosamine pyrophosphorylase,
   wherein said genetically modified plant cell produces an increased amount of hyaluronan as compared to a genetically modified plant cell comprising a nucleic acid molecule which is stably integrated into its genome and codes for a hyaluronan synthase.

2. A plant comprising the genetically modified plant cell of claim 1.

3. Propagation material comprising the genetically modified plant cell of claim 1.

4. Harvestable plant parts comprising the genetically modified plant cell of claim 1.

5. A process for producing a plant comprising
   (a) genetically modifying a plant cell comprising introducing
      (i) a nucleic acid molecule coding for a protein having the activity of a hyaluronan synthase;
      (ii) a nucleic acid molecule coding for a protein having the activity of a glucosamine 6-phosphate acetyltransferase; and
      (iii) a nucleic acid molecule coding for a protein having the monofunctional activity of a UDP-N-acetyl-glucosamine pyrophosphorylase into a plant cell; and
   (b) regenerating a plant from plant cells from step (a),
   wherein said genetically modified plant cell produces an increased amount of hyaluronan as compared to a genetically modified plant cell comprising a nucleic acid molecule which is stably integrated into its genome and codes for a hyaluronan synthase.

6. A process for producing hyaluronan comprising the step of extracting hyaluronan from the genetically modified plant cell of claim 1.

7. A composition comprising the genetically modified plant cell of claim 1.

8. A process for preparing a composition comprising extracting hyaluronan from the genetically modified plant cell of claim 1, and preparing a composition including said hyaluronan.

9. A process for producing hyaluronan comprising the step of extracting hyaluronan from the plant of claim 2.

10. A process for producing hyaluronan comprising the step of extracting hyaluronan from the propagation material of claim 3.

11. A process for producing hyaluronan comprising the step of extracting hyaluronan from the harvestable plant parts of claim 4.

12. A process for producing hyaluronan comprising the step of extracting hyaluronan from plants obtainable by a process of claim 5.

13. A process for preparing a composition comprising extracting hyaluronan from the plant of claim 2 and preparing a composition including said hyaluronan.

14. A process for preparing a composition comprising extracting hyaluronan from the propagation material of claim 3 and preparing a composition including said hyaluronan.

15. A process for preparing a composition comprising extracting hyaluronan from the harvestable plant parts of claim 4 and preparing a composition including said hyaluronan.

16. A process for preparing a composition comprising extracting hyaluronan using a plant obtainable by the process of claim 5 and preparing a composition including said hyaluronan.

17. The process of claim 5, further comprising generating additional plants using the plants according to step (b).

18. The process of claim 5, wherein steps (a)(i) to (a)(iii) can be carried out in any order, individually, or simultaneously.

19. The genetically modified plant cell of claim 1, wherein said plant cell produces at least 160 µg hyaluronan per gram fresh weight.

20. The process of claim 5, wherein said plant cell produces at least 160 µg hyaluronan per gram fresh weight.

21. A genetically modified plant cell comprising
   (a) a foreign nucleic acid molecule coding for a hyaluronan synthase,
   (b) a foreign nucleic acid molecule coding for a protein having the activity of a glucosamine 6-phosphate acetyltransferase and
   (c) a foreign nucleic acid molecule coding for a protein having the activity of a monofunctional UDP-N-acetyl-glucosamine pyrophosphorylase,
   wherein said plant cell produces at least 160 µg hyaluronan per gram fresh weight.

22. The genetically modified plant cell of claim 1, wherein said plant cell produces 160 to 450 µg hyaluronan per gram fresh weight.

23. The genetically modified plant cell of claim 1, wherein said plant cell produces 160 to 400 µg hyaluronan per gram fresh weight.

24. The genetically modified plant cell of claim 1, wherein said plant cell produces 160 to 300 µg hyaluronan per gram fresh weight.

25. The genetically modified plant cell of claim 1, wherein said plant cell produces 160 to 280 µg hyaluronan per gram fresh weight.

26. The genetically modified plant cell of claim 1, wherein said plant cell produces 160 to 260 µg hyaluronan per gram fresh weight.

27. The process of claim 5, wherein said plant cell produces 160 to 450 µg hyaluronan per gram fresh weight.

28. The process of claim 5, wherein said plant cell produces 160 to 400 µg hyaluronan per gram fresh weight.

29. The process of claim 5, wherein said plant cell produces 160 to 300 µg hyaluronan per gram fresh weight.

30. The process of claim 5, wherein said plant cell produces 160 to 280 µg hyaluronan per gram fresh weight.

31. The process of claim 5, wherein said plant cell produces 160 to 260 µg hyaluronan per gram fresh weight.

32. The genetically modified plant cell of claim 21, wherein said plant cell produces 160 to 450 µg hyaluronan per gram fresh weight.

33. The genetically modified plant cell of claim 21, wherein said plant cell produces 160 to 400 µg hyaluronan per gram fresh weight.

34. The genetically modified plant cell of claim 21, wherein said plant cell produces 160 to 300 µg hyaluronan per gram fresh weight.

35. The genetically modified plant cell of claim 21, wherein said plant cell produces 160 to 280 µg hyaluronan per gram fresh weight.

36. The genetically modified plant cell of claim 21, wherein said plant cell produces 160 to 260 µg hyaluronan per gram fresh weight.

37. The genetically modified plant cell of claim 1, wherein the foreign nucleic acid molecule coding for a hyaluronan synthase comprises a nucleic acid sequence that is at least 95% identical to the nucleic acid sequence of SEQ ID NO: 1 or SEQ ID NO: 3.

38. The genetically modified plant cell of claim 1, wherein the foreign nucleic acid molecule coding for a protein having the activity of a glucosamine 6-phosphate acetyltransferase comprises a nucleic acid sequence that is at least 95% identical to the nucleic acid sequence of SEQ ID NO: 8.

39. The genetically modified plant cell of claim 1, wherein the foreign nucleic acid molecule coding for a protein having the activity of a monofunctional UDP-N-acetyl-glucosamine pyrophosphorylase comprises a nucleic acid sequence that is at least 95% identical to the nucleic acid sequence of SEQ ID NO: 10.

40. The process of claim 5, wherein the foreign nucleic acid molecule coding for a hyaluronan synthase comprises a nucleic acid sequence that is at least 95% identical to the nucleic acid sequence of SEQ ID NO: 1 or SEQ ID NO: 3.

41. The process of claim 5, wherein the foreign nucleic acid molecule coding for a protein having the activity of a glucosamine 6-phosphate acetyltransferase comprises a nucleic acid sequence that is at least 95% identical to the nucleic acid sequence of SEQ ID NO: 8.

42. The process of claim 5, wherein the foreign nucleic acid molecule coding for a protein having the activity of a monofunctional UDP-N-acetyl-glucosamine pyrophosphorylase comprises a nucleic acid sequence that is at least 95% identical to the nucleic acid sequence of SEQ ID NO: 10.

43. The genetically modified plant cell of claim 21, wherein the foreign nucleic acid molecule coding for a hyaluronan synthase comprises a nucleic acid sequence that is at least 95% identical to the nucleic acid sequence of SEQ ID NO: 1 or SEQ ID NO: 3.

44. The genetically modified plant cell of claim 21, wherein the foreign nucleic acid molecule coding for a protein having the activity of a glucosamine 6-phosphate acetyltransferase comprises a nucleic acid sequence that is at least 95% identical to the nucleic acid sequence of SEQ ID NO: 8.

45. The genetically modified plant cell of claim 21, wherein the foreign nucleic acid molecule coding for a protein having the activity of a monofunctional UDP-N-acetyl-glucosamine pyrophosphorylase comprises a nucleic acid sequence that is at least 95% identical to the nucleic acid sequence of SEQ ID NO: 10.

\* \* \* \* \*